(12) United States Patent
Sugiyama

(10) Patent No.: US 11,732,018 B2
(45) Date of Patent: Aug. 22, 2023

(54) CANCER ANTIGEN HELPER PEPTIDE

(71) Applicant: International Institute Of Cancer Immunology, Inc., Osaka (JP)

(72) Inventor: Haruo Sugiyama, Osaka (JP)

(73) Assignee: International Institute Of Cancer Immunology, Inc., Osaka (JP)

( * ) Notice: Subject to any disclaimer, the term of this patent is extended or adjusted under 35 U.S.C. 154(b) by 391 days.

(21) Appl. No.: 16/937,619

(22) Filed: Jul. 24, 2020

(65) Prior Publication Data

US 2021/0107957 A1  Apr. 15, 2021

Related U.S. Application Data

(60) Continuation of application No. 15/831,484, filed on Dec. 5, 2017, now Pat. No. 10,759,840, which is a continuation of application No. 14/994,801, filed on Jan. 13, 2016, now abandoned, which is a division of application No. 13/265,805, filed as application No. PCT/JP2010/057149 on Apr. 22, 2010, now Pat. No. 9,266,932.

(30) Foreign Application Priority Data

Apr. 23, 2009  (JP) .................................. 2009-105286

(51) Int. Cl.
| | |
|---|---|
| A61K 38/00 | (2006.01) |
| C07K 14/47 | (2006.01) |
| G01N 33/574 | (2006.01) |
| A61K 39/00 | (2006.01) |
| C07K 16/18 | (2006.01) |
| C07K 16/30 | (2006.01) |
| C12N 5/078 | (2010.01) |
| G01N 33/569 | (2006.01) |

(52) U.S. Cl.
CPC .. *C07K 14/4748* (2013.01); *A61K 39/001153* (2018.08); *C07K 14/4702* (2013.01); *C07K 16/18* (2013.01); *C07K 16/30* (2013.01); *C12N 5/0634* (2013.01); *G01N 33/56966* (2013.01); *G01N 33/57438* (2013.01); *A61K 38/00* (2013.01); *A61K 39/00* (2013.01); *A61K 2039/55566* (2013.01)

(58) Field of Classification Search
CPC ........................ A61K 39/001153; A61K 38/00; A61K 39/00; C07K 16/30
See application file for complete search history.

(56) References Cited

U.S. PATENT DOCUMENTS

| | | | |
|---|---|---|---|
| 5,622,835 A | 4/1997 | Herlyn et al. | |
| 7,063,854 B1 | 6/2006 | Gaiger et al. | |
| 7,144,581 B2 | 12/2006 | Gaiger et al. | |
| 7,312,243 B1 | 12/2007 | Pravda | |
| 8,617,531 B2 | 12/2013 | Cox et al. | |
| 10,525,096 B2 | 1/2020 | Sugiyama | |
| 2003/0039635 A1 | 2/2003 | Gaiger et al. | |
| 2003/0072767 A1 | 4/2003 | Gaiger et al. | |
| 2003/0082196 A1 | 5/2003 | Gaiger et al. | |
| 2003/0095971 A1 | 5/2003 | Gaiger et al. | |
| 2003/0198622 A1 | 10/2003 | Gaiger et al. | |
| 2003/0215458 A1 | 11/2003 | Gaiger et al. | |
| 2003/0235557 A1 | 12/2003 | Gaiger et al. | |
| 2004/0043950 A1 | 3/2004 | Lopez-Berestein et al. | |
| 2008/0015137 A1 | 1/2008 | Chook | |
| 2008/0070835 A1 | 3/2008 | Sugiyaya | |
| 2010/0247556 A1 | 9/2010 | Sugiyama | |
| 2011/0318380 A1 | 12/2011 | Brix et al. | |
| 2013/0266958 A1 | 10/2013 | Sugiyama | |

FOREIGN PATENT DOCUMENTS

| | | |
|---|---|---|
| CA | 2813557 A1 | 4/2012 |
| CN | 1505526 A | 6/2004 |
| CN | 1671733 A | 9/2005 |
| CN | 1902313 A | 1/2007 |
| EP | 1117687 | 6/2008 |
| JP | H 08-289780 | 11/1996 |
| JP | 2005-518192 | 6/2005 |
| WO | WO 01/25273 A2 | 4/2001 |
| WO | WO 02/28414 A1 | 4/2002 |
| WO | WO 03/037060 A2 | 5/2003 |
| WO | WO 2005/045027 A1 | 5/2005 |
| WO | WO 2007/047764 A2 | 4/2007 |
| WO | WO 2008/076933 A2 | 6/2008 |
| WO | WO 2008/105462 A1 | 9/2008 |

OTHER PUBLICATIONS

Pages 1-450 of WO2010037395 (Year: 2010).*
Pages 451-900 of WO2010037395 (Year: 2010).*
Pages 901-1228 of WO2010037395 (Year: 2010).*
Office Action dated Sep. 22, 2016 issued in Canadian Patent Application No. 2,757,764 (5 pages).
A.L. Menke et al., "The Wilms' Tumor 1 Gene: Oncogene or Tumor Suppressor Gene?" *International Review of Cytology*, 1998, 181: 151-212.
Akhiro Tsuboi et al., "Cytotoxic T-Lymphocyte Responses Elicited to Wilms' Tumor Gene WT1 Product by DNA Vaccination," *Journal of Clinical Immunology*, May 2000, 20(3): 195-202.
Akihiro Tsuboi et al., "Constitutive expression of the Wilms' tumor gene WT1 inhibits the differentiation of myeloid progenitor cells but promotes their proliferation in response to granulocyte-colony stimulating factor (GCSF)," *Leukemia Research*, May 1999, 23(5): 499-505.
Cornelis J.M. Melief et al., "T-Cell Immunotherapy of Tumors by Adoptive Transfer of Cytotoxic T Lymphocytes and b Vaccination with Minimal Essential Epitopes," *Immunological Reviews*, Jun. 1995, 145: 167-177.

(Continued)

*Primary Examiner* — Sheela J. Huff
(74) *Attorney, Agent, or Firm* — Finnegan, Henderson, Farabow, Garrett & Dunner, LLP

(57) ABSTRACT

The present invention relates to a WT1 peptide which has an amino acid sequence consisting of contiguous amino acids derived from a WT1 protein and induces WT1-specific helper T cells by binding to an MHC class II molecule, a pharmaceutical composition comprising them and the like.

12 Claims, 10 Drawing Sheets

Specification includes a Sequence Listing.

(56) References Cited

OTHER PUBLICATIONS

Daniel A. Haber et al., "An Internal Deletion within an 11p13 Zinc Finger Gene Contributes to the Development of Wilms' Tumor," *Cell*, Jun. 29, 1990, 61(7): 1257-1269.
Fujiki et al.; "a WT1 Protein-Derived, Naturally Processed 16-MER Peptide, WT1332, Is a Promiscuous Helper Peptide for Induction of WT1-Specific TH1-Type CD4+ T Cells", Microbiol. Immunol., vol. 52, No. 12, pp. 591-600, (2008).
Fujiki et al.; "Identification and Characterization of a WT1 (Wilms Tumor Gene) Proteinderived HLA-DRB1*0405-Restricted 16-MER Helper Peptide That Promotes the Induction and Activation of WT1-Specific Cytotoxic T Lymphocyytes", J. Immunother, vol. 30, No. 3, pp. 282-293, (2007).
Fujiki et al.; "WT1 Tokuiteki CD4+ Helper T Saibo O HLA-Class II Kosokusei NI Yudo Dekiru WT1 Peptide No Dotei to Sono Yuyosei No Kento," The Japanese Society for Immunology Gakujutsu Shukai Kiroku, pp. 187-188, (2005).
Gang Zeng, "MHC Class II-Restricted Tumor Antigens Recognized by CD4+ T Cells: New Strategies for Cancel Vaccine Design," *Journal of Immunotherapy*, 2001, 24: 195-204.
Geng Guang Fao et al., "Antigen-specific CD4+ T-Cell Help Is Required to Activate a Memory CD8+ T Cell to a Fully Functional Tumor Killer Cell1," *Cancer Research*, 2002, 62: 6438-6441.
Guo et al.; "Direct Recognition and Lysis of Leukemia Cells by WT1-Specific CD4+ T Lymphocytes in an HLA Class II-Restricted Manner", Blood, vol. 106, No. 4, pp. 1415-1418, (2005).
Hideki Ohminami et al., "HLC class I-restricted lysis of leukemia cells by a CD8+ cytotoxic T-lymphocyte clone specific for WT1 peptide," *Blood*, Jan. 1, 2000, 95(1): 286-293.
Intellectual Property Office of New Zealand, "Examination Report," dated Apr. 10, 2012, 2 pages, issued in corresponding New Zealand Application No. 595707.
International Preliminary Report on Patentability dated Dec. 1, 2011 issued in International Application No. PCT/JP2010/057149.
International Search Report from the Japanese Patent Office for International Application No. PCT/JP2010/057149, dated May 11, 2010.
Jerome Ritz, "Tumor Immunity: Will New Keys Unlock the Door?," *Journal of Clinical Oncology*, Feb. 1994, 12(2): 237-238.
Katherine M. Call et al., "Isolation and Characterization of a Zinc Finger Polypeptide Gene at the Human Chromosome 11 Wilms' Tumor Locus," *Cell*, Feb. 9, 1990, 60(3): 509-520.

Kazushi Inoue et al., "Wilms' Tumor Gene (WT1) Competes With Differentiation-Inducing Signal in Hematopoietic Progenitor Cells," *Blood*, Apr. 15, 1998, 91*8): 2969-2976.
Knights et al.; "Prediction of an HLA-DR-Binding Peptide Derived From Wilms' Tumour 1 Protein and Demonstration of in Vitro Immunogenicity of WT1 (124-138)-Pulsed Dendritic Cells Generated According to an Optimised Protocol", Cancer Immunol Immunother, vol. 51, No. 5, pp. 271-281, (2002).
Lehe et al.; "The Wilms' Tumor Antigen Is a Novel Target for Human CD4+ Regulatory T Cells, Implications for Immunotherapy", Cancer Res., vol. 68, No. 15, pp. 6350-6359, (2008).
Liquan Gao et al., Selective elimination of leukemic CD34+ progenitor cells by cytotoxic T lymphocytes specific for WT1, *Blood*, Jan. 1, 2000, 95(7): 2198-2203.
May, RJ et al., "Peptide Epitopes from the Wilms' Tumor 1 Oncoprotein Stimulate CD4+ and CD8+ T Cells That Recognize and Kill Human Malignant Mesothelioma Tumor Cells," Clinical Cancer Research, vol. 13(15):4547-4555 (2007).
Official Action, dated Sep. 27, 2019, issued in Brazilian Patent Application No. PI 1014998-8.
Office Action dated Apr. 15, 2014 issued in corresponding Russian Patent Application No. 2011147479 and its English translation.
Office Action and Search Report for corresponding Chinese Application No. 201080028991.4 dated Jan. 8, 2014.
Office Action and Search Report for corresponding Chinese Application No. 201080028991.4 dated Mar. 26, 2013.
Office Action for corresponding Ukraine Application No. 201113728 dated Jul. 9, 2013.
Office Action for JP Application No. 2011-510358 dated Aug. 26, 2014.
Pakistan Patent Office, "First Official Action," dated May 23, 2011, 6 pages, Lahore, Pakistan.
Roit A. et al., Immunology, Moscow, "Mir", 2000, pp. 194-195 and its English translation.
Supplementary European Search Report dated Oct. 17, 2012; European application EP 10 76 7122; 7 pages.
Tamotsu Yamagami et al., "Growth Inhibition of Human Leukemic Cells by WT1 (Wilms Tumor Gene) Antisense Oligodeoxynucheotides: Implications for the Involvement of WT1 in Leukemogenesis," *Blood*, Apr. 1, 1996; 87(7): 2878-2884.
Yoshihiro Oka et al., "Cancer Immunotherapy Targeting Wilms' Tumor Gene WT1 Product1," *Journal of Immunology*, Feb. 15, 2000, 164(4): 1873-1880.
Yoshihiro Oka et al. "Human cytotoxic T-lymphocyte responses specific for peptides of the wild-type Wilms' tumor gene (WT1) product," *Immunogenetics*, Feb. 2000, 51(2): 99-107.

* cited by examiner

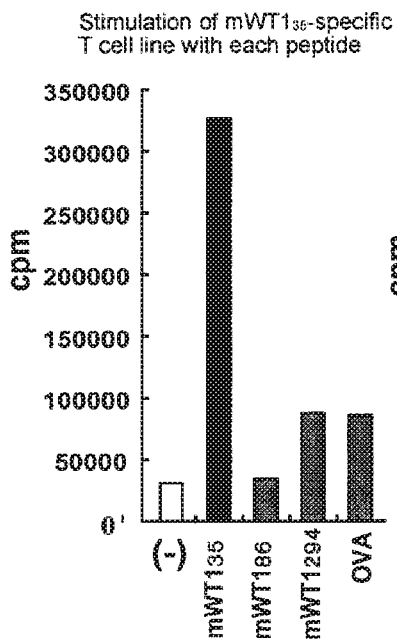
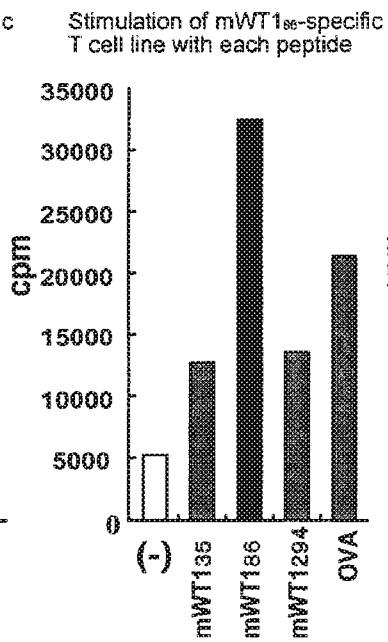
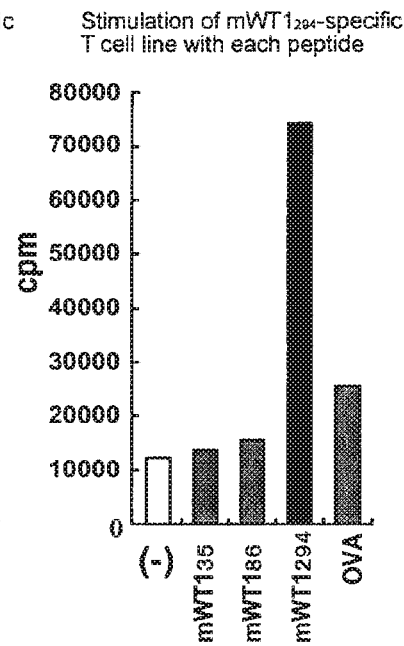
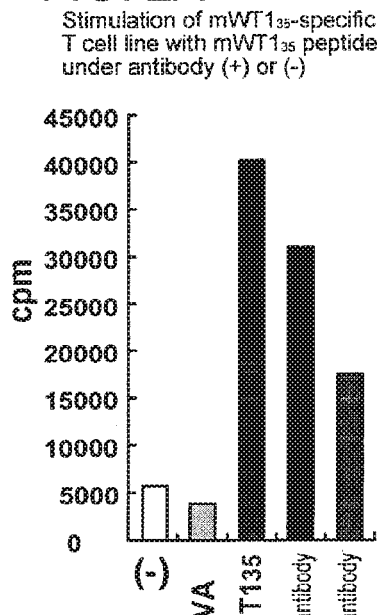
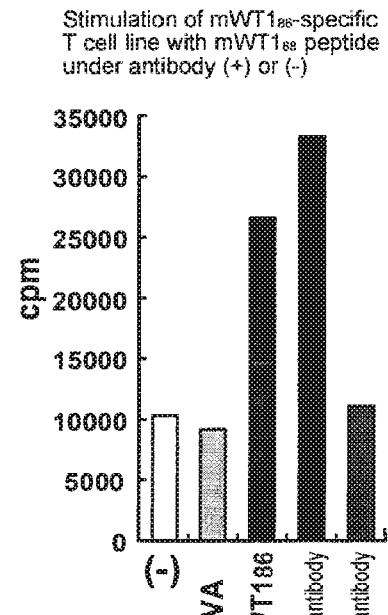
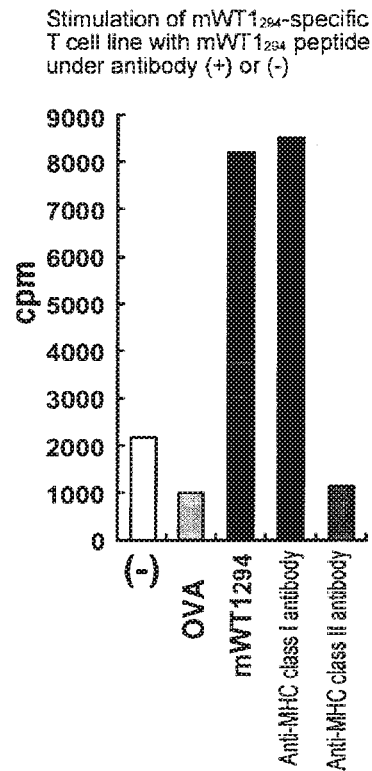

SEQUENCE LISTING

```
<160> NUMBER OF SEQ ID NOS: 74

<210> SEQ ID NO 1
<211> LENGTH: 449
<212> TYPE: PRT
<213> ORGANISM: Mus musculus

<400> SEQUENCE: 1

Met Gly Ser Asp Val Arg Asp Leu Asn Ala Leu Leu Pro Ala Val Ser
1               5                   10                  15

Ser Leu Gly Gly Gly Gly Gly Cys Gly Leu Pro Val Ser Gly Ala
            20                  25                  30

Arg Gln Trp Ala Pro Val Leu Asp Phe Ala Pro Pro Gly Ala Ser Ala
        35                  40                  45

Tyr Gly Ser Leu Gly Gly Pro Ala Pro Pro Ala Pro Pro Pro
    50                  55                  60

Pro Pro Pro His Ser Phe Ile Lys Gln Glu Pro Ser Trp Gly Gly
65                  70                  75                  80

Ala Glu Pro His Glu Glu Gln Cys Leu Ser Ala Phe Thr Leu His Phe
                85                  90                  95

Ser Gly Gln Phe Thr Gly Thr Ala Gly Ala Cys Arg Tyr Gly Pro Phe
            100                 105                 110

Gly Pro Pro Pro Ser Gln Ala Ser Ser Gly Gln Ala Arg Met Phe
        115                 120                 125

Pro Asn Ala Pro Tyr Leu Pro Ser Cys Leu Glu Ser Gln Pro Thr Ile
    130                 135                 140

Arg Asn Gln Gly Tyr Ser Thr Val Thr Phe Asp Gly Ala Pro Ser Tyr
145                 150                 155                 160

Gly His Thr Pro Ser His His Ala Ala Gln Phe Pro Asn His Ser Phe
                165                 170                 175

Lys His Glu Asp Pro Met Gly Gln Gln Gly Ser Leu Gly Glu Gln Gln
            180                 185                 190

Tyr Ser Val Pro Pro Val Tyr Gly Cys His Thr Pro Thr Asp Ser
        195                 200                 205

Cys Thr Gly Ser Gln Ala Leu Leu Leu Arg Thr Pro Tyr Ser Ser Asp
    210                 215                 220

Asn Leu Tyr Gln Met Thr Ser Gln Leu Glu Cys Met Thr Trp Asn Gln
225                 230                 235                 240

Met Asn Leu Gly Ala Thr Leu Lys Gly Met Ala Ala Gly Ser Ser Ser
                245                 250                 255

Ser Val Lys Trp Thr Glu Gly Gln Ser Asn His Gly Ile Gly Tyr Glu
```

```
                    260                 265                 270
Ser Glu Asn His Thr Ala Pro Ile Leu Cys Gly Ala Gln Tyr Arg Ile
                275                 280                 285

His Thr His Gly Val Phe Arg Gly Ile Gln Asp Val Arg Arg Val Ser
            290                 295                 300

Gly Val Ala Pro Thr Leu Val Arg Ser Ala Ser Glu Thr Ser Glu Lys
305                 310                 315                 320

Arg Pro Phe Met Cys Ala Tyr Pro Gly Cys Asn Lys Arg Tyr Phe Lys
                325                 330                 335

Leu Ser His Leu Gln Met His Ser Arg Lys His Thr Gly Glu Lys Pro
            340                 345                 350

Tyr Gln Cys Asp Phe Lys Asp Cys Glu Arg Arg Phe Ser Arg Ser Asp
                355                 360                 365

Gln Leu Lys Arg His Gln Arg Arg His Thr Gly Val Lys Pro Phe Gln
            370                 375                 380

Cys Lys Thr Cys Gln Arg Lys Phe Ser Arg Ser Asp His Leu Lys Thr
385                 390                 395                 400

His Thr Arg Thr His Thr Gly Lys Thr Ser Glu Lys Pro Phe Ser Cys
                405                 410                 415

Arg Trp His Ser Cys Gln Lys Lys Phe Ala Arg Ser Asp Glu Leu Val
            420                 425                 430

Arg His His Asn Met His Gln Arg Asn Met Thr Lys Leu His Val Ala
                435                 440                 445

Leu

<210> SEQ ID NO 2
<211> LENGTH: 449
<212> TYPE: PRT
<213> ORGANISM: Homo sapiens

<400> SEQUENCE: 2

Met Gly Ser Asp Val Arg Asp Leu Asn Ala Leu Leu Pro Ala Val Pro
1               5                   10                  15

Ser Leu Gly Gly Gly Gly Gly Cys Ala Leu Pro Val Ser Gly Ala Ala
            20                  25                  30

Gln Trp Ala Pro Val Leu Asp Phe Ala Pro Pro Gly Ala Ser Ala Tyr
        35                  40                  45

Gly Ser Leu Gly Gly Pro Ala Pro Pro Pro Ala Pro Pro Pro Pro Pro
    50                  55                  60

Pro Pro Pro Pro His Ser Phe Ile Lys Gln Glu Pro Ser Trp Gly Gly
65                  70                  75                  80

Ala Glu Pro His Glu Glu Gln Cys Leu Ser Ala Phe Thr Val His Phe
                85                  90                  95

Ser Gly Gln Phe Thr Gly Thr Ala Gly Ala Cys Arg Tyr Gly Pro Phe
            100                 105                 110

Gly Pro Pro Pro Ser Gln Ala Ser Ser Gly Gln Ala Arg Met Phe Pro
        115                 120                 125

Pro Asn Ala Pro Tyr Leu Pro Ser Cys Leu Glu Ser Gln Pro Ala Ile
    130                 135                 140

Arg Asn Gln Gly Tyr Ser Thr Val Thr Phe Asp Gly Thr Pro Ser Tyr
145                 150                 155                 160

Gly His Thr Pro Ser His His Ala Ala Gln Phe Pro Asn His Ser Phe
                165                 170                 175

Lys His Glu Asp Pro Met Gly Gln Gln Gly Ser Leu Gly Glu Gln Gln
```

```
                180             185             190
Tyr Ser Val Pro Pro Val Tyr Gly Cys His Thr Pro Thr Asp Ser
        195                 200                 205
Cys Thr Gly Ser Gln Ala Leu Leu Arg Thr Pro Tyr Ser Ser Asp
        210                 215                 220
Asn Leu Tyr Gln Met Thr Ser Gln Leu Glu Cys Met Thr Trp Asn Gln
225                 230                 235                 240
Met Asn Leu Gly Ala Thr Leu Lys Gly Val Ala Ala Gly Ser Ser Ser
                245                 250                 255
Ser Val Lys Trp Thr Glu Gly Gln Ser Asn His Ser Thr Gly Tyr Glu
            260                 265                 270
Ser Asp Asn His Thr Thr Pro Ile Leu Cys Gly Ala Gln Tyr Arg Ile
        275                 280                 285
His Thr His Gly Val Phe Arg Gly Ile Gln Asp Val Arg Arg Val Pro
        290                 295                 300
Gly Val Ala Pro Thr Leu Val Arg Ser Ala Ser Glu Thr Ser Glu Lys
305                 310                 315                 320
Arg Pro Phe Met Cys Ala Tyr Pro Gly Cys Asn Lys Arg Tyr Phe Lys
                325                 330                 335
Leu Ser His Leu Gln Met His Ser Arg Lys His Thr Gly Glu Lys Pro
            340                 345                 350
Tyr Gln Cys Asp Phe Lys Asp Cys Glu Arg Arg Phe Ser Arg Ser Asp
        355                 360                 365
Gln Leu Lys Arg His Gln Arg Arg His Thr Gly Val Lys Pro Phe Gln
    370                 375                 380
Cys Lys Thr Cys Gln Arg Lys Phe Ser Arg Ser Asp His Leu Lys Thr
385                 390                 395                 400
His Thr Arg Thr His Thr Gly Lys Thr Ser Glu Lys Pro Phe Ser Cys
                405                 410                 415
Arg Trp Pro Ser Cys Gln Lys Lys Phe Ala Arg Ser Asp Glu Leu Val
            420                 425                 430
Arg His His Asn Met His Gln Arg Asn Met Thr Lys Leu Gln Leu Ala
        435                 440                 445
Leu

<210> SEQ ID NO 3
<211> LENGTH: 18
<212> TYPE: PRT
<213> ORGANISM: Unknown
<220> FEATURE:
<223> OTHER INFORMATION: Description of Unknown: mWT135 or hWT135
    peptide
<220> FEATURE:
<223> OTHER INFORMATION: This sequence may be human or mouse

<400> SEQUENCE: 3

Trp Ala Pro Val Leu Asp Phe Ala Pro Pro Gly Ala Ser Ala Tyr Gly
1               5                   10                  15

Ser Leu

<210> SEQ ID NO 4
<211> LENGTH: 17
<212> TYPE: PRT
<213> ORGANISM: Homo sapiens

<400> SEQUENCE: 4

Glu Gln Cys Leu Ser Ala Phe Thr Val His Phe Ser Gly Gln Phe Thr
```

-continued

```
1               5                   10                  15

Gly

<210> SEQ ID NO 5
<211> LENGTH: 19
<212> TYPE: PRT
<213> ORGANISM: Homo sapiens

<400> SEQUENCE: 5

Phe Arg Gly Ile Gln Asp Val Arg Arg Val Pro Gly Val Ala Pro Thr
1               5                   10                  15

Leu Val Arg

<210> SEQ ID NO 6
<211> LENGTH: 17
<212> TYPE: PRT
<213> ORGANISM: Mus musculus

<400> SEQUENCE: 6

Glu Gln Cys Leu Ser Ala Phe Thr Leu His Phe Ser Gly Gln Phe Thr
1               5                   10                  15

Gly

<210> SEQ ID NO 7
<211> LENGTH: 19
<212> TYPE: PRT
<213> ORGANISM: Mus musculus

<400> SEQUENCE: 7

Phe Arg Gly Ile Gln Asp Val Arg Arg Val Ser Gly Val Ala Pro Thr
1               5                   10                  15

Leu Val Arg

<210> SEQ ID NO 8
<211> LENGTH: 9
<212> TYPE: PRT
<213> ORGANISM: Mus musculus

<400> SEQUENCE: 8

Arg Met Phe Pro Asn Ala Pro Tyr Leu
1               5

<210> SEQ ID NO 9
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: F, L, M, V, W or Y
<220> FEATURE:
<221> NAME/KEY: MOD_RES
<222> LOCATION: (2)..(2)
<223> OTHER INFORMATION: Any amino acid
<220> FEATURE:
<221> NAME/KEY: MOD_RES
<222> LOCATION: (3)..(3)
<223> OTHER INFORMATION: Any amino acid
<220> FEATURE:
<221> NAME/KEY: MOD_RES
<222> LOCATION: (4)..(4)
<223> OTHER INFORMATION: Any amino acid
<220> FEATURE:
```

-continued

```
<221> NAME/KEY: MOD_RES
<222> LOCATION: (5)..(5)
<223> OTHER INFORMATION: F, L, M or Y
<220> FEATURE:
<221> NAME/KEY: MOD_RES
<222> LOCATION: (6)..(6)
<223> OTHER INFORMATION: Any amino acid
<220> FEATURE:
<221> NAME/KEY: MOD_RES
<222> LOCATION: (7)..(7)
<223> OTHER INFORMATION: Any amino acid
<220> FEATURE:
<221> NAME/KEY: MOD_RES
<222> LOCATION: (8)..(8)
<223> OTHER INFORMATION: I, A, M or V

<400> SEQUENCE: 9

Xaa Xaa Xaa Xaa Xaa Xaa Xaa Xaa
1               5

<210> SEQ ID NO 10
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Y, L, V, F or K
<220> FEATURE:
<221> NAME/KEY: MOD_RES
<222> LOCATION: (2)..(2)
<223> OTHER INFORMATION: Any amino acid
<220> FEATURE:
<221> NAME/KEY: MOD_RES
<222> LOCATION: (3)..(3)
<223> OTHER INFORMATION: Any amino acid
<220> FEATURE:
<221> NAME/KEY: MOD_RES
<222> LOCATION: (4)..(4)
<223> OTHER INFORMATION: D, S, Q or T
<220> FEATURE:
<221> NAME/KEY: MOD_RES
<222> LOCATION: (5)..(5)
<223> OTHER INFORMATION: Any amino acid
<220> FEATURE:
<221> NAME/KEY: MOD_RES
<222> LOCATION: (6)..(6)
<223> OTHER INFORMATION: Y, F, W or V
<220> FEATURE:
<221> NAME/KEY: MOD_RES
<222> LOCATION: (7)..(7)
<223> OTHER INFORMATION: Any amino acid
<220> FEATURE:
<221> NAME/KEY: MOD_RES
<222> LOCATION: (8)..(8)
<223> OTHER INFORMATION: Any amino acid
<220> FEATURE:
<221> NAME/KEY: MOD_RES
<222> LOCATION: (9)..(9)
<223> OTHER INFORMATION: L, V or I

<400> SEQUENCE: 10

Xaa Xaa Xaa Xaa Xaa Xaa Xaa Xaa Xaa
1               5

<210> SEQ ID NO 11
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
```

```
<220> FEATURE:
<221> NAME/KEY: MOD_RES
<222> LOCATION: (1)..(1)
<223> OTHER INFORMATION: F, L or M
<220> FEATURE:
<221> NAME/KEY: MOD_RES
<222> LOCATION: (2)..(2)
<223> OTHER INFORMATION: Any amino acid
<220> FEATURE:
<221> NAME/KEY: MOD_RES
<222> LOCATION: (3)..(3)
<223> OTHER INFORMATION: Any amino acid
<220> FEATURE:
<221> NAME/KEY: MOD_RES
<222> LOCATION: (4)..(4)
<223> OTHER INFORMATION: Any amino acid
<220> FEATURE:
<221> NAME/KEY: MOD_RES
<222> LOCATION: (5)..(5)
<223> OTHER INFORMATION: F or L
<220> FEATURE:
<221> NAME/KEY: MOD_RES
<222> LOCATION: (6)..(6)
<223> OTHER INFORMATION: Any amino acid
<220> FEATURE:
<221> NAME/KEY: MOD_RES
<222> LOCATION: (7)..(7)
<223> OTHER INFORMATION: Any amino acid
<220> FEATURE:
<221> NAME/KEY: MOD_RES
<222> LOCATION: (8)..(8)
<223> OTHER INFORMATION: I or A

<400> SEQUENCE: 11

Xaa Xaa Xaa Xaa Xaa Xaa Xaa Xaa
1               5

<210> SEQ ID NO 12
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: F, L, Y, M, I, V or A
<220> FEATURE:
<221> NAME/KEY: MOD_RES
<222> LOCATION: (2)..(2)
<223> OTHER INFORMATION: Any amino acid
<220> FEATURE:
<221> NAME/KEY: MOD_RES
<222> LOCATION: (3)..(3)
<223> OTHER INFORMATION: Any amino acid
<220> FEATURE:
<221> NAME/KEY: MOD_RES
<222> LOCATION: (4)..(4)
<223> OTHER INFORMATION: Any amino acid
<220> FEATURE:
<221> NAME/KEY: MOD_RES
<222> LOCATION: (5)..(5)
<223> OTHER INFORMATION: Any amino acid
<220> FEATURE:
<221> NAME/KEY: MOD_RES
<222> LOCATION: (6)..(6)
<223> OTHER INFORMATION: Any amino acid
<220> FEATURE:
<221> NAME/KEY: MOD_RES
<222> LOCATION: (7)..(7)
<223> OTHER INFORMATION: F, L, Y, M, V, I or A
<220> FEATURE:
<221> NAME/KEY: MOD_RES
<222> LOCATION: (8)..(8)
<223> OTHER INFORMATION: Any amino acid
<220> FEATURE:
```

```
<221> NAME/KEY: MOD_RES
<222> LOCATION: (9)..(9)
<223> OTHER INFORMATION: Any amino acid
<220> FEATURE:
<221> NAME/KEY: MOD_RES
<222> LOCATION: (10)..(10)
<223> OTHER INFORMATION: V, Y, I, A or L

<400> SEQUENCE: 12

Xaa Xaa Xaa Xaa Xaa Xaa Xaa Xaa Xaa Xaa
1               5                   10

<210> SEQ ID NO 13
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: F, L, Y, M, I, V or A
<220> FEATURE:
<221> NAME/KEY: MOD_RES
<222> LOCATION: (2)..(2)
<223> OTHER INFORMATION: Any amino acid
<220> FEATURE:
<221> NAME/KEY: MOD_RES
<222> LOCATION: (3)..(3)
<223> OTHER INFORMATION: Any amino acid
<220> FEATURE:
<221> NAME/KEY: MOD_RES
<222> LOCATION: (4)..(4)
<223> OTHER INFORMATION: Any amino acid
<220> FEATURE:
<221> NAME/KEY: MOD_RES
<222> LOCATION: (5)..(5)
<223> OTHER INFORMATION: Any amino acid
<220> FEATURE:
<221> NAME/KEY: MOD_RES
<222> LOCATION: (6)..(6)
<223> OTHER INFORMATION: Any amino acid
<220> FEATURE:
<221> NAME/KEY: MOD_RES
<222> LOCATION: (7)..(7)
<223> OTHER INFORMATION: F, L, Y, M, V, I or A
<220> FEATURE:
<221> NAME/KEY: MOD_RES
<222> LOCATION: (8)..(8)
<223> OTHER INFORMATION: Any amino acid
<220> FEATURE:
<221> NAME/KEY: MOD_RES
<222> LOCATION: (9)..(9)
<223> OTHER INFORMATION: Any amino acid
<220> FEATURE:
<221> NAME/KEY: MOD_RES
<222> LOCATION: (10)..(10)
<223> OTHER INFORMATION: V, Y, I, A or L

<400> SEQUENCE: 13

Xaa Xaa Xaa Xaa Xaa Xaa Xaa Xaa Xaa Xaa
1               5                   10

<210> SEQ ID NO 14
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: R or K
```

```
<220> FEATURE:
<221> NAME/KEY: MOD_RES
<222> LOCATION: (2)..(2)
<223> OTHER INFORMATION: Any amino acid
<220> FEATURE:
<221> NAME/KEY: MOD_RES
<222> LOCATION: (3)..(3)
<223> OTHER INFORMATION: Any amino acid
<220> FEATURE:
<221> NAME/KEY: MOD_RES
<222> LOCATION: (4)..(4)
<223> OTHER INFORMATION: Any amino acid
<220> FEATURE:
<221> NAME/KEY: MOD_RES
<222> LOCATION: (5)..(5)
<223> OTHER INFORMATION: Any amino acid
<220> FEATURE:
<221> NAME/KEY: MOD_RES
<222> LOCATION: (6)..(6)
<223> OTHER INFORMATION: A, G or L
<220> FEATURE:
<221> NAME/KEY: MOD_RES
<222> LOCATION: (7)..(7)
<223> OTHER INFORMATION: Any amino acid
<220> FEATURE:
<221> NAME/KEY: MOD_RES
<222> LOCATION: (8)..(8)
<223> OTHER INFORMATION: Any amino acid
<220> FEATURE:
<221> NAME/KEY: MOD_RES
<222> LOCATION: (9)..(9)
<223> OTHER INFORMATION: L or V

<400> SEQUENCE: 14

Xaa Xaa Xaa Xaa Xaa Xaa Xaa Xaa Xaa
1               5

<210> SEQ ID NO 15
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Any amino acid
<220> FEATURE:
<221> NAME/KEY: MOD_RES
<222> LOCATION: (3)..(3)
<223> OTHER INFORMATION: Any amino acid
<220> FEATURE:
<221> NAME/KEY: MOD_RES
<222> LOCATION: (4)..(4)
<223> OTHER INFORMATION: Any amino acid
<220> FEATURE:
<221> NAME/KEY: MOD_RES
<222> LOCATION: (5)..(5)
<223> OTHER INFORMATION: Any amino acid
<220> FEATURE:
<221> NAME/KEY: MOD_RES
<222> LOCATION: (6)..(6)
<223> OTHER INFORMATION: Any amino acid
<220> FEATURE:
<221> NAME/KEY: MOD_RES
<222> LOCATION: (7)..(7)
<223> OTHER INFORMATION: Any amino acid
<220> FEATURE:
<221> NAME/KEY: MOD_RES
<222> LOCATION: (8)..(8)
<223> OTHER INFORMATION: Any amino acid
<220> FEATURE:
<221> NAME/KEY: MOD_RES
<222> LOCATION: (9)..(9)
<223> OTHER INFORMATION: Any amino acid
```

```
<400> SEQUENCE: 15

Xaa Arg Xaa Xaa Xaa Xaa Xaa Xaa Xaa
1               5

<210> SEQ ID NO 16
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Any amino acid
<220> FEATURE:
<221> NAME/KEY: MOD_RES
<222> LOCATION: (3)..(3)
<223> OTHER INFORMATION: Any amino acid
<220> FEATURE:
<221> NAME/KEY: MOD_RES
<222> LOCATION: (4)..(4)
<223> OTHER INFORMATION: Any amino acid
<220> FEATURE:
<221> NAME/KEY: MOD_RES
<222> LOCATION: (5)..(5)
<223> OTHER INFORMATION: Y, F or W

<400> SEQUENCE: 16

Leu Xaa Xaa Xaa Xaa
1               5

<210> SEQ ID NO 17
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Any amino acid
<220> FEATURE:
<221> NAME/KEY: MOD_RES
<222> LOCATION: (2)..(2)
<223> OTHER INFORMATION: Any amino acid
<220> FEATURE:
<221> NAME/KEY: MOD_RES
<222> LOCATION: (3)..(3)
<223> OTHER INFORMATION: Any amino acid
<220> FEATURE:
<221> NAME/KEY: MOD_RES
<222> LOCATION: (4)..(4)
<223> OTHER INFORMATION: Any amino acid
<220> FEATURE:
<221> NAME/KEY: MOD_RES
<222> LOCATION: (5)..(5)
<223> OTHER INFORMATION: Any amino acid
<220> FEATURE:
<221> NAME/KEY: MOD_RES
<222> LOCATION: (6)..(6)
<223> OTHER INFORMATION: L, I, V, A, P, S or T
<220> FEATURE:
<221> NAME/KEY: MOD_RES
<222> LOCATION: (7)..(7)
<223> OTHER INFORMATION: Any amino acid
<220> FEATURE:
<221> NAME/KEY: MOD_RES
<222> LOCATION: (8)..(8)
<223> OTHER INFORMATION: Any amino acid
<220> FEATURE:
<221> NAME/KEY: MOD_RES
<222> LOCATION: (9)..(9)
<223> OTHER INFORMATION: A, G, S, T, L, I, V or P
```

```
<400> SEQUENCE: 17

Xaa Xaa Xaa Xaa Xaa Xaa Xaa Xaa Xaa
1               5

<210> SEQ ID NO 18
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Any amino acid
<220> FEATURE:
<221> NAME/KEY: MOD_RES
<222> LOCATION: (2)..(2)
<223> OTHER INFORMATION: Any amino acid
<220> FEATURE:
<221> NAME/KEY: MOD_RES
<222> LOCATION: (3)..(3)
<223> OTHER INFORMATION: A, G, S or T
<220> FEATURE:
<221> NAME/KEY: MOD_RES
<222> LOCATION: (4)..(4)
<223> OTHER INFORMATION: Any amino acid
<220> FEATURE:
<221> NAME/KEY: MOD_RES
<222> LOCATION: (5)..(5)
<223> OTHER INFORMATION: A, V, L or I

<400> SEQUENCE: 18

Xaa Xaa Xaa Xaa Xaa
1               5

<210> SEQ ID NO 19
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: D, E or W
<220> FEATURE:
<221> NAME/KEY: MOD_RES
<222> LOCATION: (2)..(2)
<223> OTHER INFORMATION: Any amino acid
<220> FEATURE:
<221> NAME/KEY: MOD_RES
<222> LOCATION: (3)..(3)
<223> OTHER INFORMATION: Any amino acid
<220> FEATURE:
<221> NAME/KEY: MOD_RES
<222> LOCATION: (4)..(4)
<223> OTHER INFORMATION: A, G, S or T
<220> FEATURE:
<221> NAME/KEY: MOD_RES
<222> LOCATION: (5)..(5)
<223> OTHER INFORMATION: Any amino acid
<220> FEATURE:
<221> NAME/KEY: MOD_RES
<222> LOCATION: (6)..(6)
<223> OTHER INFORMATION: A, C, L or M

<400> SEQUENCE: 19

Xaa Xaa Xaa Xaa Xaa Xaa
1               5
```

```
<210> SEQ ID NO 20
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: R or K
<220> FEATURE:
<221> NAME/KEY: MOD_RES
<222> LOCATION: (2)..(2)
<223> OTHER INFORMATION: Any amino acid
<220> FEATURE:
<221> NAME/KEY: MOD_RES
<222> LOCATION: (3)..(3)
<223> OTHER INFORMATION: Any amino acid
<220> FEATURE:
<221> NAME/KEY: MOD_RES
<222> LOCATION: (4)..(4)
<223> OTHER INFORMATION: Any amino acid
<220> FEATURE:
<221> NAME/KEY: MOD_RES
<222> LOCATION: (5)..(5)
<223> OTHER INFORMATION: A or G
<220> FEATURE:
<221> NAME/KEY: MOD_RES
<222> LOCATION: (6)..(6)
<223> OTHER INFORMATION: Any amino acid
<220> FEATURE:
<221> NAME/KEY: MOD_RES
<222> LOCATION: (7)..(7)
<223> OTHER INFORMATION: Any amino acid
<220> FEATURE:
<221> NAME/KEY: MOD_RES
<222> LOCATION: (8)..(8)
<223> OTHER INFORMATION: N, E or D

<400> SEQUENCE: 20

Xaa Xaa Xaa Xaa Xaa Xaa Xaa Xaa
1               5

<210> SEQ ID NO 21
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: T, S or W
<220> FEATURE:
<221> NAME/KEY: MOD_RES
<222> LOCATION: (2)..(2)
<223> OTHER INFORMATION: Any amino acid
<220> FEATURE:
<221> NAME/KEY: MOD_RES
<222> LOCATION: (3)..(3)
<223> OTHER INFORMATION: Any amino acid
<220> FEATURE:
<221> NAME/KEY: MOD_RES
<222> LOCATION: (4)..(4)
<223> OTHER INFORMATION: Any amino acid
<220> FEATURE:
<221> NAME/KEY: MOD_RES
<222> LOCATION: (5)..(5)
<223> OTHER INFORMATION: Any amino acid
<220> FEATURE:
<221> NAME/KEY: MOD_RES
<222> LOCATION: (6)..(6)
<223> OTHER INFORMATION: Any amino acid
<220> FEATURE:
<221> NAME/KEY: MOD_RES
```

```
<222> LOCATION: (7)..(7)
<223> OTHER INFORMATION: Any amino acid
<220> FEATURE:
<221> NAME/KEY: MOD_RES
<222> LOCATION: (8)..(8)
<223> OTHER INFORMATION: Any amino acid
<220> FEATURE:
<221> NAME/KEY: MOD_RES
<222> LOCATION: (9)..(9)
<223> OTHER INFORMATION: R or E

<400> SEQUENCE: 21

Xaa Xaa Xaa Xaa Xaa Xaa Xaa Xaa Xaa
1               5

<210> SEQ ID NO 22
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: F, W, Y, I, L or V
<220> FEATURE:
<221> NAME/KEY: MOD_RES
<222> LOCATION: (2)..(2)
<223> OTHER INFORMATION: Any amino acid
<220> FEATURE:
<221> NAME/KEY: MOD_RES
<222> LOCATION: (3)..(3)
<223> OTHER INFORMATION: Any amino acid
<220> FEATURE:
<221> NAME/KEY: MOD_RES
<222> LOCATION: (4)..(4)
<223> OTHER INFORMATION: D, E, L, V, I or H
<220> FEATURE:
<221> NAME/KEY: MOD_RES
<222> LOCATION: (5)..(5)
<223> OTHER INFORMATION: Any amino acid
<220> FEATURE:
<221> NAME/KEY: MOD_RES
<222> LOCATION: (6)..(6)
<223> OTHER INFORMATION: P, D, E or H
<220> FEATURE:
<221> NAME/KEY: MOD_RES
<222> LOCATION: (7)..(7)
<223> OTHER INFORMATION: E or D
<220> FEATURE:
<221> NAME/KEY: MOD_RES
<222> LOCATION: (8)..(8)
<223> OTHER INFORMATION: Any amino acid
<220> FEATURE:
<221> NAME/KEY: MOD_RES
<222> LOCATION: (9)..(9)
<223> OTHER INFORMATION: F, Y, W, V, I, L or M

<400> SEQUENCE: 22

Xaa Xaa Xaa Xaa Xaa Xaa Xaa Xaa Xaa
1               5

<210> SEQ ID NO 23
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: F, W, Y, I, L or V
<220> FEATURE:
```

```
<221> NAME/KEY: MOD_RES
<222> LOCATION: (2)..(2)
<223> OTHER INFORMATION: Any amino acid
<220> FEATURE:
<221> NAME/KEY: MOD_RES
<222> LOCATION: (3)..(3)
<223> OTHER INFORMATION: Any amino acid
<220> FEATURE:
<221> NAME/KEY: MOD_RES
<222> LOCATION: (4)..(4)
<223> OTHER INFORMATION: D, E, L, V, I or H
<220> FEATURE:
<221> NAME/KEY: MOD_RES
<222> LOCATION: (5)..(5)
<223> OTHER INFORMATION: Any amino acid
<220> FEATURE:
<221> NAME/KEY: MOD_RES
<222> LOCATION: (6)..(6)
<223> OTHER INFORMATION: P, D, E, H, P or A
<220> FEATURE:
<221> NAME/KEY: MOD_RES
<222> LOCATION: (7)..(7)
<223> OTHER INFORMATION: D or E
<220> FEATURE:
<221> NAME/KEY: MOD_RES
<222> LOCATION: (8)..(8)
<223> OTHER INFORMATION: Any amino acid
<220> FEATURE:
<221> NAME/KEY: MOD_RES
<222> LOCATION: (9)..(9)
<223> OTHER INFORMATION: F, Y, W, V, I, L or M

<400> SEQUENCE: 23

Xaa Xaa Xaa Xaa Xaa Xaa Xaa Xaa Xaa
1               5

<210> SEQ ID NO 24
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: F, Y, I, M, L or V
<220> FEATURE:
<221> NAME/KEY: MOD_RES
<222> LOCATION: (2)..(2)
<223> OTHER INFORMATION: Any amino acid
<220> FEATURE:
<221> NAME/KEY: MOD_RES
<222> LOCATION: (3)..(3)
<223> OTHER INFORMATION: Any amino acid
<220> FEATURE:
<221> NAME/KEY: MOD_RES
<222> LOCATION: (4)..(4)
<223> OTHER INFORMATION: Any amino acid
<220> FEATURE:
<221> NAME/KEY: MOD_RES
<222> LOCATION: (5)..(5)
<223> OTHER INFORMATION: V, L, I, M or Y
<220> FEATURE:
<221> NAME/KEY: MOD_RES
<222> LOCATION: (6)..(6)
<223> OTHER INFORMATION: Any amino acid
<220> FEATURE:
<221> NAME/KEY: MOD_RES
<222> LOCATION: (7)..(7)
<223> OTHER INFORMATION: Y, F, M, L, V or I

<400> SEQUENCE: 24

Xaa Xaa Xaa Xaa Xaa Xaa Xaa
1               5
```

```
<210> SEQ ID NO 25
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: W, Y, A, V or M
<220> FEATURE:
<221> NAME/KEY: MOD_RES
<222> LOCATION: (2)..(2)
<223> OTHER INFORMATION: Any amino acid
<220> FEATURE:
<221> NAME/KEY: MOD_RES
<222> LOCATION: (3)..(3)
<223> OTHER INFORMATION: Any amino acid
<220> FEATURE:
<221> NAME/KEY: MOD_RES
<222> LOCATION: (5)..(5)
<223> OTHER INFORMATION: Any amino acid
<220> FEATURE:
<221> NAME/KEY: MOD_RES
<222> LOCATION: (6)..(6)
<223> OTHER INFORMATION: A, I, V, T or S
<220> FEATURE:
<221> NAME/KEY: MOD_RES
<222> LOCATION: (7)..(7)
<223> OTHER INFORMATION: Any amino acid
<220> FEATURE:
<221> NAME/KEY: MOD_RES
<222> LOCATION: (8)..(8)
<223> OTHER INFORMATION: Any amino acid
<220> FEATURE:
<221> NAME/KEY: MOD_RES
<222> LOCATION: (9)..(9)
<223> OTHER INFORMATION: Any amino acid
<220> FEATURE:
<221> NAME/KEY: MOD_RES
<222> LOCATION: (10)..(10)
<223> OTHER INFORMATION: Q or N

<400> SEQUENCE: 25

Xaa Xaa Xaa Ala Xaa Xaa Xaa Xaa Xaa Xaa
1               5                   10

<210> SEQ ID NO 26
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: A, F, C, I, L, M, N, Q, S, T, V, W, Y, D or E
<220> FEATURE:
<221> NAME/KEY: MOD_RES
<222> LOCATION: (2)..(2)
<223> OTHER INFORMATION: Any amino acid
<220> FEATURE:
<221> NAME/KEY: MOD_RES
<222> LOCATION: (3)..(3)
<223> OTHER INFORMATION: A, F, G, I, L, M, N, Q, S, T, W, Y, C, D or E
<220> FEATURE:
<221> NAME/KEY: MOD_RES
<222> LOCATION: (4)..(4)
<223> OTHER INFORMATION: A, F, G, I, L, M, N, Q, S, T, W or Y
<220> FEATURE:
<221> NAME/KEY: MOD_RES
<222> LOCATION: (5)..(5)
<223> OTHER INFORMATION: Any amino acid
<220> FEATURE:
```

```
<221> NAME/KEY: MOD_RES
<222> LOCATION: (6)..(6)
<223> OTHER INFORMATION: L, I, V, A, P, S or T
<220> FEATURE:
<221> NAME/KEY: MOD_RES
<222> LOCATION: (7)..(7)
<223> OTHER INFORMATION: Any amino acid
<220> FEATURE:
<221> NAME/KEY: MOD_RES
<222> LOCATION: (8)..(8)
<223> OTHER INFORMATION: Any amino acid
<220> FEATURE:
<221> NAME/KEY: MOD_RES
<222> LOCATION: (9)..(9)
<223> OTHER INFORMATION: A, S, T, G, L, I, V or P

<400> SEQUENCE: 26

Xaa Xaa Xaa Xaa Xaa Xaa Xaa Xaa Xaa
1               5

<210> SEQ ID NO 27
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Y, F, W, L, I, M, V or A
<220> FEATURE:
<221> NAME/KEY: MOD_RES
<222> LOCATION: (2)..(2)
<223> OTHER INFORMATION: Any amino acid
<220> FEATURE:
<221> NAME/KEY: MOD_RES
<222> LOCATION: (3)..(3)
<223> OTHER INFORMATION: Any amino acid
<220> FEATURE:
<221> NAME/KEY: MOD_RES
<222> LOCATION: (4)..(4)
<223> OTHER INFORMATION: L, M, A, I, V or N
<220> FEATURE:
<221> NAME/KEY: MOD_RES
<222> LOCATION: (5)..(5)
<223> OTHER INFORMATION: Any amino acid
<220> FEATURE:
<221> NAME/KEY: MOD_RES
<222> LOCATION: (6)..(6)
<223> OTHER INFORMATION: A, G, S, T, C or P
<220> FEATURE:
<221> NAME/KEY: MOD_RES
<222> LOCATION: (7)..(7)
<223> OTHER INFORMATION: Any amino acid
<220> FEATURE:
<221> NAME/KEY: MOD_RES
<222> LOCATION: (8)..(8)
<223> OTHER INFORMATION: Any amino acid
<220> FEATURE:
<221> NAME/KEY: MOD_RES
<222> LOCATION: (9)..(9)
<223> OTHER INFORMATION: L, A, I, V, N, F, Y, M or W

<400> SEQUENCE: 27

Xaa Xaa Xaa Xaa Xaa Xaa Xaa Xaa Xaa
1               5

<210> SEQ ID NO 28
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
```

```
<220> FEATURE:
<221> NAME/KEY: MOD_RES
<222> LOCATION: (1)..(1)
<223> OTHER INFORMATION: Y, V, L, F, I, A, M or W
<220> FEATURE:
<221> NAME/KEY: MOD_RES
<222> LOCATION: (2)..(2)
<223> OTHER INFORMATION: Any amino acid
<220> FEATURE:
<221> NAME/KEY: MOD_RES
<222> LOCATION: (3)..(3)
<223> OTHER INFORMATION: Any amino acid
<220> FEATURE:
<221> NAME/KEY: MOD_RES
<222> LOCATION: (4)..(4)
<223> OTHER INFORMATION: L, A, I, V, M, N or Q
<220> FEATURE:
<221> NAME/KEY: MOD_RES
<222> LOCATION: (5)..(5)
<223> OTHER INFORMATION: Any amino acid
<220> FEATURE:
<221> NAME/KEY: MOD_RES
<222> LOCATION: (6)..(6)
<223> OTHER INFORMATION: A, G, S, T, C or P
<220> FEATURE:
<221> NAME/KEY: MOD_RES
<222> LOCATION: (7)..(7)
<223> OTHER INFORMATION: Any amino acid
<220> FEATURE:
<221> NAME/KEY: MOD_RES
<222> LOCATION: (8)..(8)
<223> OTHER INFORMATION: Any amino acid
<220> FEATURE:
<221> NAME/KEY: MOD_RES
<222> LOCATION: (9)..(9)
<223> OTHER INFORMATION: L, A, I, V, N, F or Y

<400> SEQUENCE: 28

Xaa Xaa Xaa Xaa Xaa Xaa Xaa Xaa Xaa
1               5

<210> SEQ ID NO 29
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: I, L, V or M
<220> FEATURE:
<221> NAME/KEY: MOD_RES
<222> LOCATION: (2)..(2)
<223> OTHER INFORMATION: Any amino acid
<220> FEATURE:
<221> NAME/KEY: MOD_RES
<222> LOCATION: (3)..(3)
<223> OTHER INFORMATION: Any amino acid
<220> FEATURE:
<221> NAME/KEY: MOD_RES
<222> LOCATION: (4)..(4)
<223> OTHER INFORMATION: A, L or M
<220> FEATURE:
<221> NAME/KEY: MOD_RES
<222> LOCATION: (5)..(5)
<223> OTHER INFORMATION: Any amino acid
<220> FEATURE:
<221> NAME/KEY: MOD_RES
<222> LOCATION: (6)..(6)
<223> OTHER INFORMATION: A, G, S, T, C or P
<220> FEATURE:
<221> NAME/KEY: MOD_RES
<222> LOCATION: (7)..(7)
<223> OTHER INFORMATION: Any amino acid
<220> FEATURE:
```

```
<221> NAME/KEY: MOD_RES
<222> LOCATION: (8)..(8)
<223> OTHER INFORMATION: Any amino acid
<220> FEATURE:
<221> NAME/KEY: MOD_RES
<222> LOCATION: (9)..(9)
<223> OTHER INFORMATION: I, L, A, M, Y or W

<400> SEQUENCE: 29

Xaa Xaa Xaa Xaa Xaa Xaa Xaa Xaa Xaa
1               5

<210> SEQ ID NO 30
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: I, L, V or M
<220> FEATURE:
<221> NAME/KEY: MOD_RES
<222> LOCATION: (2)..(2)
<223> OTHER INFORMATION: Any amino acid
<220> FEATURE:
<221> NAME/KEY: MOD_RES
<222> LOCATION: (3)..(3)
<223> OTHER INFORMATION: Any amino acid
<220> FEATURE:
<221> NAME/KEY: MOD_RES
<222> LOCATION: (4)..(4)
<223> OTHER INFORMATION: A, L or M
<220> FEATURE:
<221> NAME/KEY: MOD_RES
<222> LOCATION: (5)..(5)
<223> OTHER INFORMATION: Any amino acid
<220> FEATURE:
<221> NAME/KEY: MOD_RES
<222> LOCATION: (6)..(6)
<223> OTHER INFORMATION: A, G, S, T or P
<220> FEATURE:
<221> NAME/KEY: MOD_RES
<222> LOCATION: (7)..(7)
<223> OTHER INFORMATION: Any amino acid
<220> FEATURE:
<221> NAME/KEY: MOD_RES
<222> LOCATION: (8)..(8)
<223> OTHER INFORMATION: Any amino acid
<220> FEATURE:
<221> NAME/KEY: MOD_RES
<222> LOCATION: (9)..(9)
<223> OTHER INFORMATION: I, L, A, M, Y or W

<400> SEQUENCE: 30

Xaa Xaa Xaa Xaa Xaa Xaa Xaa Xaa Xaa
1               5

<210> SEQ ID NO 31
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: L, I, F, M or V
<220> FEATURE:
<221> NAME/KEY: MOD_RES
<222> LOCATION: (2)..(2)
<223> OTHER INFORMATION: Any amino acid
```

```
<220> FEATURE:
<221> NAME/KEY: MOD_RES
<222> LOCATION: (3)..(3)
<223> OTHER INFORMATION: Any amino acid
<220> FEATURE:
<221> NAME/KEY: MOD_RES
<222> LOCATION: (5)..(5)
<223> OTHER INFORMATION: Any amino acid
<220> FEATURE:
<221> NAME/KEY: MOD_RES
<222> LOCATION: (6)..(6)
<223> OTHER INFORMATION: K, R, E, Q or N
<220> FEATURE:
<221> NAME/KEY: MOD_RES
<222> LOCATION: (7)..(7)
<223> OTHER INFORMATION: Any amino acid
<220> FEATURE:
<221> NAME/KEY: MOD_RES
<222> LOCATION: (9)..(9)
<223> OTHER INFORMATION: Y, L or F

<400> SEQUENCE: 31

Xaa Xaa Xaa Asp Xaa Xaa Xaa Leu Xaa
1               5

<210> SEQ ID NO 32
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: L, I, F, M or V
<220> FEATURE:
<221> NAME/KEY: MOD_RES
<222> LOCATION: (2)..(2)
<223> OTHER INFORMATION: Any amino acid
<220> FEATURE:
<221> NAME/KEY: MOD_RES
<222> LOCATION: (3)..(3)
<223> OTHER INFORMATION: Any amino acid
<220> FEATURE:
<221> NAME/KEY: MOD_RES
<222> LOCATION: (5)..(5)
<223> OTHER INFORMATION: Any amino acid
<220> FEATURE:
<221> NAME/KEY: MOD_RES
<222> LOCATION: (6)..(6)
<223> OTHER INFORMATION: K, R, E, Q or N
<220> FEATURE:
<221> NAME/KEY: MOD_RES
<222> LOCATION: (7)..(7)
<223> OTHER INFORMATION: Any amino acid
<220> FEATURE:
<221> NAME/KEY: MOD_RES
<222> LOCATION: (8)..(8)
<223> OTHER INFORMATION: Any amino acid
<220> FEATURE:
<221> NAME/KEY: MOD_RES
<222> LOCATION: (9)..(9)
<223> OTHER INFORMATION: Y, L or F

<400> SEQUENCE: 32

Xaa Xaa Xaa Asp Xaa Xaa Xaa Xaa Xaa
1               5

<210> SEQ ID NO 33
<211> LENGTH: 4
<212> TYPE: PRT
<213> ORGANISM: Artificial Sequence
<220> FEATURE:
<223> OTHER INFORMATION: Description of Artificial Sequence: Synthetic
```

```
                peptide
<220> FEATURE:
<221> NAME/KEY: MOD_RES
<222> LOCATION: (1)..(1)
<223> OTHER INFORMATION: F, I, L, V or Y
<220> FEATURE:
<221> NAME/KEY: MOD_RES
<222> LOCATION: (2)..(2)
<223> OTHER INFORMATION: Any amino acid
<220> FEATURE:
<221> NAME/KEY: MOD_RES
<222> LOCATION: (3)..(3)
<223> OTHER INFORMATION: Any amino acid
<220> FEATURE:
<221> NAME/KEY: MOD_RES
<222> LOCATION: (4)..(4)
<223> OTHER INFORMATION: D, N, Q or T

<400> SEQUENCE: 33

Xaa Xaa Xaa Xaa
1

<210> SEQ ID NO 34
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: F, L or V
<220> FEATURE:
<221> NAME/KEY: MOD_RES
<222> LOCATION: (2)..(2)
<223> OTHER INFORMATION: Any amino acid
<220> FEATURE:
<221> NAME/KEY: MOD_RES
<222> LOCATION: (3)..(3)
<223> OTHER INFORMATION: Any amino acid
<220> FEATURE:
<221> NAME/KEY: MOD_RES
<222> LOCATION: (4)..(4)
<223> OTHER INFORMATION: Any amino acid
<220> FEATURE:
<221> NAME/KEY: MOD_RES
<222> LOCATION: (5)..(5)
<223> OTHER INFORMATION: Any amino acid
<220> FEATURE:
<221> NAME/KEY: MOD_RES
<222> LOCATION: (6)..(6)
<223> OTHER INFORMATION: Any amino acid
<220> FEATURE:
<221> NAME/KEY: MOD_RES
<222> LOCATION: (7)..(7)
<223> OTHER INFORMATION: Any amino acid
<220> FEATURE:
<221> NAME/KEY: MOD_RES
<222> LOCATION: (8)..(8)
<223> OTHER INFORMATION: Any amino acid
<220> FEATURE:
<221> NAME/KEY: MOD_RES
<222> LOCATION: (9)..(9)
<223> OTHER INFORMATION: N, Q, S or T

<400> SEQUENCE: 34

Xaa Xaa Xaa Xaa Xaa Xaa Xaa Xaa Xaa
1               5

<210> SEQ ID NO 35
<211> LENGTH: 9
<212> TYPE: PRT
<213> ORGANISM: Artificial Sequence
<220> FEATURE:
```

<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: F, Y, W, I, L, V or M
<220> FEATURE:
<221> NAME/KEY: MOD_RES
<222> LOCATION: (2)..(2)
<223> OTHER INFORMATION: Any amino acid
<220> FEATURE:
<221> NAME/KEY: MOD_RES
<222> LOCATION: (3)..(3)
<223> OTHER INFORMATION: Any amino acid
<220> FEATURE:
<221> NAME/KEY: MOD_RES
<222> LOCATION: (4)..(4)
<223> OTHER INFORMATION: F, W, I, L, V, A, D or E
<220> FEATURE:
<221> NAME/KEY: MOD_RES
<222> LOCATION: (5)..(5)
<223> OTHER INFORMATION: Any amino acid
<220> FEATURE:
<221> NAME/KEY: MOD_RES
<222> LOCATION: (6)..(6)
<223> OTHER INFORMATION: N, S, T, Q, H or R
<220> FEATURE:
<221> NAME/KEY: MOD_RES
<222> LOCATION: (7)..(7)
<223> OTHER INFORMATION: Any amino acid
<220> FEATURE:
<221> NAME/KEY: MOD_RES
<222> LOCATION: (8)..(8)
<223> OTHER INFORMATION: Any amino acid

<400> SEQUENCE: 35

Xaa Xaa Xaa Xaa Xaa Xaa Xaa Xaa Lys
1               5

<210> SEQ ID NO 36
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: F, Y or W
<220> FEATURE:
<221> NAME/KEY: MOD_RES
<222> LOCATION: (2)..(2)
<223> OTHER INFORMATION: Any amino acid
<220> FEATURE:
<221> NAME/KEY: MOD_RES
<222> LOCATION: (3)..(3)
<223> OTHER INFORMATION: Any amino acid
<220> FEATURE:
<221> NAME/KEY: MOD_RES
<222> LOCATION: (4)..(4)
<223> OTHER INFORMATION: Any amino acid
<220> FEATURE:
<221> NAME/KEY: MOD_RES
<222> LOCATION: (5)..(5)
<223> OTHER INFORMATION: Any amino acid
<220> FEATURE:
<221> NAME/KEY: MOD_RES
<222> LOCATION: (6)..(6)
<223> OTHER INFORMATION: Any amino acid
<220> FEATURE:
<221> NAME/KEY: MOD_RES
<222> LOCATION: (7)..(7)
<223> OTHER INFORMATION: Any amino acid
<220> FEATURE:
<221> NAME/KEY: MOD_RES
<222> LOCATION: (8)..(8)

```
<223> OTHER INFORMATION: Any amino acid
<220> FEATURE:
<221> NAME/KEY: MOD_RES
<222> LOCATION: (9)..(9)
<223> OTHER INFORMATION: S or T

<400> SEQUENCE: 36

Xaa Xaa Xaa Xaa Xaa Xaa Xaa Xaa Xaa
1               5

<210> SEQ ID NO 37
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: F, Y, W, I, L, V or M
<220> FEATURE:
<221> NAME/KEY: MOD_RES
<222> LOCATION: (2)..(2)
<223> OTHER INFORMATION: Any amino acid
<220> FEATURE:
<221> NAME/KEY: MOD_RES
<222> LOCATION: (3)..(3)
<223> OTHER INFORMATION: Any amino acid
<220> FEATURE:
<221> NAME/KEY: MOD_RES
<222> LOCATION: (4)..(4)
<223> OTHER INFORMATION: P, W, I, L, V, A, D or E
<220> FEATURE:
<221> NAME/KEY: MOD_RES
<222> LOCATION: (5)..(5)
<223> OTHER INFORMATION: Any amino acid
<220> FEATURE:
<221> NAME/KEY: MOD_RES
<222> LOCATION: (6)..(6)
<223> OTHER INFORMATION: N, S, T, Q, H or R
<220> FEATURE:
<221> NAME/KEY: MOD_RES
<222> LOCATION: (7)..(7)
<223> OTHER INFORMATION: D, E, H, K, N, Q, R, S, T, Y, A, C, I, L, M or
      V
<220> FEATURE:
<221> NAME/KEY: MOD_RES
<222> LOCATION: (8)..(8)
<223> OTHER INFORMATION: Any amino acid
<220> FEATURE:
<221> NAME/KEY: MOD_RES
<222> LOCATION: (9)..(9)
<223> OTHER INFORMATION: D, E, H, K, N, Q, R, S, T, Y, A, C, I, L, M or
      V

<400> SEQUENCE: 37

Xaa Xaa Xaa Xaa Xaa Xaa Xaa Xaa Xaa
1               5

<210> SEQ ID NO 38
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: V, I, L or M
<220> FEATURE:
<221> NAME/KEY: MOD_RES
<222> LOCATION: (2)..(2)
<223> OTHER INFORMATION: Any amino acid
```

```
<220> FEATURE:
<221> NAME/KEY: MOD_RES
<222> LOCATION: (3)..(3)
<223> OTHER INFORMATION: Any amino acid
<220> FEATURE:
<221> NAME/KEY: MOD_RES
<222> LOCATION: (4)..(4)
<223> OTHER INFORMATION: Y, F, W, I, L, M, R, N or H
<220> FEATURE:
<221> NAME/KEY: MOD_RES
<222> LOCATION: (5)..(5)
<223> OTHER INFORMATION: Any amino acid
<220> FEATURE:
<221> NAME/KEY: MOD_RES
<222> LOCATION: (6)..(6)
<223> OTHER INFORMATION: N, S, T, Q, H or K
<220> FEATURE:
<221> NAME/KEY: MOD_RES
<222> LOCATION: (7)..(7)
<223> OTHER INFORMATION: Any amino acid
<220> FEATURE:
<221> NAME/KEY: MOD_RES
<222> LOCATION: (8)..(8)
<223> OTHER INFORMATION: R, K, H, N, Q or P
<220> FEATURE:
<221> NAME/KEY: MOD_RES
<222> LOCATION: (9)..(9)
<223> OTHER INFORMATION: Any amino acid

<400> SEQUENCE: 38

Xaa Xaa Xaa Xaa Xaa Xaa Xaa Xaa Xaa His
1               5                   10

<210> SEQ ID NO 39
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: V, I, L or M
<220> FEATURE:
<221> NAME/KEY: MOD_RES
<222> LOCATION: (2)..(2)
<223> OTHER INFORMATION: Any amino acid
<220> FEATURE:
<221> NAME/KEY: MOD_RES
<222> LOCATION: (3)..(3)
<223> OTHER INFORMATION: Any amino acid
<220> FEATURE:
<221> NAME/KEY: MOD_RES
<222> LOCATION: (4)..(4)
<223> OTHER INFORMATION: Y, F, W, I, L, M, R or N
<220> FEATURE:
<221> NAME/KEY: MOD_RES
<222> LOCATION: (5)..(5)
<223> OTHER INFORMATION: Any amino acid
<220> FEATURE:
<221> NAME/KEY: MOD_RES
<222> LOCATION: (6)..(6)
<223> OTHER INFORMATION: N, Q, S, T or K
<220> FEATURE:
<221> NAME/KEY: MOD_RES
<222> LOCATION: (7)..(7)
<223> OTHER INFORMATION: R, K, H, N, Q or P
<220> FEATURE:
<221> NAME/KEY: MOD_RES
<222> LOCATION: (8)..(8)
<223> OTHER INFORMATION: Any amino acid
<220> FEATURE:
<221> NAME/KEY: MOD_RES
<222> LOCATION: (9)..(9)
<223> OTHER INFORMATION: D, E, H, L, N, Q, R, S, T, Y, C, I, L, M, V, H
      or A
```

```
<400> SEQUENCE: 39

Xaa Xaa Xaa Xaa Xaa Xaa Xaa Xaa Xaa
1               5

<210> SEQ ID NO 40
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: V, I, L or M
<220> FEATURE:
<221> NAME/KEY: MOD_RES
<222> LOCATION: (2)..(2)
<223> OTHER INFORMATION: Any amino acid
<220> FEATURE:
<221> NAME/KEY: MOD_RES
<222> LOCATION: (3)..(3)
<223> OTHER INFORMATION: Any amino acid
<220> FEATURE:
<221> NAME/KEY: MOD_RES
<222> LOCATION: (4)..(4)
<223> OTHER INFORMATION: F, Y, W, I, L, V, M, A, D or E
<220> FEATURE:
<221> NAME/KEY: MOD_RES
<222> LOCATION: (5)..(5)
<223> OTHER INFORMATION: Any amino acid
<220> FEATURE:
<221> NAME/KEY: MOD_RES
<222> LOCATION: (6)..(6)
<223> OTHER INFORMATION: N, T, S, Q or R
<220> FEATURE:
<221> NAME/KEY: MOD_RES
<222> LOCATION: (7)..(7)
<223> OTHER INFORMATION: Any amino acid
<220> FEATURE:
<221> NAME/KEY: MOD_RES
<222> LOCATION: (8)..(8)
<223> OTHER INFORMATION: Any amino acid

<400> SEQUENCE: 40

Xaa Xaa Xaa Xaa Xaa Xaa Xaa Xaa Lys
1               5

<210> SEQ ID NO 41
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: F, Y, W, V, I, L or M
<220> FEATURE:
<221> NAME/KEY: MOD_RES
<222> LOCATION: (2)..(2)
<223> OTHER INFORMATION: Any amino acid
<220> FEATURE:
<221> NAME/KEY: MOD_RES
<222> LOCATION: (3)..(3)
<223> OTHER INFORMATION: Any amino acid
<220> FEATURE:
<221> NAME/KEY: MOD_RES
<222> LOCATION: (4)..(4)
<223> OTHER INFORMATION: V, I, L, M, D or E
<220> FEATURE:
<221> NAME/KEY: MOD_RES
<222> LOCATION: (5)..(5)
```

```
<223> OTHER INFORMATION: Any amino acid
<220> FEATURE:
<221> NAME/KEY: MOD_RES
<222> LOCATION: (6)..(6)
<223> OTHER INFORMATION: N, S, T, Q, K or D
<220> FEATURE:
<221> NAME/KEY: MOD_RES
<222> LOCATION: (7)..(7)
<223> OTHER INFORMATION: Any amino acid
<220> FEATURE:
<221> NAME/KEY: MOD_RES
<222> LOCATION: (8)..(8)
<223> OTHER INFORMATION: Any amino acid
<220> FEATURE:
<221> NAME/KEY: MOD_RES
<222> LOCATION: (9)..(9)
<223> OTHER INFORMATION: Any amino acid
<220> FEATURE:
<221> NAME/KEY: MOD_RES
<222> LOCATION: (10)..(10)
<223> OTHER INFORMATION: D, E or Q

<400> SEQUENCE: 41

Xaa Xaa Xaa Xaa Xaa Xaa Xaa Xaa Xaa Xaa
1               5                   10

<210> SEQ ID NO 42
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Any amino acid
<220> FEATURE:
<221> NAME/KEY: MOD_RES
<222> LOCATION: (3)..(3)
<223> OTHER INFORMATION: Any amino acid
<220> FEATURE:
<221> NAME/KEY: MOD_RES
<222> LOCATION: (4)..(4)
<223> OTHER INFORMATION: Any amino acid
<220> FEATURE:
<221> NAME/KEY: MOD_RES
<222> LOCATION: (5)..(5)
<223> OTHER INFORMATION: Any amino acid
<220> FEATURE:
<221> NAME/KEY: MOD_RES
<222> LOCATION: (6)..(6)
<223> OTHER INFORMATION: V or T
<220> FEATURE:
<221> NAME/KEY: MOD_RES
<222> LOCATION: (7)..(7)
<223> OTHER INFORMATION: Any amino acid
<220> FEATURE:
<221> NAME/KEY: MOD_RES
<222> LOCATION: (8)..(8)
<223> OTHER INFORMATION: Any amino acid
<220> FEATURE:
<221> NAME/KEY: MOD_RES
<222> LOCATION: (9)..(9)
<223> OTHER INFORMATION: Any amino acid

<400> SEQUENCE: 42

Tyr Xaa Xaa Xaa Xaa Xaa Xaa Xaa Xaa Asp
1               5                   10

<210> SEQ ID NO 43
<211> LENGTH: 10
<212> TYPE: PRT
<213> ORGANISM: Artificial Sequence
<220> FEATURE:
```

-continued

```
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: F, Y or W
<220> FEATURE:
<221> NAME/KEY: MOD_RES
<222> LOCATION: (2)..(2)
<223> OTHER INFORMATION: Any amino acid
<220> FEATURE:
<221> NAME/KEY: MOD_RES
<222> LOCATION: (3)..(3)
<223> OTHER INFORMATION: Any amino acid
<220> FEATURE:
<221> NAME/KEY: MOD_RES
<222> LOCATION: (4)..(4)
<223> OTHER INFORMATION: A, V, T or K
<220> FEATURE:
<221> NAME/KEY: MOD_RES
<222> LOCATION: (5)..(5)
<223> OTHER INFORMATION: Any amino acid
<220> FEATURE:
<221> NAME/KEY: MOD_RES
<222> LOCATION: (6)..(6)
<223> OTHER INFORMATION: N, T, D or S
<220> FEATURE:
<221> NAME/KEY: MOD_RES
<222> LOCATION: (7)..(7)
<223> OTHER INFORMATION: Any amino acid
<220> FEATURE:
<221> NAME/KEY: MOD_RES
<222> LOCATION: (8)..(8)
<223> OTHER INFORMATION: Any amino acid
<220> FEATURE:
<221> NAME/KEY: MOD_RES
<222> LOCATION: (9)..(9)
<223> OTHER INFORMATION: Any amino acid
<220> FEATURE:
<221> NAME/KEY: MOD_RES
<222> LOCATION: (10)..(10)
<223> OTHER INFORMATION: Q or N

<400> SEQUENCE: 43

Xaa Xaa Xaa Xaa Xaa Xaa Xaa Xaa Xaa Xaa
1               5                   10

<210> SEQ ID NO 44
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: F, I, L, V or Y
<220> FEATURE:
<221> NAME/KEY: MOD_RES
<222> LOCATION: (2)..(2)
<223> OTHER INFORMATION: Any amino acid
<220> FEATURE:
<221> NAME/KEY: MOD_RES
<222> LOCATION: (3)..(3)
<223> OTHER INFORMATION: Any amino acid
<220> FEATURE:
<221> NAME/KEY: MOD_RES
<222> LOCATION: (4)..(4)
<223> OTHER INFORMATION: Any amino acid
<220> FEATURE:
<221> NAME/KEY: MOD_RES
<222> LOCATION: (5)..(5)
<223> OTHER INFORMATION: Any amino acid
<220> FEATURE:
<221> NAME/KEY: MOD_RES
<222> LOCATION: (6)..(6)
```

```
<223> OTHER INFORMATION: N, S or T

<400> SEQUENCE: 44

Xaa Xaa Xaa Xaa Xaa Xaa
1               5

<210> SEQ ID NO 45
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: F, Y, W, I, L or V
<220> FEATURE:
<221> NAME/KEY: MOD_RES
<222> LOCATION: (2)..(2)
<223> OTHER INFORMATION: Any amino acid
<220> FEATURE:
<221> NAME/KEY: MOD_RES
<222> LOCATION: (3)..(3)
<223> OTHER INFORMATION: Any amino acid
<220> FEATURE:
<221> NAME/KEY: MOD_RES
<222> LOCATION: (4)..(4)
<223> OTHER INFORMATION: D, E, H, K, N, Q, R, S, T or Y
<220> FEATURE:
<221> NAME/KEY: MOD_RES
<222> LOCATION: (5)..(5)
<223> OTHER INFORMATION: Any amino acid
<220> FEATURE:
<221> NAME/KEY: MOD_RES
<222> LOCATION: (6)..(6)
<223> OTHER INFORMATION: N, S or T
<220> FEATURE:
<221> NAME/KEY: MOD_RES
<222> LOCATION: (7)..(7)
<223> OTHER INFORMATION: Any amino acid
<220> FEATURE:
<221> NAME/KEY: MOD_RES
<222> LOCATION: (8)..(8)
<223> OTHER INFORMATION: V, I, L, Y or F

<400> SEQUENCE: 45

Xaa Xaa Xaa Xaa Xaa Xaa Xaa Xaa
1               5

<210> SEQ ID NO 46
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: F, I, L, V or Y
<220> FEATURE:
<221> NAME/KEY: MOD_RES
<222> LOCATION: (2)..(2)
<223> OTHER INFORMATION: Any amino acid
<220> FEATURE:
<221> NAME/KEY: MOD_RES
<222> LOCATION: (3)..(3)
<223> OTHER INFORMATION: Any amino acid
<220> FEATURE:
<221> NAME/KEY: MOD_RES
<222> LOCATION: (4)..(4)
<223> OTHER INFORMATION: Any amino acid
<220> FEATURE:
<221> NAME/KEY: MOD_RES
```

```
<222> LOCATION: (5)..(5)
<223> OTHER INFORMATION: H, K or R

<400> SEQUENCE: 46

Xaa Xaa Xaa Xaa Xaa
1               5

<210> SEQ ID NO 47
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Y, F, W or L
<220> FEATURE:
<221> NAME/KEY: MOD_RES
<222> LOCATION: (2)..(2)
<223> OTHER INFORMATION: Any amino acid
<220> FEATURE:
<221> NAME/KEY: MOD_RES
<222> LOCATION: (3)..(3)
<223> OTHER INFORMATION: Any amino acid
<220> FEATURE:
<221> NAME/KEY: MOD_RES
<222> LOCATION: (4)..(4)
<223> OTHER INFORMATION: A or S

<400> SEQUENCE: 47

Xaa Xaa Xaa Xaa
1

<210> SEQ ID NO 48
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: W, Y, F or L
<220> FEATURE:
<221> NAME/KEY: MOD_RES
<222> LOCATION: (2)..(2)
<223> OTHER INFORMATION: Any amino acid
<220> FEATURE:
<221> NAME/KEY: MOD_RES
<222> LOCATION: (3)..(3)
<223> OTHER INFORMATION: Any amino acid
<220> FEATURE:
<221> NAME/KEY: MOD_RES
<222> LOCATION: (4)..(4)
<223> OTHER INFORMATION: A, V or S

<400> SEQUENCE: 48

Xaa Xaa Xaa Xaa
1

<210> SEQ ID NO 49
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
```

```
<223> OTHER INFORMATION: Y or F
<220> FEATURE:
<221> NAME/KEY: MOD_RES
<222> LOCATION: (2)..(2)
<223> OTHER INFORMATION: Any amino acid
<220> FEATURE:
<221> NAME/KEY: MOD_RES
<222> LOCATION: (3)..(3)
<223> OTHER INFORMATION: Any amino acid
<220> FEATURE:
<221> NAME/KEY: MOD_RES
<222> LOCATION: (4)..(4)
<223> OTHER INFORMATION: L, V, M, A, F or Y
<220> FEATURE:
<221> NAME/KEY: MOD_RES
<222> LOCATION: (5)..(5)
<223> OTHER INFORMATION: Any amino acid
<220> FEATURE:
<221> NAME/KEY: MOD_RES
<222> LOCATION: (6)..(6)
<223> OTHER INFORMATION: R, K or H
<220> FEATURE:
<221> NAME/KEY: MOD_RES
<222> LOCATION: (7)..(7)
<223> OTHER INFORMATION: Any amino acid
<220> FEATURE:
<221> NAME/KEY: MOD_RES
<222> LOCATION: (8)..(8)
<223> OTHER INFORMATION: Any amino acid
<220> FEATURE:
<221> NAME/KEY: MOD_RES
<222> LOCATION: (9)..(9)
<223> OTHER INFORMATION: A, G, S or P

<400> SEQUENCE: 49

Xaa Xaa Xaa Xaa Xaa Xaa Xaa Xaa Xaa
1               5

<210> SEQ ID NO 50
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: W, Y or F
<220> FEATURE:
<221> NAME/KEY: MOD_RES
<222> LOCATION: (2)..(2)
<223> OTHER INFORMATION: Any amino acid
<220> FEATURE:
<221> NAME/KEY: MOD_RES
<222> LOCATION: (3)..(3)
<223> OTHER INFORMATION: Any amino acid
<220> FEATURE:
<221> NAME/KEY: MOD_RES
<222> LOCATION: (4)..(4)
<223> OTHER INFORMATION: L, V, M, A or F
<220> FEATURE:
<221> NAME/KEY: MOD_RES
<222> LOCATION: (5)..(5)
<223> OTHER INFORMATION: Any amino acid
<220> FEATURE:
<221> NAME/KEY: MOD_RES
<222> LOCATION: (6)..(6)
<223> OTHER INFORMATION: R, K or H
<220> FEATURE:
<221> NAME/KEY: MOD_RES
<222> LOCATION: (7)..(7)
<223> OTHER INFORMATION: Any amino acid
<220> FEATURE:
<221> NAME/KEY: MOD_RES
<222> LOCATION: (8)..(8)
<223> OTHER INFORMATION: Any amino acid
```

```
<220> FEATURE:
<221> NAME/KEY: MOD_RES
<222> LOCATION: (9)..(9)
<223> OTHER INFORMATION: A, G, S or P

<400> SEQUENCE: 50

Xaa Xaa Xaa Xaa Xaa Xaa Xaa Xaa Xaa
1               5

<210> SEQ ID NO 51
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Y or F
<220> FEATURE:
<221> NAME/KEY: MOD_RES
<222> LOCATION: (2)..(2)
<223> OTHER INFORMATION: Any amino acid
<220> FEATURE:
<221> NAME/KEY: MOD_RES
<222> LOCATION: (3)..(3)
<223> OTHER INFORMATION: Any amino acid
<220> FEATURE:
<221> NAME/KEY: MOD_RES
<222> LOCATION: (4)..(4)
<223> OTHER INFORMATION: Any amino acid
<220> FEATURE:
<221> NAME/KEY: MOD_RES
<222> LOCATION: (5)..(5)
<223> OTHER INFORMATION: Any amino acid
<220> FEATURE:
<221> NAME/KEY: MOD_RES
<222> LOCATION: (6)..(6)
<223> OTHER INFORMATION: R or K
<220> FEATURE:
<221> NAME/KEY: MOD_RES
<222> LOCATION: (7)..(7)
<223> OTHER INFORMATION: Any amino acid
<220> FEATURE:
<221> NAME/KEY: MOD_RES
<222> LOCATION: (8)..(8)
<223> OTHER INFORMATION: R or K

<400> SEQUENCE: 51

Xaa Xaa Xaa Xaa Xaa Xaa Xaa Xaa
1               5

<210> SEQ ID NO 52
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: I, L or V
<220> FEATURE:
<221> NAME/KEY: MOD_RES
<222> LOCATION: (2)..(2)
<223> OTHER INFORMATION: Any amino acid
<220> FEATURE:
<221> NAME/KEY: MOD_RES
<222> LOCATION: (3)..(3)
<223> OTHER INFORMATION: Any amino acid
<220> FEATURE:
<221> NAME/KEY: MOD_RES
<222> LOCATION: (4)..(4)
```

```
<223> OTHER INFORMATION: L, V, M, A, F or Y
<220> FEATURE:
<221> NAME/KEY: MOD_RES
<222> LOCATION: (5)..(5)
<223> OTHER INFORMATION: Any amino acid
<220> FEATURE:
<221> NAME/KEY: MOD_RES
<222> LOCATION: (6)..(6)
<223> OTHER INFORMATION: R, K or H
<220> FEATURE:
<221> NAME/KEY: MOD_RES
<222> LOCATION: (7)..(7)
<223> OTHER INFORMATION: Any amino acid
<220> FEATURE:
<221> NAME/KEY: MOD_RES
<222> LOCATION: (8)..(8)
<223> OTHER INFORMATION: Any amino acid
<220> FEATURE:
<221> NAME/KEY: MOD_RES
<222> LOCATION: (9)..(9)
<223> OTHER INFORMATION: A, G, S or P

<400> SEQUENCE: 52

Xaa Xaa Xaa Xaa Xaa Xaa Xaa Xaa Xaa
1               5

<210> SEQ ID NO 53
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: I, L, F, Y or V
<220> FEATURE:
<221> NAME/KEY: MOD_RES
<222> LOCATION: (2)..(2)
<223> OTHER INFORMATION: Any amino acid
<220> FEATURE:
<221> NAME/KEY: MOD_RES
<222> LOCATION: (3)..(3)
<223> OTHER INFORMATION: L, N, M, V or A
<220> FEATURE:
<221> NAME/KEY: MOD_RES
<222> LOCATION: (4)..(4)
<223> OTHER INFORMATION: Any amino acid
<220> FEATURE:
<221> NAME/KEY: MOD_RES
<222> LOCATION: (5)..(5)
<223> OTHER INFORMATION: Any amino acid
<220> FEATURE:
<221> NAME/KEY: MOD_RES
<222> LOCATION: (6)..(6)
<223> OTHER INFORMATION: V, Y, F, I or N
<220> FEATURE:
<221> NAME/KEY: MOD_RES
<222> LOCATION: (7)..(7)
<223> OTHER INFORMATION: Any amino acid
<220> FEATURE:
<221> NAME/KEY: MOD_RES
<222> LOCATION: (8)..(8)
<223> OTHER INFORMATION: Any amino acid
<220> FEATURE:
<221> NAME/KEY: MOD_RES
<222> LOCATION: (9)..(9)
<223> OTHER INFORMATION: Y, F, M, I or V

<400> SEQUENCE: 53

Xaa Xaa Xaa Xaa Xaa Xaa Xaa Xaa Xaa
1               5

<210> SEQ ID NO 54
```

```
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: I, L, F, Y or V
<220> FEATURE:
<221> NAME/KEY: MOD_RES
<222> LOCATION: (2)..(2)
<223> OTHER INFORMATION: Any amino acid
<220> FEATURE:
<221> NAME/KEY: MOD_RES
<222> LOCATION: (3)..(3)
<223> OTHER INFORMATION: L, M, N, V or A
<220> FEATURE:
<221> NAME/KEY: MOD_RES
<222> LOCATION: (4)..(4)
<223> OTHER INFORMATION: Any amino acid
<220> FEATURE:
<221> NAME/KEY: MOD_RES
<222> LOCATION: (5)..(5)
<223> OTHER INFORMATION: Any amino acid
<220> FEATURE:
<221> NAME/KEY: MOD_RES
<222> LOCATION: (6)..(6)
<223> OTHER INFORMATION: V, Y, F, I, N or A
<220> FEATURE:
<221> NAME/KEY: MOD_RES
<222> LOCATION: (7)..(7)
<223> OTHER INFORMATION: Any amino acid
<220> FEATURE:
<221> NAME/KEY: MOD_RES
<222> LOCATION: (8)..(8)
<223> OTHER INFORMATION: Any amino acid
<220> FEATURE:
<221> NAME/KEY: MOD_RES
<222> LOCATION: (9)..(9)
<223> OTHER INFORMATION: Y, F, M, I or V

<400> SEQUENCE: 54

Xaa Xaa Xaa Xaa Xaa Xaa Xaa Xaa Xaa
1               5

<210> SEQ ID NO 55
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: I, V or F
<220> FEATURE:
<221> NAME/KEY: MOD_RES
<222> LOCATION: (2)..(2)
<223> OTHER INFORMATION: Any amino acid
<220> FEATURE:
<221> NAME/KEY: MOD_RES
<222> LOCATION: (3)..(3)
<223> OTHER INFORMATION: Any amino acid
<220> FEATURE:
<221> NAME/KEY: MOD_RES
<222> LOCATION: (4)..(4)
<223> OTHER INFORMATION: Y, W, L, V, A or M
<220> FEATURE:
<221> NAME/KEY: MOD_RES
<222> LOCATION: (5)..(5)
<223> OTHER INFORMATION: Any amino acid
<220> FEATURE:
<221> NAME/KEY: MOD_RES
<222> LOCATION: (6)..(6)
```

```
<223> OTHER INFORMATION: R or K
<220> FEATURE:
<221> NAME/KEY: MOD_RES
<222> LOCATION: (7)..(7)
<223> OTHER INFORMATION: Any amino acid
<220> FEATURE:
<221> NAME/KEY: MOD_RES
<222> LOCATION: (8)..(8)
<223> OTHER INFORMATION: Any amino acid
<220> FEATURE:
<221> NAME/KEY: MOD_RES
<222> LOCATION: (9)..(9)
<223> OTHER INFORMATION: Y, F, A, S or T

<400> SEQUENCE: 55

Xaa Xaa Xaa Xaa Xaa Xaa Xaa Xaa Xaa
1               5

<210> SEQ ID NO 56
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: I, L or V
<220> FEATURE:
<221> NAME/KEY: MOD_RES
<222> LOCATION: (2)..(2)
<223> OTHER INFORMATION: Any amino acid
<220> FEATURE:
<221> NAME/KEY: MOD_RES
<222> LOCATION: (3)..(3)
<223> OTHER INFORMATION: Any amino acid
<220> FEATURE:
<221> NAME/KEY: MOD_RES
<222> LOCATION: (4)..(4)
<223> OTHER INFORMATION: L, V, M, A, W or Y
<220> FEATURE:
<221> NAME/KEY: MOD_RES
<222> LOCATION: (5)..(5)
<223> OTHER INFORMATION: Any amino acid
<220> FEATURE:
<221> NAME/KEY: MOD_RES
<222> LOCATION: (6)..(6)
<223> OTHER INFORMATION: R or K
<220> FEATURE:
<221> NAME/KEY: MOD_RES
<222> LOCATION: (7)..(7)
<223> OTHER INFORMATION: Any amino acid
<220> FEATURE:
<221> NAME/KEY: MOD_RES
<222> LOCATION: (8)..(8)
<223> OTHER INFORMATION: Any amino acid
<220> FEATURE:
<221> NAME/KEY: MOD_RES
<222> LOCATION: (9)..(9)
<223> OTHER INFORMATION: Y, F, A, S or T

<400> SEQUENCE: 56

Xaa Xaa Xaa Xaa Xaa Xaa Xaa Xaa Xaa
1               5

<210> SEQ ID NO 57
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
```

```
<222> LOCATION: (1)..(1)
<223> OTHER INFORMATION: I, L or V
<220> FEATURE:
<221> NAME/KEY: MOD_RES
<222> LOCATION: (2)..(2)
<223> OTHER INFORMATION: Any amino acid
<220> FEATURE:
<221> NAME/KEY: MOD_RES
<222> LOCATION: (3)..(3)
<223> OTHER INFORMATION: Any amino acid
<220> FEATURE:
<221> NAME/KEY: MOD_RES
<222> LOCATION: (4)..(4)
<223> OTHER INFORMATION: Any amino acid
<220> FEATURE:
<221> NAME/KEY: MOD_RES
<222> LOCATION: (5)..(5)
<223> OTHER INFORMATION: Any amino acid
<220> FEATURE:
<221> NAME/KEY: MOD_RES
<222> LOCATION: (6)..(6)
<223> OTHER INFORMATION: R or K
<220> FEATURE:
<221> NAME/KEY: MOD_RES
<222> LOCATION: (7)..(7)
<223> OTHER INFORMATION: Any amino acid
<220> FEATURE:
<221> NAME/KEY: MOD_RES
<222> LOCATION: (8)..(8)
<223> OTHER INFORMATION: Any amino acid

<400> SEQUENCE: 57

Xaa Xaa Xaa Xaa Xaa Xaa Xaa Xaa Tyr
1               5

<210> SEQ ID NO 58
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Y, F, V, A or I
<220> FEATURE:
<221> NAME/KEY: MOD_RES
<222> LOCATION: (2)..(2)
<223> OTHER INFORMATION: Any amino acid
<220> FEATURE:
<221> NAME/KEY: MOD_RES
<222> LOCATION: (3)..(3)
<223> OTHER INFORMATION: Any amino acid
<220> FEATURE:
<221> NAME/KEY: MOD_RES
<222> LOCATION: (4)..(4)
<223> OTHER INFORMATION: Y, W, L, V, A or M
<220> FEATURE:
<221> NAME/KEY: MOD_RES
<222> LOCATION: (5)..(5)
<223> OTHER INFORMATION: Any amino acid
<220> FEATURE:
<221> NAME/KEY: MOD_RES
<222> LOCATION: (6)..(6)
<223> OTHER INFORMATION: R or K
<220> FEATURE:
<221> NAME/KEY: MOD_RES
<222> LOCATION: (7)..(7)
<223> OTHER INFORMATION: Any amino acid
<220> FEATURE:
<221> NAME/KEY: MOD_RES
<222> LOCATION: (8)..(8)
<223> OTHER INFORMATION: Any amino acid
<220> FEATURE:
<221> NAME/KEY: MOD_RES
<222> LOCATION: (9)..(9)
```

<223> OTHER INFORMATION: Y, F, A, S or T

<400> SEQUENCE: 58

Xaa Xaa Xaa Xaa Xaa Xaa Xaa Xaa Xaa
1               5

<210> SEQ ID NO 59
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Y, F, V, A or I
<220> FEATURE:
<221> NAME/KEY: MOD_RES
<222> LOCATION: (2)..(2)
<223> OTHER INFORMATION: Any amino acid
<220> FEATURE:
<221> NAME/KEY: MOD_RES
<222> LOCATION: (3)..(3)
<223> OTHER INFORMATION: Any amino acid
<220> FEATURE:
<221> NAME/KEY: MOD_RES
<222> LOCATION: (4)..(4)
<223> OTHER INFORMATION: L, V, M, A, W or Y
<220> FEATURE:
<221> NAME/KEY: MOD_RES
<222> LOCATION: (5)..(5)
<223> OTHER INFORMATION: Any amino acid
<220> FEATURE:
<221> NAME/KEY: MOD_RES
<222> LOCATION: (6)..(6)
<223> OTHER INFORMATION: R or K
<220> FEATURE:
<221> NAME/KEY: MOD_RES
<222> LOCATION: (7)..(7)
<223> OTHER INFORMATION: Any amino acid
<220> FEATURE:
<221> NAME/KEY: MOD_RES
<222> LOCATION: (8)..(8)
<223> OTHER INFORMATION: Any amino acid
<220> FEATURE:
<221> NAME/KEY: MOD_RES
<222> LOCATION: (9)..(9)
<223> OTHER INFORMATION: Y, F, A, S or T

<400> SEQUENCE: 59

Xaa Xaa Xaa Xaa Xaa Xaa Xaa Xaa Xaa
1               5

<210> SEQ ID NO 60
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: I, L, F or Y
<220> FEATURE:
<221> NAME/KEY: MOD_RES
<222> LOCATION: (2)..(2)
<223> OTHER INFORMATION: Any amino acid
<220> FEATURE:
<221> NAME/KEY: MOD_RES
<222> LOCATION: (3)..(3)
<223> OTHER INFORMATION: Any amino acid
<220> FEATURE:
<221> NAME/KEY: MOD_RES

```
<222> LOCATION: (4)..(4)
<223> OTHER INFORMATION: Any amino acid
<220> FEATURE:
<221> NAME/KEY: MOD_RES
<222> LOCATION: (5)..(5)
<223> OTHER INFORMATION: Any amino acid
<220> FEATURE:
<221> NAME/KEY: MOD_RES
<222> LOCATION: (6)..(6)
<223> OTHER INFORMATION: R or K
<220> FEATURE:
<221> NAME/KEY: MOD_RES
<222> LOCATION: (7)..(7)
<223> OTHER INFORMATION: Any amino acid
<220> FEATURE:
<221> NAME/KEY: MOD_RES
<222> LOCATION: (8)..(8)
<223> OTHER INFORMATION: Any amino acid

<400> SEQUENCE: 60

Xaa Xaa Xaa Xaa Xaa Xaa Xaa Xaa Tyr
1               5

<210> SEQ ID NO 61
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: L, V or I
<220> FEATURE:
<221> NAME/KEY: MOD_RES
<222> LOCATION: (2)..(2)
<223> OTHER INFORMATION: Any amino acid
<220> FEATURE:
<221> NAME/KEY: MOD_RES
<222> LOCATION: (3)..(3)
<223> OTHER INFORMATION: Any amino acid
<220> FEATURE:
<221> NAME/KEY: MOD_RES
<222> LOCATION: (4)..(4)
<223> OTHER INFORMATION: F, Y or I
<220> FEATURE:
<221> NAME/KEY: MOD_RES
<222> LOCATION: (5)..(5)
<223> OTHER INFORMATION: Any amino acid
<220> FEATURE:
<221> NAME/KEY: MOD_RES
<222> LOCATION: (6)..(6)
<223> OTHER INFORMATION: Any amino acid
<220> FEATURE:
<221> NAME/KEY: MOD_RES
<222> LOCATION: (7)..(7)
<223> OTHER INFORMATION: I, L, V, M or F

<400> SEQUENCE: 61

Xaa Xaa Xaa Xaa Xaa Xaa Xaa
1               5

<210> SEQ ID NO 62
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: I, L or V
<220> FEATURE:
```

```
<221> NAME/KEY: MOD_RES
<222> LOCATION: (2)..(2)
<223> OTHER INFORMATION: Any amino acid
<220> FEATURE:
<221> NAME/KEY: MOD_RES
<222> LOCATION: (3)..(3)
<223> OTHER INFORMATION: Any amino acid
<220> FEATURE:
<221> NAME/KEY: MOD_RES
<222> LOCATION: (4)..(4)
<223> OTHER INFORMATION: Any amino acid
<220> FEATURE:
<221> NAME/KEY: MOD_RES
<222> LOCATION: (5)..(5)
<223> OTHER INFORMATION: Any amino acid
<220> FEATURE:
<221> NAME/KEY: MOD_RES
<222> LOCATION: (6)..(6)
<223> OTHER INFORMATION: Any amino acid
<220> FEATURE:
<221> NAME/KEY: MOD_RES
<222> LOCATION: (7)..(7)
<223> OTHER INFORMATION: Any amino acid
<220> FEATURE:
<221> NAME/KEY: MOD_RES
<222> LOCATION: (8)..(8)
<223> OTHER INFORMATION: Any amino acid
<220> FEATURE:
<221> NAME/KEY: MOD_RES
<222> LOCATION: (9)..(9)
<223> OTHER INFORMATION: Any amino acid
<220> FEATURE:
<221> NAME/KEY: MOD_RES
<222> LOCATION: (10)..(10)
<223> OTHER INFORMATION: H, K or R

<400> SEQUENCE: 62

Xaa Xaa Xaa Xaa Xaa Xaa Xaa Xaa Xaa Xaa
1               5                   10

<210> SEQ ID NO 63
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Y, F, I or L
<220> FEATURE:
<221> NAME/KEY: MOD_RES
<222> LOCATION: (2)..(2)
<223> OTHER INFORMATION: Any amino acid
<220> FEATURE:
<221> NAME/KEY: MOD_RES
<222> LOCATION: (3)..(3)
<223> OTHER INFORMATION: Any amino acid
<220> FEATURE:
<221> NAME/KEY: MOD_RES
<222> LOCATION: (5)..(5)
<223> OTHER INFORMATION: Any amino acid
<220> FEATURE:
<221> NAME/KEY: MOD_RES
<222> LOCATION: (6)..(6)
<223> OTHER INFORMATION: A, S, P, D or E
<220> FEATURE:
<221> NAME/KEY: MOD_RES
<222> LOCATION: (7)..(7)
<223> OTHER INFORMATION: Any amino acid
<220> FEATURE:
<221> NAME/KEY: MOD_RES
<222> LOCATION: (8)..(8)
<223> OTHER INFORMATION: Any amino acid
<220> FEATURE:
<221> NAME/KEY: MOD_RES
```

```
<222> LOCATION: (9)..(9)
<223> OTHER INFORMATION: L, V, I, S or G

<400> SEQUENCE: 63

Xaa Xaa Xaa Asn Xaa Xaa Xaa Xaa Xaa
1               5

<210> SEQ ID NO 64
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: I, L or V
<220> FEATURE:
<221> NAME/KEY: MOD_RES
<222> LOCATION: (2)..(2)
<223> OTHER INFORMATION: Any amino acid
<220> FEATURE:
<221> NAME/KEY: MOD_RES
<222> LOCATION: (3)..(3)
<223> OTHER INFORMATION: Any amino acid
<220> FEATURE:
<221> NAME/KEY: MOD_RES
<222> LOCATION: (5)..(5)
<223> OTHER INFORMATION: Any amino acid
<220> FEATURE:
<221> NAME/KEY: MOD_RES
<222> LOCATION: (6)..(6)
<223> OTHER INFORMATION: A, S, P, D or E
<220> FEATURE:
<221> NAME/KEY: MOD_RES
<222> LOCATION: (7)..(7)
<223> OTHER INFORMATION: Any amino acid
<220> FEATURE:
<221> NAME/KEY: MOD_RES
<222> LOCATION: (8)..(8)
<223> OTHER INFORMATION: Any amino acid
<220> FEATURE:
<221> NAME/KEY: MOD_RES
<222> LOCATION: (9)..(9)
<223> OTHER INFORMATION: I, L or V

<400> SEQUENCE: 64

Xaa Xaa Xaa Asn Xaa Xaa Xaa Xaa Xaa
1               5

<210> SEQ ID NO 65
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: F, Y, L or M
<220> FEATURE:
<221> NAME/KEY: MOD_RES
<222> LOCATION: (2)..(2)
<223> OTHER INFORMATION: Any amino acid
<220> FEATURE:
<221> NAME/KEY: MOD_RES
<222> LOCATION: (3)..(3)
<223> OTHER INFORMATION: Any amino acid
<220> FEATURE:
<221> NAME/KEY: MOD_RES
<222> LOCATION: (4)..(4)
<223> OTHER INFORMATION: Q, V, I or M
<220> FEATURE:
```

```
<221> NAME/KEY: MOD_RES
<222> LOCATION: (5)..(5)
<223> OTHER INFORMATION: Any amino acid
<220> FEATURE:
<221> NAME/KEY: MOD_RES
<222> LOCATION: (6)..(6)
<223> OTHER INFORMATION: Any amino acid
<220> FEATURE:
<221> NAME/KEY: MOD_RES
<222> LOCATION: (7)..(7)
<223> OTHER INFORMATION: Any amino acid
<220> FEATURE:
<221> NAME/KEY: MOD_RES
<222> LOCATION: (8)..(8)
<223> OTHER INFORMATION: Any amino acid
<220> FEATURE:
<221> NAME/KEY: MOD_RES
<222> LOCATION: (9)..(9)
<223> OTHER INFORMATION: R or K

<400> SEQUENCE: 65

Xaa Xaa Xaa Xaa Xaa Xaa Xaa Xaa Xaa
1               5

<210> SEQ ID NO 66
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: R or K
<220> FEATURE:
<221> NAME/KEY: MOD_RES
<222> LOCATION: (2)..(2)
<223> OTHER INFORMATION: Any amino acid
<220> FEATURE:
<221> NAME/KEY: MOD_RES
<222> LOCATION: (3)..(3)
<223> OTHER INFORMATION: Any amino acid
<220> FEATURE:
<221> NAME/KEY: MOD_RES
<222> LOCATION: (4)..(4)
<223> OTHER INFORMATION: Any amino acid
<220> FEATURE:
<221> NAME/KEY: MOD_RES
<222> LOCATION: (5)..(5)
<223> OTHER INFORMATION: Any amino acid
<220> FEATURE:
<221> NAME/KEY: MOD_RES
<222> LOCATION: (6)..(6)
<223> OTHER INFORMATION: A or G
<220> FEATURE:
<221> NAME/KEY: MOD_RES
<222> LOCATION: (7)..(7)
<223> OTHER INFORMATION: Any amino acid
<220> FEATURE:
<221> NAME/KEY: MOD_RES
<222> LOCATION: (8)..(8)
<223> OTHER INFORMATION: Any amino acid
<220> FEATURE:
<221> NAME/KEY: MOD_RES
<222> LOCATION: (9)..(9)
<223> OTHER INFORMATION: N, E or D

<400> SEQUENCE: 66

Xaa Xaa Xaa Xaa Xaa Xaa Xaa Xaa Xaa
1               5

<210> SEQ ID NO 67
<211> LENGTH: 9
<212> TYPE: PRT
```

```
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: F, W, Y, I, L or V
<220> FEATURE:
<221> NAME/KEY: MOD_RES
<222> LOCATION: (2)..(2)
<223> OTHER INFORMATION: Any amino acid
<220> FEATURE:
<221> NAME/KEY: MOD_RES
<222> LOCATION: (3)..(3)
<223> OTHER INFORMATION: Any amino acid
<220> FEATURE:
<221> NAME/KEY: MOD_RES
<222> LOCATION: (4)..(4)
<223> OTHER INFORMATION: D, E, L, V, I or H
<220> FEATURE:
<221> NAME/KEY: MOD_RES
<222> LOCATION: (5)..(5)
<223> OTHER INFORMATION: Any amino acid
<220> FEATURE:
<221> NAME/KEY: MOD_RES
<222> LOCATION: (6)..(6)
<223> OTHER INFORMATION: P, D, E, H, P or A
<220> FEATURE:
<221> NAME/KEY: MOD_RES
<222> LOCATION: (7)..(7)
<223> OTHER INFORMATION: D or E
<220> FEATURE:
<221> NAME/KEY: MOD_RES
<222> LOCATION: (8)..(8)
<223> OTHER INFORMATION: Any amino acid
<220> FEATURE:
<221> NAME/KEY: MOD_RES
<222> LOCATION: (9)..(9)
<223> OTHER INFORMATION: F, W, Y, I, L, V or M

<400> SEQUENCE: 67

Xaa Xaa Xaa Xaa Xaa Xaa Xaa Xaa Xaa
1               5

<210> SEQ ID NO 68
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: A, F, C, I, L, M, N, Q, S, T, V, W, Y, D or E
<220> FEATURE:
<221> NAME/KEY: MOD_RES
<222> LOCATION: (2)..(2)
<223> OTHER INFORMATION: Any amino acid
<220> FEATURE:
<221> NAME/KEY: MOD_RES
<222> LOCATION: (3)..(3)
<223> OTHER INFORMATION: A, F, G, I, L, M, N, Q, S, T, V, W, Y, C, D or
      E
<220> FEATURE:
<221> NAME/KEY: MOD_RES
<222> LOCATION: (4)..(4)
<223> OTHER INFORMATION: A, F, G, I, L, M, N, Q, S, T, V, W or Y
<220> FEATURE:
<221> NAME/KEY: MOD_RES
<222> LOCATION: (5)..(5)
<223> OTHER INFORMATION: Any amino acid
<220> FEATURE:
<221> NAME/KEY: MOD_RES
<222> LOCATION: (6)..(6)
<223> OTHER INFORMATION: L, I, V, A, P, S or T
```

-continued

```
<220> FEATURE:
<221> NAME/KEY: MOD_RES
<222> LOCATION: (7)..(7)
<223> OTHER INFORMATION: Any amino acid
<220> FEATURE:
<221> NAME/KEY: MOD_RES
<222> LOCATION: (8)..(8)
<223> OTHER INFORMATION: Any amino acid
<220> FEATURE:
<221> NAME/KEY: MOD_RES
<222> LOCATION: (9)..(9)
<223> OTHER INFORMATION: A, S, T, G, L, I, V or P

<400> SEQUENCE: 68

Xaa Xaa Xaa Xaa Xaa Xaa Xaa Xaa Xaa
1               5

<210> SEQ ID NO 69
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: F, Y or W
<220> FEATURE:
<221> NAME/KEY: MOD_RES
<222> LOCATION: (2)..(2)
<223> OTHER INFORMATION: Any amino acid
<220> FEATURE:
<221> NAME/KEY: MOD_RES
<222> LOCATION: (3)..(3)
<223> OTHER INFORMATION: Any amino acid
<220> FEATURE:
<221> NAME/KEY: MOD_RES
<222> LOCATION: (4)..(4)
<223> OTHER INFORMATION: A, V or K
<220> FEATURE:
<221> NAME/KEY: MOD_RES
<222> LOCATION: (5)..(5)
<223> OTHER INFORMATION: Any amino acid
<220> FEATURE:
<221> NAME/KEY: MOD_RES
<222> LOCATION: (6)..(6)
<223> OTHER INFORMATION: N, T, D or S
<220> FEATURE:
<221> NAME/KEY: MOD_RES
<222> LOCATION: (7)..(7)
<223> OTHER INFORMATION: Any amino acid
<220> FEATURE:
<221> NAME/KEY: MOD_RES
<222> LOCATION: (8)..(8)
<223> OTHER INFORMATION: Any amino acid
<220> FEATURE:
<221> NAME/KEY: MOD_RES
<222> LOCATION: (9)..(9)
<223> OTHER INFORMATION: Any amino acid
<220> FEATURE:
<221> NAME/KEY: MOD_RES
<222> LOCATION: (10)..(10)
<223> OTHER INFORMATION: Q or N

<400> SEQUENCE: 69

Xaa Xaa Xaa Xaa Xaa Xaa Xaa Xaa Xaa Xaa
1               5                   10

<210> SEQ ID NO 70
<211> LENGTH: 9
<212> TYPE: PRT
<213> ORGANISM: Artificial Sequence
<220> FEATURE:
<223> OTHER INFORMATION: Description of Artificial Sequence: Synthetic
```

```
            peptide
<220> FEATURE:
<221> NAME/KEY: MOD_RES
<222> LOCATION: (1)..(1)
<223> OTHER INFORMATION: F, Y, W, I, L or V
<220> FEATURE:
<221> NAME/KEY: MOD_RES
<222> LOCATION: (2)..(2)
<223> OTHER INFORMATION: Any amino acid
<220> FEATURE:
<221> NAME/KEY: MOD_RES
<222> LOCATION: (3)..(3)
<223> OTHER INFORMATION: Any amino acid
<220> FEATURE:
<221> NAME/KEY: MOD_RES
<222> LOCATION: (4)..(4)
<223> OTHER INFORMATION: D, E, H, K, N, Q, R, S, T or Y
<220> FEATURE:
<221> NAME/KEY: MOD_RES
<222> LOCATION: (5)..(5)
<223> OTHER INFORMATION: Any amino acid
<220> FEATURE:
<221> NAME/KEY: MOD_RES
<222> LOCATION: (6)..(6)
<223> OTHER INFORMATION: N, S or T
<220> FEATURE:
<221> NAME/KEY: MOD_RES
<222> LOCATION: (7)..(7)
<223> OTHER INFORMATION: Any amino acid
<220> FEATURE:
<221> NAME/KEY: MOD_RES
<222> LOCATION: (8)..(8)
<223> OTHER INFORMATION: Any amino acid
<220> FEATURE:
<221> NAME/KEY: MOD_RES
<222> LOCATION: (9)..(9)
<223> OTHER INFORMATION: V, I, L, Y or F

<400> SEQUENCE: 70

Xaa Xaa Xaa Xaa Xaa Xaa Xaa Xaa Xaa
1               5

<210> SEQ ID NO 71
<211> LENGTH: 9
<212> TYPE: PRT
<213> ORGANISM: Artificial Sequence
<220> FEATURE:
<223> OTHER INFORMATION: Description of Artificial Sequence: Synthetic
            peptide
<220> FEATURE:
<221> NAME/KEY: MOD_RES
<222> LOCATION: (1)..(1)
<223> OTHER INFORMATION: W, Y or F
<220> FEATURE:
<221> NAME/KEY: MOD_RES
<222> LOCATION: (2)..(2)
<223> OTHER INFORMATION: Any amino acid
<220> FEATURE:
<221> NAME/KEY: MOD_RES
<222> LOCATION: (3)..(3)
<223> OTHER INFORMATION: Any amino acid
<220> FEATURE:
<221> NAME/KEY: MOD_RES
<222> LOCATION: (4)..(4)
<223> OTHER INFORMATION: L, V, M, A, F or Y
<220> FEATURE:
<221> NAME/KEY: MOD_RES
<222> LOCATION: (5)..(5)
<223> OTHER INFORMATION: Any amino acid
<220> FEATURE:
<221> NAME/KEY: MOD_RES
<222> LOCATION: (6)..(6)
<223> OTHER INFORMATION: R, K or H
<220> FEATURE:
<221> NAME/KEY: MOD_RES
<222> LOCATION: (7)..(7)
<223> OTHER INFORMATION: Any amino acid
```

```
<220> FEATURE:
<221> NAME/KEY: MOD_RES
<222> LOCATION: (8)..(8)
<223> OTHER INFORMATION: Any amino acid
<220> FEATURE:
<221> NAME/KEY: MOD_RES
<222> LOCATION: (9)..(9)
<223> OTHER INFORMATION: A, G, S or P

<400> SEQUENCE: 71

Xaa Xaa Xaa Xaa Xaa Xaa Xaa Xaa Xaa
1               5

<210> SEQ ID NO 72
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: I, V or F
<220> FEATURE:
<221> NAME/KEY: MOD_RES
<222> LOCATION: (2)..(2)
<223> OTHER INFORMATION: Any amino acid
<220> FEATURE:
<221> NAME/KEY: MOD_RES
<222> LOCATION: (3)..(3)
<223> OTHER INFORMATION: Any amino acid
<220> FEATURE:
<221> NAME/KEY: MOD_RES
<222> LOCATION: (4)..(4)
<223> OTHER INFORMATION: L, V, M, A, W or Y
<220> FEATURE:
<221> NAME/KEY: MOD_RES
<222> LOCATION: (5)..(5)
<223> OTHER INFORMATION: Any amino acid
<220> FEATURE:
<221> NAME/KEY: MOD_RES
<222> LOCATION: (6)..(6)
<223> OTHER INFORMATION: R or K
<220> FEATURE:
<221> NAME/KEY: MOD_RES
<222> LOCATION: (7)..(7)
<223> OTHER INFORMATION: Any amino acid
<220> FEATURE:
<221> NAME/KEY: MOD_RES
<222> LOCATION: (8)..(8)
<223> OTHER INFORMATION: Any amino acid
<220> FEATURE:
<221> NAME/KEY: MOD_RES
<222> LOCATION: (9)..(9)
<223> OTHER INFORMATION: Y, F, A, S or T

<400> SEQUENCE: 72

Xaa Xaa Xaa Xaa Xaa Xaa Xaa Xaa Xaa
1               5

<210> SEQ ID NO 73
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Y, F, V, A or I
<220> FEATURE:
<221> NAME/KEY: MOD_RES
<222> LOCATION: (2)..(2)
```

```
<223> OTHER INFORMATION: Any amino acid
<220> FEATURE:
<221> NAME/KEY: MOD_RES
<222> LOCATION: (3)..(3)
<223> OTHER INFORMATION: Any amino acid
<220> FEATURE:
<221> NAME/KEY: MOD_RES
<222> LOCATION: (4)..(4)
<223> OTHER INFORMATION: Y, W, L, V, A or M
<220> FEATURE:
<221> NAME/KEY: MOD_RES
<222> LOCATION: (5)..(5)
<223> OTHER INFORMATION: Any amino acid
<220> FEATURE:
<221> NAME/KEY: MOD_RES
<222> LOCATION: (6)..(6)
<223> OTHER INFORMATION: R or K
<220> FEATURE:
<221> NAME/KEY: MOD_RES
<222> LOCATION: (7)..(7)
<223> OTHER INFORMATION: Any amino acid
<220> FEATURE:
<221> NAME/KEY: MOD_RES
<222> LOCATION: (8)..(8)
<223> OTHER INFORMATION: Any amino acid
<220> FEATURE:
<221> NAME/KEY: MOD_RES
<222> LOCATION: (9)..(9)
<223> OTHER INFORMATION: Y, E, A, S or T

<400> SEQUENCE: 73

Xaa Xaa Xaa Xaa Xaa Xaa Xaa Xaa Xaa
1               5

<210> SEQ ID NO 74
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Y, F, V, A or I
<220> FEATURE:
<221> NAME/KEY: MOD_RES
<222> LOCATION: (2)..(2)
<223> OTHER INFORMATION: Any amino acid
<220> FEATURE:
<221> NAME/KEY: MOD_RES
<222> LOCATION: (3)..(3)
<223> OTHER INFORMATION: Any amino acid
<220> FEATURE:
<221> NAME/KEY: MOD_RES
<222> LOCATION: (4)..(4)
<223> OTHER INFORMATION: L, V, M, A, W or Y
<220> FEATURE:
<221> NAME/KEY: MOD_RES
<222> LOCATION: (5)..(5)
<223> OTHER INFORMATION: Any amino acid
<220> FEATURE:
<221> NAME/KEY: MOD_RES
<222> LOCATION: (6)..(6)
<223> OTHER INFORMATION: R or K
<220> FEATURE:
<221> NAME/KEY: MOD_RES
<222> LOCATION: (7)..(7)
<223> OTHER INFORMATION: Any amino acid
<220> FEATURE:
<221> NAME/KEY: MOD_RES
<222> LOCATION: (8)..(8)
<223> OTHER INFORMATION: Any amino acid
<220> FEATURE:
<221> NAME/KEY: MOD_RES
<222> LOCATION: (9)..(9)
<223> OTHER INFORMATION: Y, E, A, S or T
```

<400> SEQUENCE: 74

Xaa Xaa Xaa Xaa Xaa Xaa Xaa Xaa Xaa
1               5

CANCER ANTIGEN HELPER PEPTIDE

The present application is a continuation of U.S. application Ser. No. 15/831,484, filed Dec. 5, 2017, which is a continuation of U.S. application Ser. No. 14/994,801, filed Jan. 13, 2016, which is a divisional of U.S. application Ser. No. 13/265,806, filed Oct. 21, 2011 (now U.S. Pat. No. 9,266,932), which is a National Stage entry of PCT/JP2010/057149, filed Apr. 22, 2010, and claims priority to Japanese Patent Application No. 2009-105286, filed Apr. 23, 2009, the disclosures all of which are incorporated herein by reference.

SEQUENCE LISTING

The instant application contains a Sequence Listing, which has been submitted electronically in ASCII format and is hereby incorporated by reference in its entirety. Said ASCII copy, created on May 1, 2015, is named 05273_0135_SL.txt and is 58,313 bytes in size.

TECHNICAL FIELD

The present invention relates to WT1 helper peptide, a polynucleotide encoding the peptide, WT1-specific helper T cells induced by the peptide, a pharmaceutical composition for treating/preventing cancer comprising them and the like.

BACKGROUND ART

The WT1 gene (Wilms' tumor 1 gene) is a gene identified as a causative gene of a Wilms' tumor which is a kidney cancer in childhood (Non-Patent Documents 1 and 2), and is a transcription factor having a zinc finger structure. At first, the WT1 gene was considered to be a cancer suppressor gene. However, subsequent investigation showed that the above gene rather serves as a cancer gene in hematopoietic organ tumors and solid cancers (Non-Patent Documents 3 to 6).

Since the WT1 gene is highly expressed in many malignant tumors, a WT1 gene product which is a self-protein having no mutation has been verified for existence or non-existence of immunogenicity in vivo. As a result, it has been shown that a protein derived from the WT1 gene highly expressed in tumor cells is fragmented by intracellular processing and the resulting peptide forms a complex with an MHC class I molecule which is displayed on the cell surface, and that cytotoxic T cells (hereinafter also referred to as CTLs) recognizing such a complex can be induced by WT1 peptide vaccination (Non-Patent Documents 7 to 9). It has also been shown that mice immunized with a WT1 peptide or a WT1 cDNA reject implanted WT1 gene-expressing tumor cells in a high rate (Non-Patent Documents 7 and 10) but normal tissues endogenously expressing the WT1 gene are not damaged by induced CTLs (Non-Patent Document 7). Heretofore, it has been strongly suggested that it is possible to induce WT1-specific CTLs in not only mice but also human, and that such CTLs have a cytotoxic activity against tumor cells highly expressing the WT1 gene, but have no cytotoxic activity against normal cells endogenously expressing the WT1 gene (Non-Patent Documents 7 and 10 to 14).

On the other hand, it is reported that the presence of helper T cells specific to a cancer antigen is important in order to induce the CTLs effectively (Non-Patent Document 15). The helper T cells (CD4-positive T cells) are induced, proliferated, and activated by recognizing a complex of an MHC class II molecule with an antigen peptide on antigen presenting cells. Activated helper T cells produce cytokines such as IL-2, IL-4, IL-5, IL-6, or an interferon (IFN), and promote proliferation, differentiation and maturation of B cells and other subsets of T cells. Thus, it is considered that an antigen peptide binding to an MHC class II molecule effectively activates CTLs and others through induction of helper T cells and enhances an immune function (Non-Patent Document 16).

Heretofore, only an antigen peptide binding to HLA-DRB1*0401 and HLA-DRB1*0405 of an MHC class II molecule has been reported with respect to WT1 (Non-Patent Document 17 and Patent Document 1), and it was necessary to find antigen peptides to other subtypes.

PRIOR ART DOCUMENTS

Non-Patent Documents

Patent Document 1: International Publication No. WO 2005/045027

Non-Patent Documents

Non-Patent Document 1: Daniel A. Haber et al., Cell. 1990 Jun. 29; 61(7): 1257-69.
Non-Patent Document 2: Call K M et al., Cell. 1990 Feb. 9; 60(3): 509-20.
Non-Patent Document 3: Menke A L et al., Int Rev Cytol. 1998; 181: 151-212. Review.
Non-Patent Document 4: Yamagami T et al., Blood. 1996 Apr. 1; 87(7): 2878-84.
Non-Patent Document 5: Inoue K et al., Blood. 1998 Apr. 15; 91(8): 2969-76.
Non-Patent Document 6: Tsuboi A et al., Leuk Res. 1999 May; 23(5): 499-505.
Non-Patent Document 7: Oka Y et al., J Immunol. 2000 Feb. 15; 164(4): 1873-80.
Non-Patent Document 8: Melief C J et al., Immunol Rev. 1995 June; 145: 167-77.
Non-Patent Document 9: Ritz J, J Clin Oncol. 1994 February; 12(2): 237-8.
Non-Patent Document 10: Tsuboi A et al., J Clin Immunol. 2000 May; 20(3): 195-202.
Non-Patent Document 11: Oka Y et al., Immunogenetics. 2000 February; 51(2): 99-107.
Non-Patent Document 12: Ohminami H et al., Blood. 2000 Jan. 1; 95(1): 286-93.
Non-Patent Document 13: Gao L et al., Blood. 2000 Apr. 1; 95(7): 2198-203.
Non-Patent Document 14: Ohminami H et al., Blood. 2000 Jan. 1; 95(1): 286-93.
Non-Patent Document 15: Cancer. Res. 62: 6438, 2002
Non-Patent Document 16: J. Immunol. Immunother., 24: 195, 2001
Non-Patent Document 17: Cancer. Immunol. Immunother. 51: 271, 2002

DISCLOSURE OF THE INVENTION

Problems to be Solved by the Invention

Accordingly, an object to be achieved by the present invention is to provide a peptide inducing WT1-specific helper T cells by binding to various MHC class II molecules, a polynucleotide encoding the peptide, WT1 helper T cells induced by the peptide, and a pharmaceutical composition for treating/preventing cancer comprising them.

Means for Solving the Problems

The present inventors have intensively studied to achieve the above object. As a result, they has found that a peptide having a portion of a sequence of contiguous amino acids encoding a WT1 protein functions as a cancer antigen helper peptide, in other words, the peptide is displayed on antigen presenting cells by binding to an MHC class II molecule and induces WT1-specific helper T cells, and showed that the peptide can be used in a pharmaceutical composition for treating/preventing cancer.

Thus, the present invention provides:

(1) A peptide which has an amino acid sequence consisting of contiguous amino acids derived from a WT1 protein and induces WT1-specific helper T cells by binding to an MHC class II molecule, wherein the amino acid sequence is selected from the group consisting of:

(a) the amino acid sequence depicted in SEQ ID NO:3;
(b) the amino acid sequence depicted in SEQ ID NO:4;
(c) the amino acid sequence depicted in SEQ ID NO:5; and
(d) an amino acid sequence in which one or several amino acids are substituted, deleted or added in the amino acid sequences depicted in (a) to (c);

(2) The peptide according to (1), wherein the amino acid sequence is the amino acid sequence depicted in SEQ ID NO:3;

(3) The peptide according to (1) or (2), wherein the MHC class II molecule is selected from the group consisting of DRB1*0101, DRB1*0405, DRB1*0802, DRB1*0803, DRB1*0901, DRB1*1201, DRB1*1403, DRB1*1501, DRB1*1502, DPB1*0201, DPB1*0202, DPB1*0402, DPB1*0501, DPB1*0901, DQB1*0301, DQB1*0302, DQB1*0401, DQB1*0501, DQB1*0601, DQB1*0602, and DRB5*0102;

(4) The peptide according to (1) or (2), wherein the MHC class II molecule is selected from the group consisting of DRB1*0101, DRB1*0405, DRB1*1502, DPB1*0201, DPB1*0202, and DQB1*0601;

(5) A polynucleotide encoding the peptide according to any one of (1) to (4);

(6) An expression vector comprising the polynucleotide according to (5);

(7) An antibody against the peptide according to any one of (1) to (4), or the polynucleotide according to (5);

(8) A pharmaceutical composition for treating or preventing cancer, comprising the peptide according to any one of (1) to (4), the polynucleotide according to (5), or the vector according to (6);

(9) A method for treating or preventing cancer, which comprises administering an effective amount of the peptide according to any one of (1) to (4), the polynucleotide according to (5), or the vector according to (6) to a subject having the MHC class II molecule according to (3) or (4);

(10) Use of the peptide according to any one of (1) to (4), the polynucleotide according to (5), or the vector according to (6) for treating or preventing cancer;

(11) Antigen presenting cells which display the peptide according to any one of (1) to (4) through the MHC class II molecule according to (3) or (4);

(12) A method for inducing antigen presenting cells, which includes culturing immature antigen presenting cells in the presence of the peptide according to any one of (1) to (4), and inducing antigen presenting cells, which display the peptide through the MHC class II molecule according to (3) or (4), from the immature antigen presenting cells;

(13) WT1-Specific helper T cells which are induced by the peptide according to any one of (1) to (4);

(14) A method for inducing WT1-specific helper T cells, which comprises culturing peripheral blood mononuclear cells in the presence of the peptide according to any one of (1) to (4), and inducing WT1-specific helper T cells from the peripheral blood mononuclear cells;

(15) A kit for inducing WT1-specific helper T cells, comprising, as an essential ingredient, the peptide according to any one of (1) to (4);

(16) A kit for preventing or treating cancer, comprising, as an essential ingredient, the peptide according to any one of (1) to (4), the polynucleotide according to (5), or the vector according to (6);

(17) A method for determining the presence or amount of WT1-specific helper T cells in a subject having the MHC class II molecule according to (3) or (4), said method comprising the steps of:

(a) reacting the peptide according to any one of (1) to (4) with a sample derived from the subject; and then
(b) determining the presence or amount of a cytokine contained in the sample.

Effects of the Invention

According to the present invention, it is possible to obtain WT1 helper peptides which bind to many types of MHC class II molecules such as DRB1*0101, DRB1*0405, DRB1*0802, DRB1*0803, DRB1*0901, DRB1*1201, DRB1*1403, DRB1*1501, DRB1*1502, DPB1*0201, DPB1*0202, DPB1*0402, DPB1*0501, DPB1*0901, DQB1*0301, DQB1*0302, DQB1*0401, DQB1*0501, DQB1*0601, DQB1*0602, and DRB5*0102, a pharmaceutical composition for treating/preventing cancer including them and the like. Thus, it becomes possible to induce WT1-specific helper T cells in vivo and in vitro in various subjects (in particular, most Japanese have the above molecules). Since the WT1-specific helper T cells are induced by the present invention, it is also possible to activate T cells and B cells effectively in cancer highly expressing the WT1.

BRIEF DESCRIPTION OF THE DRAWINGS

FIGS. 1A-1C show the results obtained by measuring cell proliferation after stimulating each peptide-specific T cell line, which was prepared by pulsing with each of three peptides ($mWT1_{35}$, $mWT1_{86}$, and $mWT1_{294}$), with each peptide. In the drawing, the symbol "-" shows no peptide stimulation.

FIGS. 2A-2C show the results obtained by measuring cell proliferation after stimulating each peptide-specific T cell line, which was prepared by pulsing with three peptides ($mWT1_{35}$ $mWT1_{86}$ and $mWT1_{294}$), with each corresponding peptide in the presence of an anti-MHC class I or II antibody. In the drawing, the symbol "-" shows no peptide stimulation. The symbol "cpm" in the ordinate shows counts per minute.

MODE FOR CARRYING OUT THE INVENTION

Figure 3:
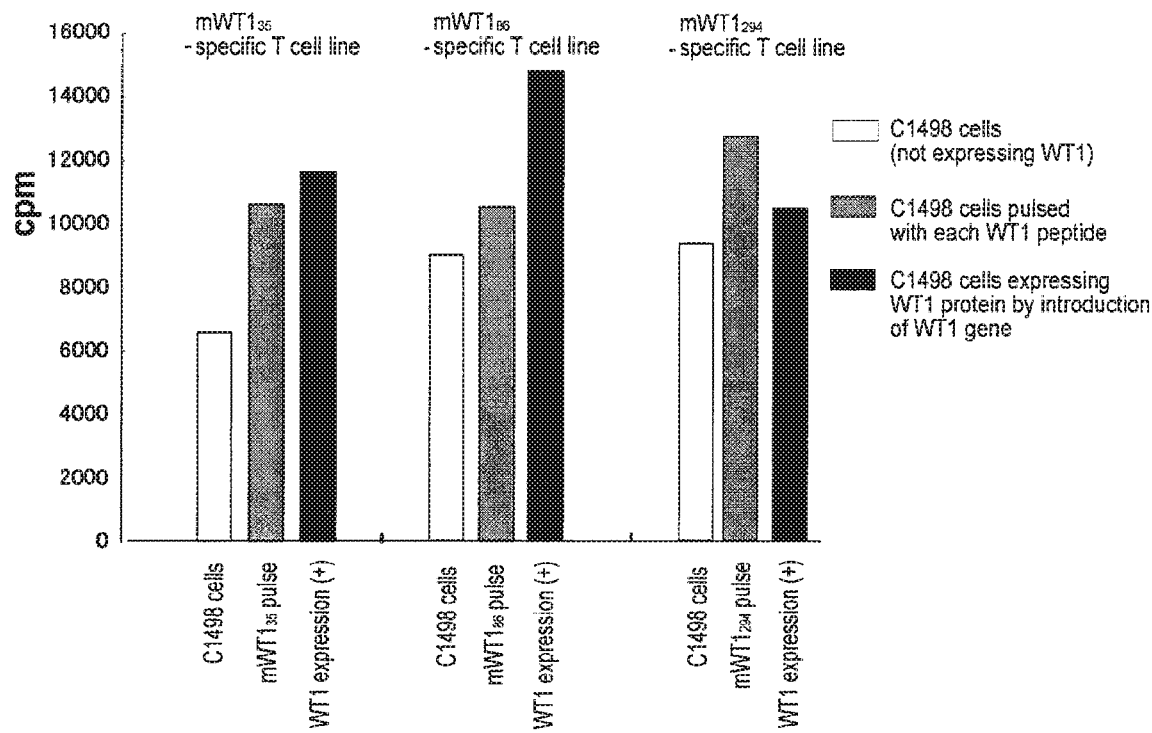
FIG. 3 shows the results obtained by measuring cell proliferation of each WT1 peptide-specific T cell line in response to C1498 cells, C1498 cells pulsed with three peptides ($mWT1_{3\ 5}$, $mWT1_{8\ 6}$, and $mWT1_{2\ 9\ 4}$), as well as C1498 cells having forced expression of a WT1 protein. The symbol "cpm" in the ordinate shows counts per minute.

In one aspect, the present invention relates to a peptide having an amino acid sequence consisting of amino acids derived from a mouse or human WT1 protein. The WT1 gene is highly expressed, for example, in hematopoietic organ tumors such as leukemia; myelodysplastic syndrome, multiple myeloma, and malignant lymphoma; solid cancers such as stomach cancer, bowel cancer, lung cancer, breast cancer, germ-cell cancer, liver cancer, skin cancer, bladder cancer, prostate cancer, uterus cancer, cervical cancer, and ovary cancer. Thus, the peptide of the present invention is present in cancer cells expressing the WT1 gene in a large amount.

The peptide of the present invention is a peptide which has an amino acid sequence consisting of contiguous amino acids derived from the human WT1 protein depicted in SEQ ID NO:2, retains an ability to bind to the MHC class II molecules as shown below, and has an ability to induce WT1-specific helper T cells. There is no particular limitation on the amino acid sequence and length of the peptide of the present invention as long as the peptide has the above features. However, too long peptide is susceptible to a protease action, and too short peptide can not bind to a peptide accommodating groove well. The length of the peptide of the present invention is preferably 10 to 25 amino acids, more preferably 15 to 21 amino acids, further preferably 16 to 20 amino acids, for example, of 17 amino acids, 18 amino acids, or 19 amino acids. Specific examples of the peptide of the present invention are those having the amino acid sequence depicted in SEQ ID NO:3; the amino acid sequence depicted in SEQ ID NO:4; and the amino acid sequence depicted in SEQ ID NO:5.

Also, the peptide of the present invention includes variants of the above peptides. The variants may contain, for example, a peptide selected from the group consisting of peptides having an amino acid sequence which has substitution, deletion or addition of several amino acids, for example, 1 to 9, preferably 1 to 5, 1 to 4, 1 to 3, more preferably 1 to 2 amino acids, further preferably one amino acid in one of the above amino acid sequences. Substitution of amino acids in peptides may be carried out at any positions and with any types of amino acids. Conservative amino acid substitution is preferred. For example, a Glu residue may be substituted with an Asp residue, a Phe residue with a Tyr residue, a Leu residue with an Ile residue, an Ala residue with a Ser residue, and a His residue with an Arg residue. Addition or deletion of amino acids may be carried out preferably at the N-terminus and the C-terminus in peptides, but may be carried out in an interior sequence. A preferred specific example of the peptide of the present invention has the sequence of SEQ ID NO:3. In this regard, all the above peptides must retain an ability to bind to an MHC class II molecule and have an ability to induce WT1-specific helper T cells.

In this connection, the MHC class II molecule to which the peptide of the present invention binds may belong to any subclass of HLA-DR, HLA-DQ, and HLA-DP. Preferably, the MHC class II molecule is one selected from the group consisting of DRB1*0101, DRB1*0405, DRB1*0802, DRB1*0803, DRB1*0901, DRB1*1201, DRB1*1403, DRB1*1501, DRB1*1502, DPB1*0201, DPB1*0202, DPB1*0402, DPB1*0501, DPB1*0901, DQB1*0301, DQB1*0302, DQB1*0401, DQB1*0501, DQB1*0601, DQB1*0602, and DRB5*0102. More preferably, the MHC class II molecule is DRB1*0101, DRB1*0405, DRB1*1403, DRB1*1502, DPB1*0201, DPB1*0202, DPB1*0901, DQB1*0301, DQB1*0601 or DRB5*0102, and most preferably, DRB10101, DRB1*0405, DRB1*1502, DPB1*0201, DPB1*0202, or DQB1*0601. In the present specification, a peptide which retains an ability to bind to an MHC class II molecule and has an ability to induce WT1-specific helper T cells is referred to as a WT1 helper peptide. Also, in the Examples described below, a peptide having the amino acid sequence depicted in SEQ ID NO:3 is referred to as a $WT1_{35}$ peptide, $WT1_{35}$ helper peptide or $WT1_{35}$ peptide.

Also, the peptide of the present invention may be a peptide having an amino acid sequence consisting of contiguous amino acids derived from the mouse WT1 protein depicted in SEQ ID NO:1, and the above amino acid sequence may be a peptide (SEQ ID NO:6) in which an amino acid residue at position 9 in the amino acid sequence depicted in SEQ ID NO:4 is substituted with leucine; or a peptide (SEQ ID NO:7) in which an amino acid residue at position 11 in the amino acid sequence depicted in SEQ ID NO:5 is substituted with serine. Moreover, the peptide of the present invention may contain a peptide selected from the group consisting of peptides having an amino acid sequence which has substitution, deletion or addition of several amino acids, for example, 1 to 9, preferably 1 to 5, 1 to 4, 1 to 3, more preferably 1 to 2 amino acids, further preferably one amino acid in the amino acid sequence depicted in SEQ ID NO:6 or SEQ ID NO:7. In the Examples described below, a peptide having the amino acid sequence depicted in SEQ ID NO:6 is also referred to as an $mWT1_{86}$ peptide or an $mWT1_{86}$ helper peptide, and a peptide having the amino acid sequence depicted in SEQ ID NO:7 as an $mWT1_{294}$ peptide or an $mWT1_{294}$ helper peptide.

The peptide of the present invention may be derived from a WT1 protein, and may consist of the above sequence of contiguous amino acids or comprise the sequence. Thus, the peptide of the present invention may be, for example, a peptide consisting of the above amino acid sequence itself, or a WT1 protein comprising the above amino acid sequence or a portion thereof. Also, the peptide of the present invention may be that obtained by modification of the above amino acid sequence. Amino acid residues in the above amino acid sequence can be modified by a known method. Such modification may be, for example, esterification, alkylation, halogenation, phosphorylation, sulfonation, amidation and the like on a functional group in a side chain of an amino acid residue constituting a peptide. Also, it is possible to bind various substances to the N-terminus and/or C-terminus of a peptide containing the above amino acid sequence. For example, an amino acid, a peptide, an analog thereof and the like may be bound to the peptide. In case these substances are bound to the peptide of the present invention, they may be treated, for example, by an enzyme in vivo and the like or by a process such as intracellular processing so as to finally generate a peptide consisting of the above amino acid sequence, which is displayed on cell surface as a complex with an MHC class IT molecule, thereby being able to obtain an induction effect of helper T cells. These substances may be those regulating solubility of the peptide of the present invention, those improving stability of the peptide such as protease resistance, those allowing specific delivery of the peptide of the present invention, for example, to a given tissue or organ, or those having an enhancing action of an uptake efficiency of antigen presenting cells or other action. Also, these substances may be those increasing an ability to induce CTLs, for example, helper peptides other than the peptide of the present invention.

The modification of the peptide of the present invention may be modification of an amino group on an N-terminal amino acid or of a carboxyl group on a C-terminal amino acid of the peptide. Modifying groups of an amino group on an N-terminal amino acid include, for example, one to three alkyl groups having 1 to 6 carbon atoms, phenyl groups, cycloalkyl groups, and acyl groups. Specific examples of the acyl group include an alkanoyl group having 1 to 6 carbon atoms, an alkanoyl group having 1 to 6 carbon atoms substituted with a phenyl group, a carbonyl group substituted with a cycloalkyl group having 5 to 7 carbon atoms, an alkylsulfonyl group having 1 to 6 carbon atoms, a phenylsulfonyl group, an alkoxycarbonyl group having 2 to 6 carbon atoms, an alkoxycarbonyl group substituted with a phenyl group, a carbonyl group substituted with a cycloalkoxy group having 5 to 7 carbon atoms, a phenoxycarbonyl group and the like. Peptides having modification of a carboxyl group on a C-terminal amino acid include, for example, esterified and amidated peptides. Specific examples of the ester include an alkyl ester having 1 to 6 carbon atoms, an alkyl ester having 0 to 6 carbon atoms substituted with a phenyl group, a cycloalkyl ester having 5 to 7 carbon atoms and the like, and specific examples of the amide include an amide, an amide substituted with one or two alkyl groups having 1 to 6 carbon atoms, an amide substituted with one or two alkyl groups having 0 to 6 carbon atoms substituted with a phenyl group, an amide forming a 5- to 7-membered azacycloalkane including a nitrogen atom of the amide group, and the like.

Also, the modification of the peptide of the present invention may be carried out by binding amino acid residues to each other through a bond other than a peptide bond such as a carbon-carbon bond, a carbon-nitrogen bond, and a carbon-sulfur bond. Moreover, the peptide of the present invention may contain one or more D-amino acids.

The above-mentioned peptides, variant peptides and modified peptides according to the present invention are illustrative only, and those skilled in the art can easily assume, prepare, evaluate and use other variations of the above peptides.

The peptide of the present invention can be synthesized using a method routinely used in the art or a modified method thereof. Such a synthesis method is disclosed, for example, in Peptide Synthesis, Interscience, New York, 1966; The Proteins, Vol. 2, Academic Press Inc., New York, 1976; Peptide Synthesis, Maruzen Co., Ltd., 1975; Basis and Experiments of Peptide Synthesis, Maruzen Co., Ltd., 1985; Development of Medicines (continuation), Vol. 14, Peptide Synthesis, Hirokawa Shoten Co., 1991 and the like. Also, the peptide of the present invention can be prepared using a genetic engineering technique on the basis of information of a nucleotide sequence encoding the peptide of the present invention. Such a genetic engineering technique is well known to those skilled in the art. Such a technique can be conducted according to a method described in literatures [Molecular Cloning, T. Maniatis et al., CSH Laboratory (1983); DNA Cloning, DM. Glover, IRL PRESS (1985)] as described above or a method described below, and other methods.

It is possible to determine whether the peptide of the present invention or a candidate peptide thereof binds to the above MHC class II molecule and induces helper T cells, by a known method such as, for example, a method described in Cancer Immunol. Immunother. 51:271 (2002), or a method described in the Examples of the present specification, and other methods.

Since the peptide of the present invention activates helper T cells (CD4-positive T cells), the peptide induces and maintains differentiation of CTLs and exerts an action of activating effector cells such as macrophages. Accordingly, it is possible to use the peptide of the present invention for effective treatment or prevention of cancer.

In another aspect, the present invention relates to a polynucleotide encoding the above WT1 helper peptide (hereinafter also referred to as a WT1 polynucleotide). The polynucleotide of the present invention may be a DNA or an RNA. The base sequence of the polynucleotide of the present invention can be determined on the basis of the amino acid sequence of the above WT1 helper peptide. The polynucleotide can be prepared, for example, by a method for DNA or RNA synthesis, a PCR method and the like.

The polynucleotide of the present invention includes a polynucleotide which hybridizes with a complementary sequence of a polynucleotide encoding the peptide of the present invention under a stringent condition and encodes a peptide having an activity comparable to that of the peptide of the present invention. As to the term "hybridize under a stringent condition", hybridization used herein can be carried out according to a conventional method described, for example, in Molecular Cloning, 2nd edition, Sambrook J., Frisch E. F., Maniatis T., Cold Spring Harbor Laboratory press and the like. Also, the "stringent condition" includes, for example, a condition wherein a hybrid is formed in a solution containing 6×SSC (10×SSC is a solution containing 1.5 M NaCl and 0.15 M trisodium citrate) and 50% formamide at 45° C. and then washed with 2×SSC at 50° C. (Molecular Biology, John Wiley & Sons, N.Y. (1989), 6.3.1-6.3.6) and the like.

In still another aspect, the present invention relates to an expression vector comprising the above polynucleotide (hereinafter also referred to as a WT1 expression vector). The type of expression vectors, other sequences contained in addition to the above polynucleotide sequence and the like can be appropriately selected depending on the type of hosts into which the expression vectors are introduced, the purpose of the introduction and the like. Examples of the expression vector include plasmids, phage vectors, virus vectors and the like. In case the host is *Escherichia coli* cells, examples of the vector include plasmid vectors such as pUC118, pUC119, pBR322, and pCR3, as well as phage vectors such as λZAPII, and Δgt11. In case the host is yeast cells, examples of the vector include pYES2, pYEUra3 and the like. In case the host is insect cells, examples of the vector pAcSGHisNT-A and the like. In case the host is animal cells, examples of the vector include plasmid vectors such as pKCR, pCDM8, pGL2, pcDNA3.1, pRc/RSV, and pRc/CMV, virus vectors such as a retrovirus vector, an adenovirus vector, and an adeno-associated virus vector. The vector may optionally contain factors such as an expression-inducible promoter, a gene encoding a signal sequence, a marker gene for selection, and a terminator. Also, a sequence expressed as a fusion protein with thioredoxin, a His tag, GST (glutathione S-transferase) and the like may be added to the vector for easy isolation and purification. In this case, it is possible to use a GST-fused protein vector (pGEX4T, etc.) having a suitable promoter (lac, tac, trc, trp, CMV, SV40 early promoter, etc.) functional in host cells, a vector (pcDNA3.1/Myc-His, etc.) having a tag sequence such as Myc and His, and also a vector (pET32a) expressing a fusion protein with thioredoxin and a His tag and the like.

When the expression vector of the present invention is administered to a subject to produce a WT1 helper peptide in vivo, WT1-specific helper T cells induced by the peptide produce various cytokines (for example, IL-2, IL-4, IL-5, IL-6, or an interferon (IFN), etc.), and promote proliferation, differentiation and maturation of B cells and other T cells. Accordingly, tumor cells which have an MHC class I molecule and highly express WT1 can be damaged specifically using the WT1 expression vector of the present invention.

In another aspect, the present invention relates to an antibody against the above WT1 helper peptide or a polynucleotide encoding the peptide (hereinafter also referred to as a WT1 antibody). The antibody of the present invention may be either of a polyclonal antibody or a monoclonal antibody. A method for preparing such an antibody is already known, and the antibody of the present invention can be prepared according to such a conventional method as well (Current protocols in Molecular Biology, Ausubel et al. (ed.), 1987, John Wiley and Sons (pub.), Section 11.12-11.13, Antibodies; A Laboratory Manual, Lane, H. D. et al. (ed.), Cold Spring Harber Laboratory Press (pub.), New York, 1989).

The present invention relates to a pharmaceutical composition for treating or preventing cancer, comprising the above WT1 helper peptide, WT1 polynucleotide, or WT1 expression vector. The WT1 gene is highly expressed, for example, in hematopoietic organ tumors such as leukemia, myelodysplastic syndrome, multiple myeloma, and malignant lymphoma, as well as in solid cancers such as stomach cancer, bowel cancer, lung cancer, breast cancer, germ-cell cancer, liver cancer, skin cancer, bladder cancer, prostate cancer, uterus cancer, cervical cancer, and ovary cancer, and therefore, it is possible to use the pharmaceutical composition of the present invention for treating or preventing cancer expressing the WT1 gene. When the pharmaceutical composition of the present invention is administered to a subject having an MHC class II molecule, WT1-specific helper T cells induced by a WT1 helper peptide contained in the pharmaceutical composition produce various cytokines (for example, IL-2, IL-4, IL-5, IL-6, or an interferon (IFN), etc.), and promote proliferation, differentiation and maturation of B cells and other subsets of T cells. Accordingly, tumor cells which have an MHC class I molecule and highly express WT1 can be damaged specifically using the peptide of the present invention.

The pharmaceutical composition of the present invention may comprise, for example, a carrier, an excipient and the like, in addition to the above WT1 helper peptide, WT1 polynucleotide, or WT1 expression vector as an effective component. The WT1 helper peptide contained in the pharmaceutical composition of the present invention induces WT1-specific helper T cells, and thus the pharmaceutical composition of the present invention may comprise a suitable adjuvant or may be administered together with a suitable adjuvant in order to enhance the induction efficiency. Examples of preferred adjuvant include, but are not limited to, a Freund's complete or incomplete adjuvant, aluminium hydroxide and the like. Also, the pharmaceutical composition of the present invention may also comprise a known cancer antigen peptide other than the above WT1 helper peptide such as, for example, a $WT1_{126}$ peptide inducing WT1-specific CTLs, as an effective component (Oka et al, "Cancer immunotherapy targeting Wilms' tumor gene WT1 product", Journal of Immunology, 164:1873-1880, 2000; and Oka et al., "Human cytotoxic T-lymphocyte responses specific for peptides of the wild-type Wilms' tumor gene (WT1) product", Immunogenetics, 51: 99-107, 2000).

Moreover, the pharmaceutical composition of the present invention may be administered in combination with a known cancer antigen peptide. For example, a known cancer antigen peptide, for example, a $WT1_{126}$ peptide can be administered before or after the administration of the pharmaceutical composition of the present invention. The pharmaceutical composition of the present invention has a feature that activates B cells or other T cells by inducing WT1-specific helper T cells, and therefore, it is possible to further enhance an activity of CTLs induced by administering a known cancer antigen peptide, and to remarkably increase therapeutic effects.

A method for administering the pharmaceutical composition of the present invention can be appropriately selected depending on conditions such as the type of diseases, the state of subjects, and the targeted sites. Examples of the administration method includes, but are not limited to, intradermal administration, subcutaneous administration, intramuscular administration, intravenous administration, transnasal administration, oral administration and the like. Also, the administration method may be a lymphocyte therapy or a DC (dendritic cell) therapy. The amount of a peptide contained in the pharmaceutical composition of the present invention, the form and administration frequency of the pharmaceutical composition and the like can be appropriately selected depending on conditions such as the type of diseases, the state of subjects, and the targeted sites. In general, the amount of a peptide administered per dose is 0.0001 mg to 1000 mg, and preferably 0.001 mg to 10,000 mg.

In another aspect, the present invention relates to a method for treating or preventing cancer, which comprises administering an effective amount of the above pharmaceutical composition to a subject having the above MHC class II molecule. Cancers to be treated or prevented may be any cancers as long as they express the WT1 gene and include, for example, hematopoietic organ tumors such as leukemia, myelodysplastic syndrome, multiple myeloma, and malignant lymphoma, as well as solid cancers such as stomach cancer, bowel cancer, lung cancer, breast cancer, germ-cell cancer, liver cancer, skin cancer, bladder cancer, prostate cancer, uterus cancer, cervical cancer, and ovary cancer.

In another aspect, the present invention relates to use of the above WT1 helper peptide, WT1 polynucleotide, or WT1 expression vector for treating or preventing cancer.

In still another aspect, the present invention relates to use of the WT1 helper peptide for preparing a pharmaceutical composition for treating or preventing cancer.

In still another aspect, the present invention relates to use of the WT1 polynucleotide or WT1 expression vector for preparing a pharmaceutical composition containing the above WT1 polynucleotide or WT1 expression vector.

In another aspect, the present invention relates to cells including the above WT1 helper peptide, WT1 polynucleotide, or WT1 expression vector. The cells of the present invention can be prepared, for example, by transforming host cells such as *Escherichia coli* cells, yeast cells, insect cells, and animal cells using the above expression vector. Transformation of host cells with an expression vector can be carried out using various methods properly selected. The peptide of the present invention can be prepared by culturing transformed cells, and recovering and purifying a WT1 helper peptide produced.

In still another aspect, the present invention relates to antigen presenting cells (for example, dendritic cells, B-lymphocytes, macrophages, etc.), which display the above WT1 helper peptide through the above MHC class II molecule. The antigen presenting cells of the present invention are induced by the above WT1 helper peptide. WT1-specific helper T cells are efficiently induced using the antigen presenting cells of the present invention.

In still another aspect, the present invention relates to a method for inducing antigen presenting cells which display a WT1 helper peptide through an MHC class II molecule, said method comprising culturing immature antigen presenting cells in the presence of a WT1 helper peptide, and inducing antigen presenting cells, which display the WT1 helper peptide through the above MHC class II molecule, from the immature antigen presenting cells. In the present specification, the immature antigen presenting cells refer to cells which can become antigen presenting cells such as, for example, dendritic cells, B-lymphocytes, and macrophages upon maturation. Subjects from which the immature antigen presenting cells derive may be any subjects as long as they have the above MHC class II molecule. Since the immature antigen presenting cells are contained, for example, in peripheral blood mononuclear cells and the like, such cells may be cultured in the presence of the above WT1 helper peptide.

In another aspect, the present invention relates to a method for treating or preventing cancer, which comprises administering antigen presenting cells, which display a WT1 helper peptide through the above MHC class II molecule, to a subject having the same molecule as the above MHC class II molecule. The administration method of the antigen presenting cells can be appropriately selected depending on conditions such as the type of diseases, the state of subjects, and the targeted sites. Examples of the method include, but are not limited to, intravenous administration, intradermal administration, subcutaneous administration, intramuscular administration, transnasal administration, oral administration and the like.

In still another aspect, the present invention relates to a method for preventing or treating cancer by induction of antigen presenting cells which display a WT1 helper peptide through the above MHC class II molecule, said method comprising the steps of:

(a) reacting a sample with a nucleotide sequence encoding an amino acid sequence (SEQ ID NO:2) of a WT1 protein or a nucleic acid having a partial sequence thereof or the above WT1 helper peptide;

(b) obtaining antigen presenting cells which display a WT1 helper peptide contained in the sample through the above MHC class II molecule; and (c) administering the antigen presenting cells to a subject having the same molecule as the above MHC class II molecule.

Samples in the above method may be any samples as long as they have a possibility of containing lymphocytes or dendritic cells and include, for example, subject-derived samples such as blood, cell culture solutions and the like. The reaction in the above method may be carried out using a conventional technique, and preferably using electroporation. Obtainment of the antigen presenting cells can be carried out using a method known to those skilled in the art. Culturing conditions of cells in a sample in each step can be determined properly by those skilled in the art. The administration method of the antigen presenting cells may be as described above.

In further aspect, the present invention relates to WT1-specific helper T cells induced by the above WT1 helper peptide. The helper T cells of the present invention are induced, proliferated, and activated when recognizing a complex of a WT1 helper peptide with an MHC class II molecule. The activated WT1-specific helper T cells produce cytokines such as IL-2, IL-4, IL-5, IL-6, or an interferon (IFN), and promote proliferation, differentiation and maturation of B cells and other subsets of T cells. Accordingly, tumor cells which have an MHC class I molecule and highly express WT1 can be damaged specifically using the helper T cells of the present invention.

In another aspect, the present invention relates to a method for inducing WT1-specific helper T cells, which comprises culturing peripheral blood mononuclear cells in the presence of a WT1 helper peptide, and inducing the WT1-specific helper T cells from the peripheral blood mononuclear cells. Subjects from which the peripheral blood mononuclear cells derive may be any subjects as long as they have the above MHC class II molecule. By culturing the peripheral blood mononuclear cells in the presence of a WT1 helper peptide, WT1-specific helper T cells are induced from precursor cells of helper T cells in the peripheral blood mononuclear cells. It is possible to treat or prevent hematopoietic organ tumors and solid cancers in a subject by administering the WT1-specific helper T cells obtained by the present invention to a subject having the above MHC class II molecule. In this connection, the peripheral blood mononuclear cells in the present specification include immature antigen presenting cells which are precursor cells of antigen presenting cells (for example, precursor cells of dendritic cells, B-lymphocytes, macrophages, etc.) Since the immature antigen presenting cells are contained, for example, in peripheral blood mononuclear cells and the like, such cells may be cultured in the presence of the above WT1 helper peptide.

In still another aspect, the present invention relates to a kit for inducing WT1-specific helper T cells, comprising the above WT1 helper peptide as an essential ingredient. Preferably, the kit is used in the above method for inducing WT1-specific helper T cells. The kit of the present invention may comprise, for example, an obtaining means of peripheral blood mononuclear cells, an adjuvant, a reaction vessel and others, in addition to the above WT1 helper peptide. In general, the kit is accompanied with an instruction manual. It is possible to induce WT1-specific helper T cells efficiently using the kit of the present invention.

In still another aspect, the present invention relates to a method for treating or preventing cancer, which comprises administering WT1-specific helper T cells to a subject having the above MHC class II molecule. The administration method of the WT1-specific helper T cells can be appropriately selected depending on conditions such as the type of diseases, the state of subjects, and the targeted sites. Examples of the administration method includes, but are not limited to, intravenous administration, intradermal administration, subcutaneous administration, intramuscular administration, transnasal administration, oral administration and the like.

Furthermore, the present invention relates to a kit for preventing or treating cancer, comprising the above WT1 helper peptide, WT1 polynucleotide, or WT1 expression vector as an essential ingredient. The kit is a kit characterized by induction of antigen presenting cells which display the above WT1 helper peptide through the above MHC class II molecule. Also, the kit of the present invention may comprise, for example, an obtaining means of samples, a reaction vessel and others, in addition to the above essential ingredient. In general, the kit is accompanied with an instruction manual. Antigen presenting cells which display a WT1 helper peptide through the above MHC class II molecule can be obtained efficiently using the kit of the present invention, and used for treating or preventing cancer by their administration.

In another aspect, the present invention relates to a method for determining the presence or amount of WT1-specific helper T cells in a subject having the above MHC class II molecule, said method comprising the steps of:

(a) reacting a complex of the above WT1 helper peptide with the above MHC class II molecule with a sample derived from the subject; and then (b) determining the presence or amount of helper T cells recognizing the complex contained in the sample.

Samples derived from subjects may be any samples as long as they have a possibility of containing lymphocytes and include, for example, body fluids such as blood and lymph fluid, tissues and the like. The complex of WT1 helper T cells with an MHC class II molecule may be, for example, in the form of tetramer, pentamer and the like, for example, using a method known to those skilled in the art such as a biotin-streptavidin method. The presence or amount of helper T cells recognizing such a complex can be determined by a method known to those skilled in the art. In this aspect of the present invention, the above complex may be labeled. As a label, known labels such as a fluorescent label and a radioactive label can be used. By labeling, the presence or amount of helper T cells can be determined simply and rapidly. Using a method of this aspect of the present invention, it becomes possible to make a diagnosis, a prognosis and the like of cancer.

Accordingly, the present invention also provides a composition comprising a complex of a WT1 helper peptide with the above MHC class II molecule for determining the presence or amount of WT1-specific helper T cells in a subject having the above MHC class II molecule.

Also, the present invention provides a kit comprising a complex of a WT1 helper peptide with the above MHC class II molecule for determining the presence or amount of WT1-specific helper T cells in a subject having the above MHC class II molecule.

In still another aspect, the present invention relates to a method for determining the presence or amount of WT1-specific helper T cells in a subject having the above MHC class II molecule, said method comprising the steps of:

(a) reacting the above WT1 helper peptide with a sample derived from the subject; and then (b) determining the presence or amount of a cytokine contained in the sample.

Samples derived from subjects may be any samples as long as they have a possibility of containing lymphocytes and include, for example, peripheral blood mononuclear cells, blood, body fluids, tissues and others, and preferably peripheral blood mononuclear cells. The reaction in the above step (a) can be carried out by reacting the above WT1 helper peptide in the above sample derived from a subject using a conventional technique. Culturing conditions of cells in a sample in each step can be determined properly by those skilled in the art. The presence or amount of a cytokine contained in a sample can be measured by a method known to those skilled in the art. The cytokine may be one capable of being induced by helper T cells such as interferon-γ and interleukin-10. In this aspect of the present invention, the above cytokine may be labeled. As a label, known labels such as a fluorescent label and a radioactive label can be used. Using the presence or amount of the above cytokine as an indicator, it becomes possible to determine the presence or amount of WT1-specific helper T cells simply and rapidly.

In further aspect, the present invention relates to a method for obtaining WT1-specific helper T cells using a complex of a WT1 helper peptide with the above MHC class II molecule, said method comprising the steps of:

(a) reacting a sample with the complex; and (b) obtaining helper T cells which are contained in the sample and recognize the complex.

The complex of a WT1 helper peptide with the above MHC class II molecule is as described above. Samples may be any samples as long as they have a possibility of containing lymphocytes and include, for example, subject-derived samples such as blood, cell culture solutions and the like. Obtainment of helper T cells recognizing the complex can be carried out, for example, using a method known to those skilled in the art such as FACS and MACS. It is possible to culture the resulting WT1-specific helper T cells and to use them for treating or preventing various cancers.

Accordingly, the present invention also relates to WT1-specific helper T cells, which can be obtained by a method for obtaining WT1-specific helper T cells using a complex of a WT1 helper peptide with the above MHC class II molecule.

Moreover, the present invention relates to a kit for obtaining WT1-specific helper T cells, comprising a complex of a WT1 helper peptide with the above MHC class II molecule.

In still another aspect, the present invention relates to a method for diagnosing cancer, which comprises using the above WT1-specific helper T cells, the above antigen presenting cells which display a WT1 helper peptide through the above MHC class II molecule, or the above WT1 antibody. Preferably, the WT1-specific helper T cells are used for the method for diagnosing cancer of the present invention. For example, the above helper T cells, antigen presenting cells or antibody can be incubated with a sample derived from a subject having the above MHC class II molecule, or administered to a subject having the above MHC class II molecule, and then, for example, the location, site, amount and the like of the helper T cells, antigen presenting cells or antibody can be determined to diagnose cancer. The above helper T cells, antigen presenting cells or antibody may be labeled. By labeling, it is possible to carry out the method for diagnosing cancer of the present invention efficiently.

In still another aspect, the present invention relates to a kit for diagnosing cancer, comprising the above WT1-specific helper T cells, antigen presenting cells which display a WT1 helper peptide through the above MHC class II molecule, or an antibody against a WT1 helper peptide or an antibody against a polynucleotide encoding the peptide, as an essential ingredient.

The present invention will be described specifically and described in detail below by way examples, but they should not be construed as limiting the present invention.

Example 1

Selection of Candidate WT1 Peptides Binding to MHC Class II Molecules

In order to search peptide sequences which bind to MHC class II molecules, a method as shown by Rammensee et al. was used (Rammensee et al, Immunogenetics 41:178-228, 1995). Specifically, selection was carried out using the programs described in the right end column in the Tables together with the law of Rammensee et al. By the method, $WT1_{3\ 5}$ peptides were narrowed down to peptide sequences as shown in Tables 1 and 2, $WT1_6$ peptides to peptide sequences as shown in Tables 3 and 4, and $WT1_{2\ 9\ 4}$ peptides to peptide sequences as shown in Tables 5 and 6. The left end column in Tables 1 to 6 shows "suitability" as a candidate peptide sequence. The more the number of "○" is, the higher the suitability is in the law of Rammensee et al. No mark shows poor suitability. Also, the group of amino acids in parenthesis of the column of "candidate peptide sequences binding to MHC class II molecules" in Tables 1 to 6 shows that one amino acid can be selected from the group of amino acids listed in the parenthesis. For example, the description [FLM] means one amino acid selected from the group of amino acids F, L and M. Also, the description [VYI(AL)] means one amino acid selected from the group of amino acids V, Y and I, or one amino acid selected from the group of amino acids A and L. "x" shows that it may be any amino acid. The right end column shows "program name" of programs used for listing candidate peptide sequences.

TABLE 1

Candidate peptide sequences binding to various MHC class II molecules (WT1₃₅ peptides)

| Suitability | Types of MHC class II molecules | Candidate peptide sequences binding to MHC class II molecules | Program name | SEQ ID NO: |
|---|---|---|---|---|
| ooo | DPA1*0102/DPB1*0201 | [FLMVWY]xxx[FLMY]xx[IAMV] | SYFPEITHI | 9 |
|  | DPA1*0103/DPB1*0201 | [YLVFK]xx[DSQT]x[YFWV]xx[LVI] | Marsh2000, Chicz 1997 | 10 |
| o | DPA1*0103/DPB1*0201 | [FLM]xxx[FL]xx[IA] | Marsh2000, Rotzschke 1994 | 11 |
| o | DPA1*0201/DPB1*0401 | [FLYM(IVA)]xxxxx[FLY(MVIA)]xx[VYI(AL)] | Marsh2000 | 12 |
| o | DPA1*0201/DPB1*0401 | [FLYMIVA]xxxxx[FLYMVIA]xx[VYIAL] | SYFPEITHI | 13 |
|  | DPA1*0201/DPB1*0901 | [RK]xxxx[AGL]xx[LV] | Marsh2000 | 14 |
|  | DPB1*0301 | x[R]xxxxxxx | Marsh2000 | 15 |
|  | DQA1:0101/DQB1*0501 | [L]xxx[YFW] | Marsh2000 | 16 |
| o | DQA1:0102/DQB1*0602 | xxxxx[LIV(APST)]xx[AGST(LIVP)] | Marsh2000 | 17 |
| o | DQA1:0301/DQB1*0301 | xx[AGST]x[AVLI] | Marsh2000 | 18 |
|  | DQA1:0301/DQB1*0301 | [DEW]xx[AGST]x[ACLM] | SYFPEITHI | 19 |
|  | DQA1:0301/DQB1*0302 | [RK]xxx[AG]xx[NED] | Marsh2000 | 20 |
| o | DQA1:0301/DQB1*0302 | [TSW]xxxxxxx[RE] | SYFPEITHI | 21 |
| ooo | DQA1:0501/DQB1*0201 | [FWYILV]xx[DELVIH]x[PDE(H)][ED]x[FYWVILM] | Marsh2000 | 22 |
| ooo | DQA1:0501/DQB1*0201 | [FWYILV]xx[DELVIH]x[PDEHPA][DE]x[FYWVILM] | SYFPEITHI | 23 |
| ooo | DQA1:0501/DQB1*0301 | [FYIMLV]xxx[VLIMY]x[YFMLVI] | Marsh2000 | 24 |
| o | DQA1:0501/DQB1*0301 | [WYAVM]xx[A]x[AIVTS]xxx[QN] | SYFPEITHI | 25 |
| ooo | DQB1*0602 | [AFCILMNQSTVWYDE]x[AFGILMNQSTWYCDE][AFGILMNQSTWY]x[LIVAPST]xx[ASTGLIVP] | SYFPEITHI | 26 |
| ooo | DRB1*0101 | [YFWLIMVA]xx[LMAIVN]x[AGSTCP]xx[LAIVNFYMW] | Marsh2000 | 27 |
| ooo | DRB1*0101 | [YVILFIAMW]xx[LAIVMNQ]x[AGSTCP]xx[LAIVNFY] | SYFPEITHI | 28 |
|  | DRB1*0102 | [ILVM]xx[ALM]x[AGSTCP]xx[ILAMYW] | Marsh2000 | 29 |
|  | DRB1*0102 | [ILVM]xx[ALM]x[AGSTP]xx[ILAMYW] | SYFPEITHI | 30 |
|  | DRB1*0301 | [LIFMV]xx[D]x[KR(EQN)]x[L][YLF] | Marsh2000, Malcherek 1993 | 31 |
|  | DRB1*0301 | [LIFMV]xx[D]x[KREQN]xx[YLF] | SYFPEITHI | 32 |
|  | DRB1*0301 or DRB3*0201 | [FILVY]xx[DNQT] | Marsh2000, Chicz 1992 | 33 |
|  | DRB1*0401 | [FLV]xxxxxxx[NQST] | Marsh2000 | 34 |
| ooo | DRB1*0401 or DRB4 | [FYWILVM]xx[FWILVADE]x[NSTQHR]xx[K] | Marsh2000, Friede 1996 | 35 |
| o | DRB1*0401 or DRB4*0101 | [FYW]xxxxxxx[ST] | Marsh2000, Verreck 1995 | 36 |

TABLE 1-continued

Candidate peptide sequences binding to various MHC class II molecules (WT1$_{35}$ peptides)

| Suitability | Types of MHC class II molecules | Candidate peptide sequences binding to MHC class II molecules | Program name | SEQ ID NO: |
|---|---|---|---|---|
| ooo | DRB1*0401 or DRB4*0101 | [FYWILVM]xx[PWILVADE]x[NSTQHR] DEHKNQRSTYACILMV]x[DEHKNQRSTYACILMV] | SYFPEITHI | 37 |
|  | DRB1*0402 or DRB4 | [VILM]xx[YFWILMRNH]x[NSTQHK]x [RKHNQP]x[H] | Marsh2000 | 38 |
|  | DRB1*0402 or DRB4 | [VILM]xx[YFWILMRN]x[NQSTK][RKHNQP]x [DEHLNQRSTYCILMVHA] | SYFPEITHI | 39 |
| oo | DRB1*0404 or DRB4 | [VILM]xx[FYWILVMADE]x[NTSQR]xx[K] | Marsh2000 | 40 |
| oo | DRB1*0404 or DRB4 | [VILM]xx[FYWILVMADE]x[NTSQR]xx[K] | SYFPEITHI | 40 |
| ooo | DRB1*0405 or DRB4 | [FYWVILM]xx[VILMDE]x[NSTQKD]xxx[DEQ] | Marsh2000 | 41 |
| ooo | DRB1*0405 or DRB4 | [FYWVILM]xx[VILMDE]x[NSTQKD]xxx[DEQ] | SYFPEITHI | 41 |
|  | DRB1*0405 or DRB4*0101 | [Y]xxxx[VT]xxx[D] | Marsh2000 | 42 |
| ooo | DRB1*0407 or DRB4 | [FYW]xx[AVTK]x[NTDS]xxx[QN] | Marsh2000 | 43 |
| ooo | DRB1*0407 or DRB4 | [FYW]xx[AVTK]x[NTDS]xxx[QN] | SYFPEITHI | 43 |

TABLE 2

Candidate peptide sequences binding to various MHC class II molecules (WT1$_{35}$ peptides)

| Suitability | Types of MHC class II molecules | Candidate peptide sequences binding to MHC class II molecules | Program name | SEQ ID NO: |
|---|---|---|---|---|
|  | DRB1*0701 | [FILVY]xxxx[NST] | Marsh2000 | 44 |
| o | DRB1*0701 | [FYWILV]xx[DEHKNQRSTY]x[NST]x[VILYF] | SYFPEITHI | 45 |
|  | DRB1*0801 | [FILTY]xxx[HKR] | Marsh2000 | 46 |
| o | DRB1*0901 or DRB4*0101 | [YFWL]xx[AS] | Marsh2000 | 47 |
| ooo | DRB1*0901 or DRB4*0101 | [WYFL]xx[AVS] | SYFPEITHI | 48 |
| ooo | DRB1*1101 | [YF]xx[LVMAFY]x[RKH1xx[AGSP] | Marsh2000 | 49 |
| ooo | DRB1*1101 | [WYF]xx[LVMAF]x[RKH]xx[AGSP] | SYFPEITHI | 50 |
|  | DRB1*1101 or DRB3*0202 | [YF]xxxx[RK]x[RK] | Marsh2000 | 51 |
| ooo | DRB1*1104 | [ILV]xx[LVMAFY]x[RKH]xx[AGSP] | Marsh2000 | 52 |
| ooo | DRB1*1104 | [ILV]xx[LVMAFY]x[RKH]xx[AGSP] | SYFPEITHI | 52 |
|  | DRB1*1201 or DRB3 | [ILFY(V)]x[LNM(VA)]xx[VY(FIN)]xx[YFM(IV)] | Marsh2000 | 53 |
|  | DRB1*1201 or DRB3 | [ILFYV]x[LMNVA]xx[VYFINA]xx[YFMIV] | SYFPEITHI | 54 |
| o | DRB1*1301 | [IVF]xx[YWLVAM]x[RK]xx[YFAST] | Marsh2000 | 55 |
| o | DRB1*1301 | [ILV]xx[LVMAWY]x[RK]xx[YFAST] | SYETEITHI | 56 |
|  | DRB1*1301 or DRB3*0101 | [ILV]xxxx[RK]xx[Y] | Marsh2000 | 57 |

TABLE 2-continued

Candidate peptide sequences binding to various MHC class II molecules (WT1$_{35}$ peptides)

| Suitability | Types of MHC class II molecules | Candidate peptide sequences binding to MHC class II molecules | Program name | SEQ ID NO: |
|---|---|---|---|---|
| ○ | DRB1*1302 | [YFVAI]xx[YWLVAM]x[RK]xx[YFAST] | Marsh2000 | 58 |
| ○ | DRB1*1302 | [YFVAI]xx[LVMAWY]x[RK]xx[YFAST] | SYFPEITHI | 59 |
|  | DRB1*1302 or DRB3*1301 | [ILFY]xxxx[RF]xx[Y] | Marsh2000 | 60 |
| ○ | DRB1*1501 | [LVI]xx[FYI]xx[ILVMF] | Marsh2000 | 61 |
| ○ | DRB1*1501 | [LVI]xx[FYI]xx[ILVMF] | SYFPEITHI | 61 |
|  | DRB1*1501 or DRB5*0101 | [ILV]xxxxxxxx[HKR] | Marsh2000 | 62 |
| ○ | DRB3*0202 | [YFIL]xx[N]x[ASPDE]xx[LVISG] | Marsh2000 | 63 |
| ○ | DRB3*0202 | [YFIL]xx[N]x[ASPDE]xx[LVISG] | SYFPEITHI | 63 |
| ○ | DRB3*0301 | [ILV]xx[N]x[ASPDE]xx[ILV] | Marsh2000 | 64 |
| ○ | DRB3*0301 | [ILV]xx[N]x[ASPDE]xx[ILV] | SYFPEITHI | 64 |
| ○○ | DRB5*0101 | [FYLM]xx[QVIM]xxxx[RK] | Marsh2000 | 65 |
| ○○ | DRB5*0101 | [FYLM]xx[QVIM]xxxx[RK] | SYFPEITHI | 65 |

TABLE 3

Candidate peptide sequences binding to various MHC class II molecules (WT1$_{186}$ peptides)

| Suitability | Types of MHC class II molecules | Serotype | Candidate peptide sequences binding to MHC class II molecules | Program name | SEQ ID NO: |
|---|---|---|---|---|---|
|  | DPA1*0102/ DPB1*0201 | DPw2 | unknown | Marsh2000 |  |
|  | DPA1*0102/ DPB1*0201 | DPw2 | [FLMVWY]-x-x-x-[FLMY]-x-x-[IAMV] | SYFPEITHI | 9 |
|  | DPA1*0103/ DPB1*0201 | DPw2 | [FLM]-x-x-x-[FL]-x-x-[IA] | Marsh2000 | 11 |
| ○ | DPA1*0103/ DPB1*0201 | DPw2 | [YLVFK]-x-x-[DSQT]-x-[YFWV]-x-x-[LVI] | Marsh2000 | 10 |
|  | DPA1*0103/ DPB1*0201 | DPw2 | unknown | SYFPEITHI |  |
|  | DPA1*0103/ DPB1*0201 | DPw2 | unknown | SYFPEITHI |  |
| ○○ | DPA1*0201/ DPB1*0401 | DPw4 | [FLYM(IVA)]-x-x-x-x-x-[FLY(MVIA)]-x-x-[VYI(AL)] | Marsh2000 | 12 |
| ○○ | DPA1*0201/ DPB1*0401 | DPw4 | [FLYMIVA]-x-x-x-x-x-[FLYMVIA]-x-x-[VYIAL] | SYFPEITHI | 13 |
| ○○○ | DPA1*0201/ DPB1*0901 |  | [RK]-x-x-x-x-[AGL]-x-x-[LV] | Marsh2000 | 14 |
|  | DPB1*0301 | DPw3 | x-[R]-x-x-x-x-x-x-x | Marsh2000 | 15 |
|  | DPB1*0301 | DPw3 | unknown | SYFPEITHI |  |
|  | DQA1*0101/ DQB1*0501 | DQ5(1) | [L]-x-x-x-[YFW] | Marsh2000 | 16 |
|  | DQA1*0101/ DQB1*0501 | DQ5(1) | unknown | SYFPEITHI |  |

TABLE 3-continued

Candidate peptide sequences binding to various MHC class II molecules (WT1_186 peptides)

| Suitability | Types of MHC class II molecules | Serotype | Candidate peptide sequences binding to MHC class II molecules | Program name | SEQ ID NO: |
|---|---|---|---|---|---|
| ooo | DQA1*0102/ DQB1*0602 | DQ6(1) | x-x-x-x-[LIV(APST)]-x-x-[AGST(LIVP)] | Marsh2000 | 17 |
|  | DQA1*0301/ DQB1*0301 | DQ7(3) | x-x-[AGST]-x-[AVLI] | Marsh2000 | 18 |
| ooo | DQA1*0301/ DQB1*0301 | DQ7(3) | [DEW]-x-x-[AGST]-x-[ACLM] | SYFPEITHI | 19 |
| o | DQA1*0301/ DQB1*0302 | DQ8(3) | [RK]-x-x-x-x-[AG]-x-x-[NED] | Marsh2000 | 66 |
|  | DQA1*0301/ DQB1*0201 | DQ8(3) | [TSW]-x-x-x-x-x-x-[RE] | SYFPEITHI | 21 |
| ooo | DQA1*0501/ DQB1*0201 | DQ2 | [FWYILV]-x-x-[DELVIH]-x-[PDE(H)]-[ED]-x-[FYWVILM] | Marsh2000 | 22 |
| ooo | DQA1*0501/ DQB1*0201 | DQ2 | [FWYILV]-x-x-[DELVIH]-x-[PDEHPA]-[DE]-x-[FWYILVM] | SYFPEITHI | 67 |
| oo | DQA1*0501/ DQB1*0301 | DQ7(3) | [FYIMLV]-x-x-x-[VLIMY]-x-[YFMLVI] | Marsh2000 | 24 |
| o | DQA1*0501/ DQB1*0301 | DQ7(3) | [WYAVM]-x-x-[A]-x-[AIVTS]-x-x-x-[QN] | SYFPEITHI | 25 |
| ooo | DQB1*0602 | DQ6(1) | [AFCILMNQSTVWYDE]-x-[AFGILMNQSTVWYCDE]-[AFGILMNQSTVWY]-x-[LIVAPST]-x-x-[ASTGLIVP] | SYFPEITHI | 68 |
| ooo | DRB1*0101 | DR1 | [YFWLIMVA]-x-x-[LMAIVN]-x-[AGSTCP]-x-x-[LAIVNFYMW] | Marsh2000 | 27 |
| ooo | DRB1*0101 | DR1 | [YVLFIAMW]-x-x-[LAIVMNQ]-x-[AGSTCP]-x-x-[LAIVNFY] | SYFPEITHI | 28 |
| ooo | DRB1*0102 | DR1 | [ILVM]-x-x-[ALM]-x-[AGSTCP]-x-x-[ILAMYW] | Marsh2000 | 29 |
| ooo | DRB1*0102 | DR1 | [ILVM]-x-x-[ALM]-x-[AGSTP]-x-x-[ILAMYW] | SYFPEITHI | 30 |
| oo | DRB1*0301 | DR17(3) | [LIFMV]-x-x-[D]-x-[KR(EQN)]-x-[L]-[YLF] | Marsh2000 | 31 |
| oo | DRB1*0301 | DR17(3) | [LIFMV]-x-x-[D]-x-[KREQN]-x-x-[YLF] | SYFPEITHI | 32 |
|  | DRB1*0301 or DRB3*0201 | DR17(3) | [FILVY]-x-x-[DNQT] | Marsh2000 | 33 |
|  | DRB1*0301 or DRB3*0201 | DR17(3) | unknown | SYFPEITHI |  |
|  | DRB1*0401 | DR4 | [FLV]-x-x-x-x-x-x-[NQST] | Marsh2000 | 34 |
|  | DRB1*0401 | DR4 | unknown | SYFPEITHI |  |
| oo | DRB1*0401 or DRB4 | DR4 | [FYWILVM]-x-x-[FWILVADE]-x-[NSTQHR]-x-x-[K] | Marsh2000 | 35 |
|  | DRB1*0401 or DRB4*0101 | DR4 | [FYW]-x-x-x-x-x-x-[ST] | Marsh2000 | 36 |
| ooo | DRB1*0401 or DRB4*0101 | DR4 | [FYWILVM]-x-x-[PWILVADE]-x-[NSTQHR]-[DEHKNQRSTYACILMV]-x-[DEHMQRSTYACILMV] | SYFPEITHI | 37 |
| oo | DRB1*0402 or DRB4 | DR4 | [VILM]-x-x-[YFWILMRNH]-x-[NSTQHK]-x-[RKHNQP]-x-[H] | Marsh2000 | 38 |
| ooo | DRB1*0402 or DRB4 | DR4 | [VILM]-x-x-[YFWILMRN]-x-[NOTK]-[RKHNQP]-x-[DEHLWRSTYCILMVHA] | SYFPEITHI | 39 |

TABLE 4

Candidate peptide sequences binding to various MHC class II molecules (WT1$_{186}$ peptides)

| Suitability | Types of MHC class II molecules | Serotype | Candidate peptide sequences binding to MHC class II molecules | Program name | SEQ ID NO: |
|---|---|---|---|---|---|
| ○ | DRB1*0404 or DRB4 | DR4 | [VILM]-x-x[FYWILVMADE]-x-[NTSQR]-x-x-[K] | Marsh2000 | 40 |
| ○ | DRB1*0404 or DRB4 | DR4 | [VILM]-x-x[FYWILVMADE]-x-[NTSQR]-x-x-[K] | SYFPEITHI | 40 |
| ○ | DRB1*0405 or DRB4 | DR4 | [FYWVILM1-x-x-[VILMDE]-x-[NSTQKD]-x-x-x-[DEQ] | Marsh2000 | 41 |
| ○ | DRB1*0405 or DRB4 | DR4 | [FYWVILM]-x-x-IVILMDE]-x-[NSTQKD]-x-x-x-[DEQ] | SYFPEITHI | 41 |
|  | DRB1*0405 or DRB4*0101 | DR4 | [Y]-x-x-x-x-[VT]-x-x-x-[D] | Marsh2000 | 42 |
|  | DRB1*0405 or DRB4*0101 | DR4 | unknown | SYFPEITHI |  |
|  | DR31*0407 or DRB4 | DR4 | [FYW]-x-x-[AVTK]-x-[NTDS]-x-x-x-[QN] | Marsh2000 | 43 |
|  | DRB1*0407 or DRB4 | DR4 | [FYW]-x-x-[AVK]-x-[NTDS]-x-x-x-[QN] | SYFPEITHI | 69 |
|  | DRB1*0701 | DR7 | [FILVY]-x-x-x-x-[NST] | Marsh2000 | 44 |
| ○ | DRB1*0701 | DR7 | [FYWILV]-x-x-[DEHKNQRSTY]-x-[NST]-x-x-[VILYF] | SYFPEITHI | 70 |
|  | DRB1*0801 | DR8 | [FILVY]-x-x-x-[HKR] | Marsh2000 | 46 |
|  | DRB1*0801 | DR8 | unknown | SYFPEITHI |  |
|  | DRB1*0901 or DRB4*0101 | DR9 | [YFWL]-x-x-[AS] | Marsh2000 | 47 |
|  | DRB1*0901 or DRB4*0101 | DR9 | [WYFL]-x-x-[AVS] | SYFPEITHI | 48 |
| ∞ | DRB1*1101 | DR11(5) | [YF]-x-x-[LVMAFY]-x-[RKH]-x-x-[AGSP] | Marsh2000 | 49 |
| ∞ | DRB1*1101 | DR11(5) | [WYF]-x-x-[LVMAFY]-x-[RKH]-x-x-[AGSP] | SYFPEITHI | 71 |
|  | DRB1 1101 or DRB3*0202 | DR11(5) | [YF]-x-x-x-x-[RK]-x-[RK] | Marsh2000 | 51 |
| ○ | DRB1*1104 | DR11(5) | [ILV]-x-x-[LVMAFY-x-[RKH]-x-x-[AGSP] | Marsh2000 | 52 |
| ○ | DRB1*1104 | DR11(5) | [ILV]-x-x-[LVMAFY]-x-[RKH]-x-x-[AGSP] | SYFPEITHI | 52 |
|  | DRB1*1201 or DRB3 | DR12(5) | [ILFY(V)]-x-[LNM(VA)]-x-x-[VY(FIN)]-x-x-[YFM(IV)] | Marsh2000 | 53 |
| ∞ | DRB1*1201 or DRB3 | DR12(5) | [ILFYV]-x-LLMNVA]-x-x-[VYFINA]-x-x-[YFMIV] | SYFPEITHI | 54 |
| ○ | DRB1*1301 | DR13(6) | [IVF]-x-x-[YWLVAM]-x-[RK]-x-x-[YFAST] | Marsh2000 | 55 |
| ○ | DRB1*1301 | DR13(6) | [IVF]-x-x-[LVMAWY]-x-[RK]-x-x-[YFAST] | SYFPEITHI | 72 |
|  | DRB1*1301 or DRB3*0101 | DR13(6) | [ILV]-x-x-x-x-[RK]-x-x-[Y] | Marsh2000 | 57 |
|  | DRB1*1301 or DRB3*0101 | DR13(6) | unknown | SYFPEITHI |  |
| ○ | DRB1*1302 | DR13(6) | [YFVAI]-x-x-[YWLVAM]-x-[RK]-x-x-[YFAST] | Marsh2000 | 58 |
| ○ | DRB1*1302 | DR13(6) | [YFVAI]-x-x-[LVMAWY]-x-[RK]-x-x-[YFAST] | SYFPEITHI | 59 |
|  | DRB1*1302 or DRB3*0301 | DR13(6) | [ILFY]-x-x-x-x-[RK]-x-x-[Y] | Marsh2000 | 60 |
|  | DRB1*1302 or DRB3*0301 | DR13(6) | unknown | SYFPEITHI |  |

TABLE 4-continued

Candidate peptide sequences binding to various MHC class II molecules (WT1$_{186}$ peptides)

| Suitability | Types of MHC class II molecules | Serotype | Candidate peptide sequences binding to MHC class II molecules | Program name | SEQ ID NO: |
|---|---|---|---|---|---|
| ○ | DRB1*1501 | DR15(2) | [LVI]-x-x-[FYI]-x-x-[ILVMF] | Marsh2000 | 61 |
| ○ | DRB1*1501 | DR15(2) | [LVI]-x-x-[FYI]-x-x-[ILVMF] | SYFPEITHI | 61 |
| ○ | DRB1*1501 or DRB5*0101 | DR15(2) | [ILV]-x-x-x-x-x-x-x-[HKR] | Marsh2000 | 62 |
| ○○○ | DRB3*0202 | DR52 | [YFIL]-x-x-[N]-x-[ASPDE]-x-x-[LVISG] | Marsh2000 | 63 |
| ○○○ | DRB3*0202 | DR52 | [YFIL]-x-x-[N]-x-[ASPDE]-x-x-[LVISG] | SYFPEITHI | 63 |
| ○○○ | DRB3*0301 | DR52 | [ILV]-x-x-[N]-x-[ASPDE]-x-x-[ILV] | Marsh2000 | 64 |
| ○○○ | DRB3*0301 | DR52 | [ILV]-x-x-[N]-x-[ASPDE]-x-x-[ILV] | SYFPEITHI | 64 |
| | DRB5*0101 | DR51 | [FYLM]-x-x-[QVIM]-x-x-x-x-[RK] | Marsh2000 | 65 |
| | DRB5*0101 | DR51 | [FYLM]-x-x-[QVIM]-x-x-x-x-[RK] | SYFPEITHI | 65 |

TABLE 5

Candidate peptide sequences binding to various MHC class II molecules (WT1$_{294}$ peptides)

| Suitability | Types of MHC class II molecules | Serotype | Candidate peptide sequences binding to MHC class II molecules | Program name | SEQ ID NO: |
|---|---|---|---|---|---|
| | DPA1*0102/ DPB1*0201 | DPw2 | unknown | Marsh2000 | |
| ○○ | DPA1*0102/ DPB1*0201 | DPw2 | [FLMVWY]-x-x-x-[FLMY]-x-x-[IAMV] | SYFPEITHI | 9 |
| ○ | DPA1*0103/ DPB1*0201 | DPw2 | [FLM]-x-x-x-[FL]-x-x-[IA] | Marsh2000 | 11 |
| ○ | DPA1*0103/ DPB1*0201 | DPw2 | [YLVFK]-x-x-[DSQT]-x-[YFWV]-x-x-[LVI] | Marsh2000 | 10 |
| | DPA1*0103/ DPB1*0201 | DPw2 | unknown | SYFPEITHI | |
| | DPA1*0103/ DPB1*0201 | DPw2 | unknown | SYFPEITHI | |
| ○○○ | DPA1*0201/ DPB1*0401 | DPw4 | [FLYM(IVA)]-x-x-x-x-x-[FLY(MVIA)]-x-x-[VYI(AL)] | Marsh2000 | 12 |
| ○○○ | DPA1*0201/ DPB1*0401 | DPw4 | [FLYMIVA]-x-x-x-x-x-[FLYMVIA]-x-x-[VYIAL] | SYFPEITHI | 13 |
| | DPA1*0201/ DPB1*0901 | | [RK]-x-x-x-x-[AGL]-x-x-[LV] | Marsh2000 | 14 |
| ○ | DPB1*0301 | DPw3 | x-[R]-x-x-x-x-x-x-x | Marsh2000 | 15 |
| | DPB1*0301 | DPw3 | unknown | SYFPEITHI | |
| | DQA1*0101/ DQB1*0501 | DQ5(1) | [L]-x-x-x-[YFW] | Marsh2000 | 16 |
| | DQA1*0101/ DQB1*0501 | DQ5(1) | unknown | SYFPEITHI | |
| | DQA1*0102/ DQB1*0602 | DQ6(1) | x-x-x-x-[LIV(APST)]-x-x-[AGST(LIVP)] | Marsh2000 | 17 |
| | DQA1*0301/ DQB1*0301 | DQ7(3) | x-x-[AGST]-x-[AVLI] | Marsh2000 | 18 |

TABLE 5-continued

Candidate peptide sequences binding to various MHC class II molecules (WT1$_{294}$ peptides)

| Suitability | Types of MHC class II molecules | Serotype | Candidate peptide sequences binding to MHC class II molecules | Program name | SEQ ID NO: |
|---|---|---|---|---|---|
| | DQA1*0301/ DQB1*0301 | DQ7(3) | [DEW]-x-x-[AGST]-x-[ACLM] | SYFPEITHI | 19 |
| | DQA1*0301/ DQB1*0302 | DQ8(3) | [RK]-x-x-x-x-[AG]-x-x-[NED] | Marsh2000 | 66 |
| ○ | DQA1*0301/ DQB1*0302 | DQ8(3) | [TSW]-x-x-x-x-x-x-[RE] | SYFPEITHI | 21 |
| ○○○ | DQA1*0501/ DQB1*0201 | DQ2 | [FWYILV]-x-x-[DELVIH]-x-[PDE(H)]-[ED]-x-[FYWVILM] | Marsh2000 | 22 |
| ○○○ | DQA1*0501/ DQB1*0201 | DQ2 | [FWYILV]-x-x-[DELVIH]-x-[PDEHPA]-[DE]-x-[FWYILVM] | SYFPEITHI | 67 |
| ○○○ | DQA1*0501/ DQB1*0301 | DQ7(3) | [FYIKLV]-x-x-x-[VLIMY]-x-[YFMLVI] | Marsh2000 | 24 |
| | DQA1*0501/ DQB1*0301 | DQ7(3) | [WYAVM]-x-x-[A[-x-[AIVTS]-x-x-x-[QN] | SYFPEITHI | 25 |
| ○○○ | DQB1*0602 | DQ6(1) | [AFCILMNQSTVWYDE]-x-[AFGILMNQSTVWYCDE]-[AFGILMNQSTVWY]-x-[LIVAPST]-x-x-[ASTGLIVP] | SYFPEITHI | 68 |
| ○○○ | DRB1*0101 | DR1 | [YFWLIMVA]-x-x-[LMAIVN]-x-[AGSTCP]-x-x-[LAIVNFYMW] | Marsh2000 | 27 |
| ○○○ | DRB1*0101 | DR1 | [YVLFIAMW]-x-x-[LAIVMNQ]-x-[AGSTCP]-x-x-[LAIVNFY] | SYFPEITHI | 28 |
| | DRB1*0102 | DR1 | [ILVM]-x-x-[ALM]-x-[AGSTCP]-x-x-[ILAMYW] | Marsh2000 | 29 |
| | DRB1*0102 | DR1 | [ILVM]-x-x-[ALM]-x-[AGSTP]-x-x-[ILAMYW] | SYFPEITHI | 30 |
| ○○ | DRB1*0301 | DQ17(3) | [LIFMV]-x-x-[D]-x-[KR(EQN)]-x-[L]-YLF] | Marsh2000 | |
| ○○ | DRB1*0301 | DQ17(3) | [LIFMV]-x-x-[D[-x-[KREQN]-x-x-[YLF] | SYFPEITHI | 32 |
| ○○ | DRB1*0301 or DRB3*0201 | DQ17(3) | [FILVY]-x-x-[DNQT] | Marsh2000 | 33 |
| | DRB1*0301 or DRB3*0201 | DQ17(3) | unknown | SYFPEITHI | |
| ○○ | DRB1*0401 | DR4 | [FLV]-x-x-x-x-x-x-[NQST] | Marsh2000 | 34 |
| | DRB1*0401 | DR4 | unknown | SYFPEITHI | |
| ○○○ | DRB1*0401 or DRB4 | DR4 | [FYWILVM]-x-x-[FWILVADE]-x-[NSTQHR]-x-x-[K] | Marsh2000 | 35 |
| ○○ | DRB1*0401 or DRB4*0101 | DR4 | [FYW]-x-x-x-x-x-x-[ST] | Marsh2000 | 36 |
| ○○○ | DRB1*0401 or DRB4*0101 | DR4 | [FYWILVM]-x-x-[PWILVADE]-x-[NSTQHR]-[DEHKNQRSTYACILMV]-x-[DEHKNQRSTYACILMV]+ | SYFPEITHI | 37 |
| ○○○ | DRB1*0402 or DRB4 | DR4 | [VILM]-x-x-[YFWILMRNH]-x-[NSTQHK]-x-[RKHNQP]-x-[H] | Marsh2000 | 38 |
| ○○○ | DRB1*0402 or DRB4 | DR4 | [VILM]-x-x-[YFWILMRN]-x-[NQSTK]-[RKHNQP]-x-[DEHLNQRSTYCILMVHA] | SYFPEITHI | 39 |

TABLE 6

Candidate peptide sequences binding to various MHC class II molecules (WT1₂₉₄ peptides)

| Suitability | Types of MHC class II molecules | Serotype | Candidate peptide sequences binding to MHC class II molecules | Program name | SEQ ID NO: |
|---|---|---|---|---|---|
| ○ | DRB1*0404 or DRB4 | DR4 | [VILM]-x-x-[FYWILVMADE]-x-[NTSQN-x-x-[K] | Marsh2000 | 40 |
| ○ | DRB1*0404 or DRB4 | DR4 | [VILM]-x-x-[FYWILVMADE]-x-[NTSQR-x-x-[K] | SYFPEITHI | 40 |
| ○○○ | DRB1*0405 or DRB4 | DR4 | [FYWVILM]-x-x-[VILMDE]-x-[NSTQKD]-x-x-x-[DEQ] | Marsh2000 | 41 |
| ○○○ | DRB1*0405 or DRB4 | DR4 | [FYWVILM]-x-x-[VILMDE]-x-[NSTQKD]-x-x-x-[DEQ] | SYFPEITHI | 41 |
|  | DRB1*0405 or DRB4*0101 | DR4 | [Y]-x-x-x-x-[VT]-x-x-x-[D] | Marsh2000 | 42 |
|  | DRB1*0405 or DRB4*0101 | DR4 | unknown | SYFPEITHI |  |
| ○○○ | DRB1*0407 or DRB4 | DR4 | [FYW]-x-x-[-AVTK]-x-[NTDS]-x-x-x-[QN] | Marsh2000 | 43 |
| ○○○ | DRB1*0407 or DRB4 | DR4 | [FYW]-x-x-[AVK]-x-[NTDS]-x-x-x-[QN] | SYFPEITHI | 69 |
| ○ | DRB1*0701 | DR7 | [FILVY]-x-x-x-x-[NST] | Marsh2000 | 44 |
| ○ | DRB1*0701 | DR7 | [FYWILV]-x-x-[DEHKNQRSTY]-x-[NST]-x-x-[VILYF] | SYFPEITHI | 70 |
| ○ | DRB1*0801 | DRB | [FILVY]-x-x-x-[HKR] | Marsh2000 | 46 |
|  | DRB1*0801 | DRB | unknown | SYFPEITHI |  |
| ○ | DRB1*0901 or DRB4*0101 | DR9 | [YFWL]-x-x-[AS] | Marsh2000 | 47 |
| ○ | DRB1*0901 or DRB4*0101 | DR9 | [WYFL]-x-x-[AVS] | SYFPEITHI | 48 |
| ○○ | DRB1*1101 | DR11(5) | [YF]-x-x-[LVMAFY]-x-[RKH]-x-x-[AGSP] | Marsh2000 | 49 |
| ○○ | DRB1*1101 | DR11(5) | [WYF]-x-x-[LVMAFY]-x-[RKH]-x-x-[AGSP] | SYFPEITHI | 71 |
| ○○○ | DRB1*1101 or DRB3*0202 | DR11(5) | [YF]-x-x-x-x-[RK]-x-[RK] | Marsh2000 | 51 |
|  | DRB1*1104 | DR11(5) | [ILV]-x-x-[LVMAFY]-x-[RKH]-x-x-[AGSP] | Marsh2000 | 52 |
|  | DRB1*1104 | DR11(5) | [ILV]-x-x-[LVMAFY]-x-[RKH]-x-x-[AGSP] | SYFPEITHI | 52 |
| ○○ | DRB1*1201 or DRB3 | DR12(5) | [ILFY(V)]-x-[LNM(VA)]-x-x-[VY(FIN)]-x-x-[YFM(IV)] | Marsh2000 | 53 |
| ○○ | DRB1*1201 or DRB3 | DR12(5) | [ILFYV]-x-[LMNVA]-x-x-[VYFINA]-x-x-[YFMIV] | SYFPEITHI | 54 |
|  | DRB1*1301 | DR13(6) | [IVF]-x-x-[YWLVAM]-x-[RK]-x-x-[YFAST] | Marsh2000 | 55 |
|  | DRB1*1301 | DR13(6) | [ILV]-x-x-[LVMAWY]-x-[RK]-x-x-[YFAST] | SYFPEITHI | 56 |
|  | DRB1*1301 or DRB3*0101 | DR13(6) | [ILV]-x-x-x-x-[RK]-x-x-[Y] | Marsh2000 | 57 |
|  | DRB1*1301 or DRB3*0101 | DR13(6) | unknown | SYFPEITHI |  |
| ○ | DRB1*1302 | DR13(6) | [YFVAI]-x-x-[YWLVAM]-x-[RK]-x-x-[YEAST] | Marsh2000 | 73 |
| ○ | DRB1*1302 | DR13(6) | [YFVAI]-x-x-[LVMAWY]-x-[RK]-x-x-[YEAST] | SYFPEITHI | 74 |

TABLE 6-continued

Candidate peptide sequences binding to various MHC class II molecules (WT1₂₉₄ peptides)

| Suitability | Types of MHC class II molecules | Serotype | Candidate peptide sequences binding to MHC class II molecules | Program name | SEQ ID NO: |
|---|---|---|---|---|---|
| ○ | DRB1*1302 or DRB3*0301 | DR13(6) | [ILFY]-x-x-x-x-[RK]-x-x-[Y] | Marsh2000 | 60 |
| | DRB1*1302 or DRB3*0301 | DR13(6) | unknown | SYFPEITHI | |
| ∞ | DRB1*1501 | DR15(2) | [LVI]-x-x-[FYI]-x-x-[ILVMF] | Marsh2000 | 61 |
| ∞ | DRB1*1501 | DR15(2) | [LVI]-x-x-[FYI]-x-x-[ILVMF] | SYFPEITHI | 61 |
| | DRB1*1501 or DRB5*0101 | DR15(2) | [ILV]-x-x-x-x-x-x-x-[HKR] | Marsh2000 | 62 |
| ○○○ | DRB3*0202 | DR52 | [YFIL]-x-x-[N]-x-[ASPDE]-x-x-[LVISG] | Marsh2000 | 63 |
| ○○○ | DRB3*0202 | DR52 | [YFIL]-x-x-[N]-x-[ASPDE]-x-x-[LVISG] | SYFPEITHI | 63 |
| ○ | DRB3*0301 | DR52 | [ILV]-x-x-[N]-x-[ASPDE]-x-x-[ILV] | Marsh2000 | 64 |
| ○ | DRB3*0301 | DR52 | [ILV]-x-x-[N]-x-[ASPDE]-x-x-[ILV) | SYFPEITHI | 64 |
| ○○○ | DRB5*0101 | DR51 | [FYLM]-x-x-[QVIM]-x-x-x-x-[RK] | Marsh2000 | 65 |
| ○○○ | DRB5*0101 | DR51 | [FYLM]-x-x-[QVIM]x x x x[RK] | SYFPEITHI | 65 |

Next, candidate WT1 peptides were visually selected from Tables 1 to 6, peptides as shown in the following Table 7 were identified as preferred candidate peptides for MHC class II molecules, and actual functions of these peptides were analyzed as described below.

TABLE 7

Identification of peptide candidates for mouse MHC class II molecules

| | | | |
|---|---|---|---|
| WT1₃₅ | WAPVLDFAPPGASAYGSL (SEQ ID NO: 3) | 18 mer | MW 1819.01 |
| WT1₈₆ | EQCLSAFTLHFSGQFTG (SEQ ID NO: 6) | 17 mer | MW 1944.01 |
| WT1₂₉₄ | FRGIQDVRRVSGVAPTLVR (SEQ ID NO: 7) | 19 mer | MW 2126.48 |

Preparation of WT1 Peptide-Specific Cell Lines and Measurement of Cell Proliferation Ability First, the above WT1 peptides were emulsified with a Freund's incomplete adjuvant (Montanide ISA 51), and mice were intradermally inoculated with each WT1 peptide in an amount corresponding to 100 μg/mouse. The immunization was carried out 3 times at intervals of one week, the spleen was removed after 1 week of the final immunization, and spleen cells were prepared. The spleen cells were stimulated 3 times at intervals of 10 days using spleen cells of non-immunized mice, which were pulsed with the same WT1 peptide as that used for immunization of each mouse and irradiated, as a stimulator. Then, the 4th stimulation was carried out using spleen cells of non-immunized mice, which were pulsed with each peptide (WT1₃₅, WT1₈₆ or WT1₂₉₄ peptide) as shown in Table 7 and irradiated, as a stimulator, and proliferation reaction in response to each stimulator was measured by a $^3$H incorporation experiment.

An OVA (ovalbumin) peptide irrelevant to WT1 peptides was used as a control peptide. As a result, mouse spleen cells immunized with a WT1₃₅ peptide, a WT1₈₆ peptide or a WT1₂₉₄ peptide each responded to the stimulator pulsed with a WT1₃₅ peptide, a WT1₈₆ peptide or a WT1₂₉₄ peptide, and proliferated (FIG. 1A to 1C).

As described above, spleen cells were stimulated in vitro 3 times at intervals of 10 days using spleen cells of non-immunized mice, which were pulsed with each WT1 peptide and irradiated. When the 4th stimulation was then carried out using spleen cells of non-immunized mice, which were pulsed with each peptide described above and irradiated, as a stimulator, and proliferation reaction was measured, an MHC class I antibody ($D^b$ antibody) or an MHC class II antibody (Ab antibody) was added to the culture solution and $^3$H incorporation was measured. As a result, the proliferation reaction in response to the stimulator pulsed with each of a WT1₃₅ peptide, a WT1₈₆ peptide and a WT1₂₉₄ peptide was suppressed by the addition of an MHC class II antibody (FIG. 2A to 2C).

As described above, spleen cells were stimulated in vitro 3 times at intervals of 10 days using spleen cells of non-immunized mice, which were pulsed with each WT1 peptide and irradiated. Then, the proliferation reaction was measured by $^3$H incorporation using irradiated C1498 cells not expressing any WT1 protein, C1498 cells pulsed with each of the above WT1 peptides, or C1498 cells expressing a WT1 protein by introduction of a WT1 gene, as a stimulator.

As a result, the proliferation reaction was produced in response to C1498 cells pulsed with the same WT1 peptide as that used in immunization in vivo and C1498 cells expressing a WT1 protein by introduction of a WT1 gene (FIG. 3). This revealed that a WT1₃₅ peptide, a WT1₈₆ peptide and a WT1₂₉₄ peptide are produced by an intracellular process of an endogenous WT1 protein and displayed on an MHC class II molecule. From the above facts, it was shown that these three WT1 peptides are MHC class II-restricted WT1 peptides.

Measurement of IFN-γ Producing Ability

Figure 4:
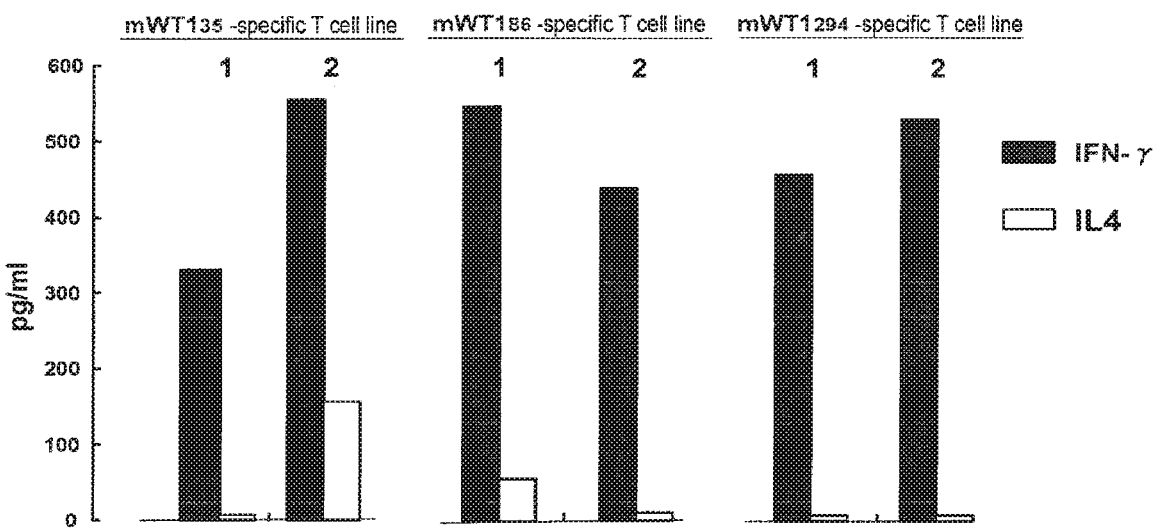
FIG. 4 shows the results obtained by measuring an IFN-γ producing ability in each peptide-specific T cell line prepared by pulsing with three peptides (mWT1$_{3\ 5}$, mWT1$_{8\ 6}$, and mWT1$_{2\ 9\ 4}$).

As described above, spleen cells were stimulated in vitro 3 times at intervals of 10 days using spleen cells of non-immunized mice, which were pulsed with each WT1 peptide and irradiated. Then, the concentration of IFN-γ and IL-4 in a culture supernatant was measured using an ELISA kit (BIOSOURCE Immunoassay Kit, Invitrogen). As a result, spleen cells of two separate mice responded to spleen cells of non-immunized mice which were pulsed with each WT1 peptide and irradiated, and produced interferon-γ but little interleukin-4 (FIG. 4). This revealed that these three types of WT1 peptides induce Th1 type of WT1-specific helper T cells.

Example 2

Measurement of WT1-Specific Cytotoxic T Cells (CTLs)

Figure 5:
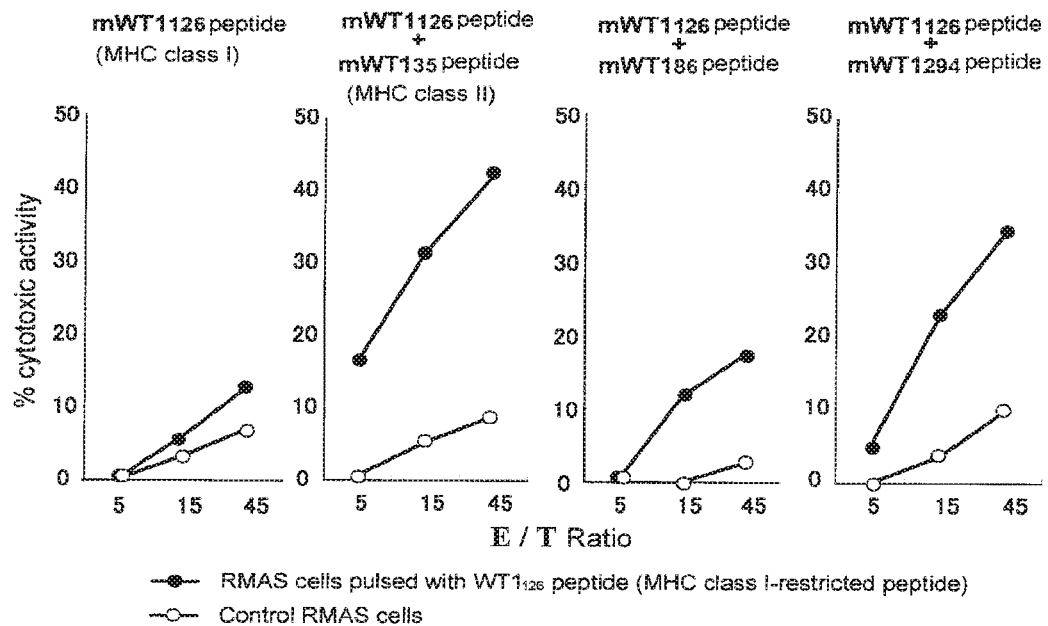
FIG. 5 shows the results obtained by measuring a CTL cytotoxic activity of three peptides (mWT1$_{3\ 5}$, mWT1$_{8\ 6}$, and mWT1$_{2\ 9\ 4}$). ● shows the results of experiments carried out using RMAS cells pulsed with a WT1$_{1\ 2\ 6}$ peptide (MHC class I-restricted peptide). ○ shows the results of experiments carried out using control RMAS cells.

Mice were immunized 3 times with a $WT1_{1\ 2\ 6}$ peptide (MHC class I) alone, a $WT1_{1\ 2\ 6}$ peptide (MHC class I)+a $WT1_{3\ 5}$ peptide (MHC class II), a $WT1_{1\ 2\ 6}$ peptide (MHC class I)+a $WT1_{8\ 6}$ peptide (MHC class II), or a $WT1_{1\ 2\ 6}$ peptide (MHC class I)+a $WT1_{2\ 9\ 4}$ peptide (MHC class II), and spleen cells of the mice were prepared. Then, the spleen cells were stimulated once in vitro using a $WT1_{1\ 2\ 6}$ peptide (MHC class I), and on 6th day, cytotoxic activity was measured using RMAS cells pulsed with a $WT1_{1\ 2\ 6}$ peptide (MHC class I) as a target cell. RMAS cells not pulsed with a $WT1_{1\ 2\ 6}$ peptide (MHC class I) were used as a control target cell. As a result, mouse spleen cells immunized with a $WT1_{1\ 2\ 6}$ peptide (MHC class I)+a WT1 helper peptide (MHC class II) induced WT1-specific cytotoxic T cells more strongly as compared with mouse spleen cells immunized with a $WT1_{1\ 2\ 6}$ peptide (MHCI class I) alone (FIG. 5). This demonstrated that the three WT1 peptides (MHC class II) are a WT1-specific helper peptides.

Example 3

Tumor Implantation Experiment

Figure 6:
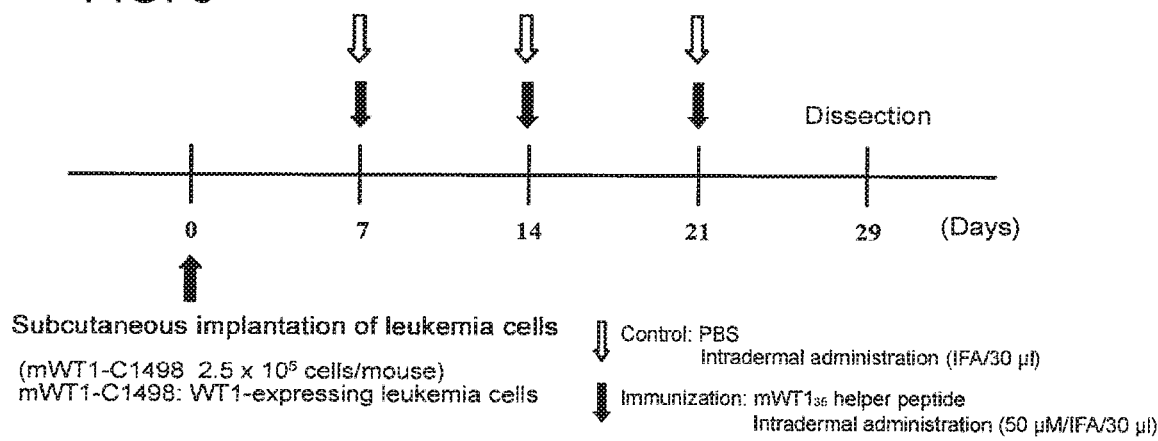
FIG. 6 shows a time-series schematic drawing when carrying out tumor implantation and immunization in a tumor implantation experiment. Immunization with an mWT1$_{3\ 5}$ helper peptide was carried out on the 7th, 14th and 21st days after subcutaneous implantation of WT1-expressing leukemia cells to mice, and dissection was carried out on the 29th day. Downward white arrows show time points at which a control (PBS) was intradermally administered (IFA/30 μl). Downward black arrows show time points at which an mWT1$_{3\ 5}$ helper peptide was intradermally administered (50 μM/IFA/30 μl).
Figure 7:
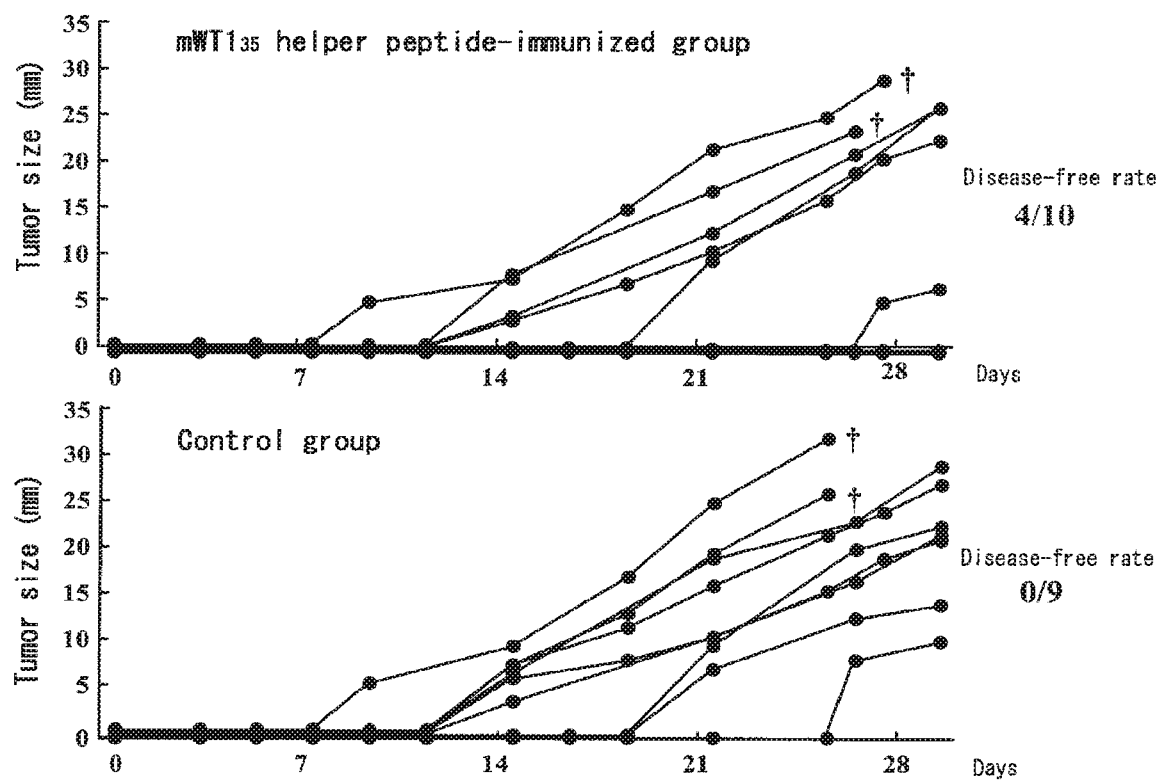
FIG. 7 shows tumor sizes in mice immunized with an mWT1$_{3\ 5}$ helper peptide and a proportion of disease-free mouse populations. In mice immunized with an mWT1$_{3\ 5}$ helper peptide, 4 of 10 mice were disease-free. On the other hand, in mice immunized with a control, there was no disease-free mouse in 9 mice.
Figure 8:
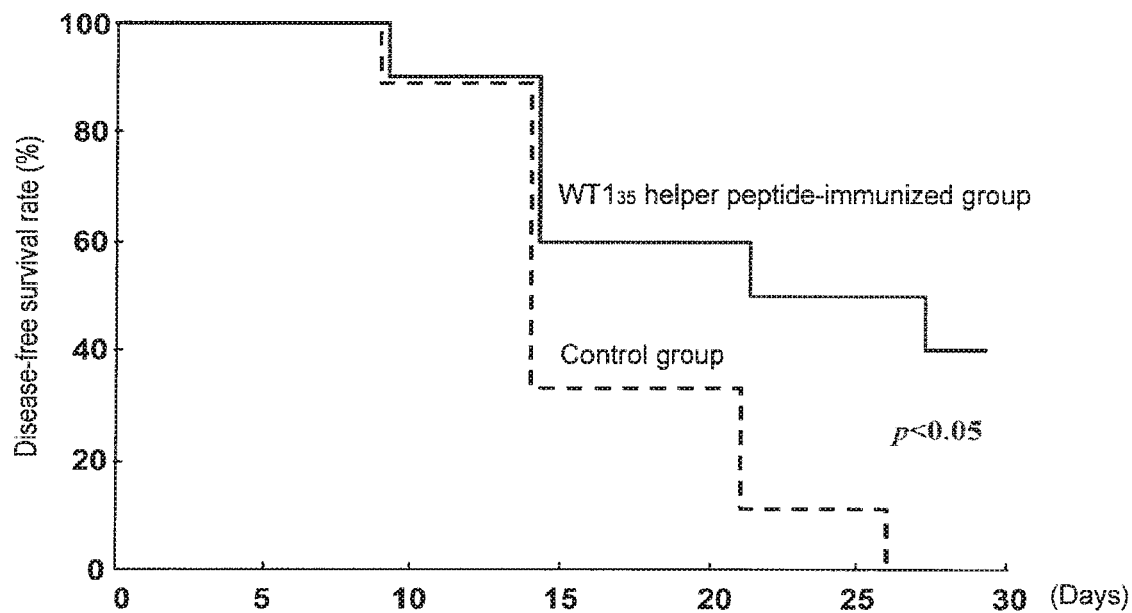
FIG. 8 shows a disease-free survival rate in mice immunized with an mWT1$_{3\ 5}$ helper peptide.

WT1-expressing C1498 leukemia cells were subcutaneously implanted in mice in a proportion of $2.5 \times 10^5$ cells per mouse, and 50 μg/mouse of a $WT1_{3\ 5}$ helper peptide was intradermally administered together with a Freund's incomplete adjuvant, once a week, 3 times in total, starting from one week after the implantation (FIG. 6). As a control, a physiological saline instead of the $WT1_{3\ 5}$ helper peptide was intradermally administered together with a Freund's incomplete adjuvant. The size of a subcutaneous tumor was measured over time, and the disease-free survival rate was calculated up to the 29th day after the subcutaneous implantation. As a result, the tumor expanded in all mice of the control group, while proliferation of the tumor was completely suppressed in 4 of 10 mice of the $WT1_{3\ 5}$ helper peptide (MHC class II)-immunized group (FIG. 7). Also, a significant difference ($p<0.05$) was recognized between the $WT1_{3\ 5}$ helper peptide-immunized group and the control group (FIG. 8). This demonstrated that the $WT1_{3\ 5}$ helper peptide (MHC class II) is a WT1 peptide having an ability to induce tumor immunization in vivo.

Figure 9:
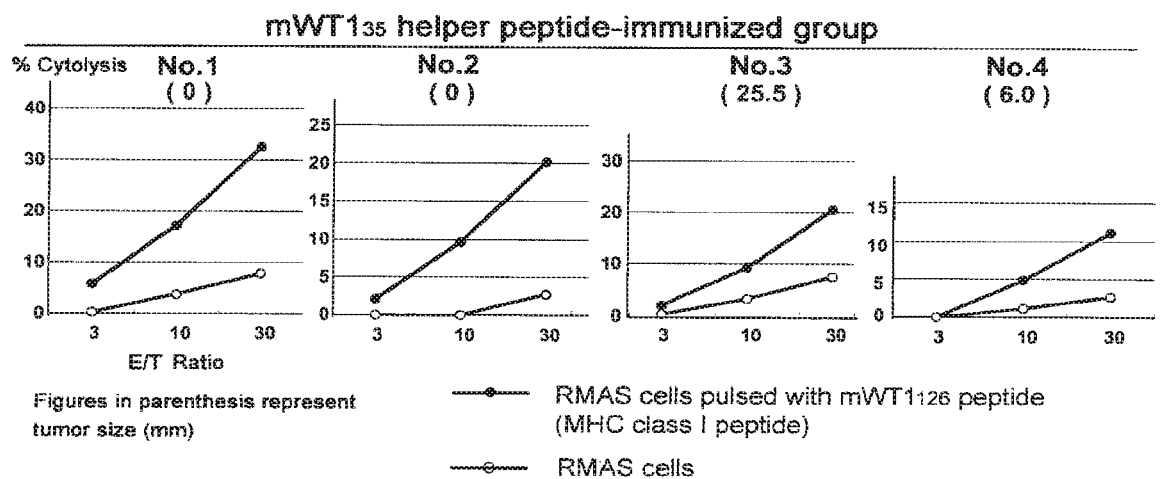
FIG. 9 shows cytotoxic activity of CTLs in mice immunized with an mWT1$_{3\ 5}$ helper peptide. ● shows the results of experiments carried out using RMAS cells pulsed with an mWT1$_{1\ 2\ 6}$ peptide (MHC I peptide). ○ shows the results of experiments carried out using control RMAS cells. The numerical in parenthesis represents a tumor size (mm).
Figure 10:
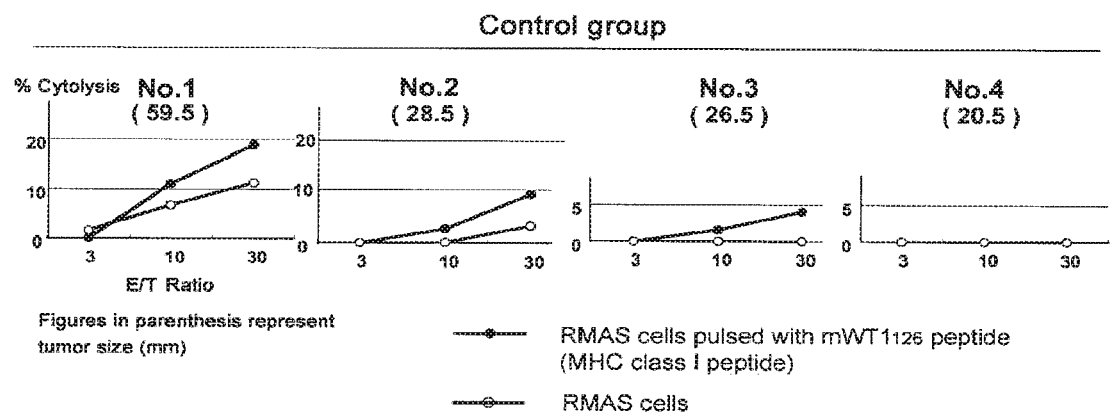
FIG. 10 shows cytotoxic activity of mWT1-specific CTLs in control mice. ● shows the results of experiments carried out using RMAS cells pulsed with an mWT1$_{1\ 2\ 6}$ peptide (MHC I peptide). ○ shows the results of experiments carried out using control RMAS cells. The numeral in parenthesis represents a tumor size (mm).

Next, mice were dissected on the 29th day after starting the above experiment, the spleen was excised, and a WT1-specific immune response was analyzed using spleen cells. Briefly, the spleen was excised when mice of the $WT1_{3\ 5}$ helper peptide (MHC class II)-immunized group and the control group were dissected, and spleen cells were prepared. The spleen cells were stimulated once with a $WT1_{1\ 2\ 6}$ peptide (MHC class I), and on the 6th day after the stimulation, cytotoxic activity of the spleen cells was measured using RMAS cells pulsed with a $WT1_{1\ 2\ 6}$ peptide (MHC class I) as a target cell. As a control, the cytotoxic activity of the spleen cells was measured using RMAS cells as a target cell. As a result, WT1-specific cytotoxic T cells were induced in all 4 mice of the $WT1_{3\ 5}$ helper peptide (MHC class II)-immunized group (FIG. 9). On the other hand, the WT1-specific cytotoxic T cells were very weakly induced in 3 mice of the control group (FIG. 10). The WT1-specific cytotoxic T cells were not induced in one mouse. Also, it was clear that the induction of the WT1-specific cytotoxic T cells was lower as compared with the $WT1_{3\ 5}$ helper peptide (MHC class II)-immunized group (FIGS. 9 and 10). This shows that WT1-specific helper T cells were induced by administration of a $WT1_{3\ 5}$ class II helper peptide, and by the action of the WT1-specific helper T cells, WT1-specific cytotoxic T cells induced by immune-responding to a WT1 protein expressed by implanted tumor cells were strongly amplified in vivo. Thus, the results demonstrated the usefulness of the $WT1_{3\ 5}$ helper peptide.

Figure 11:
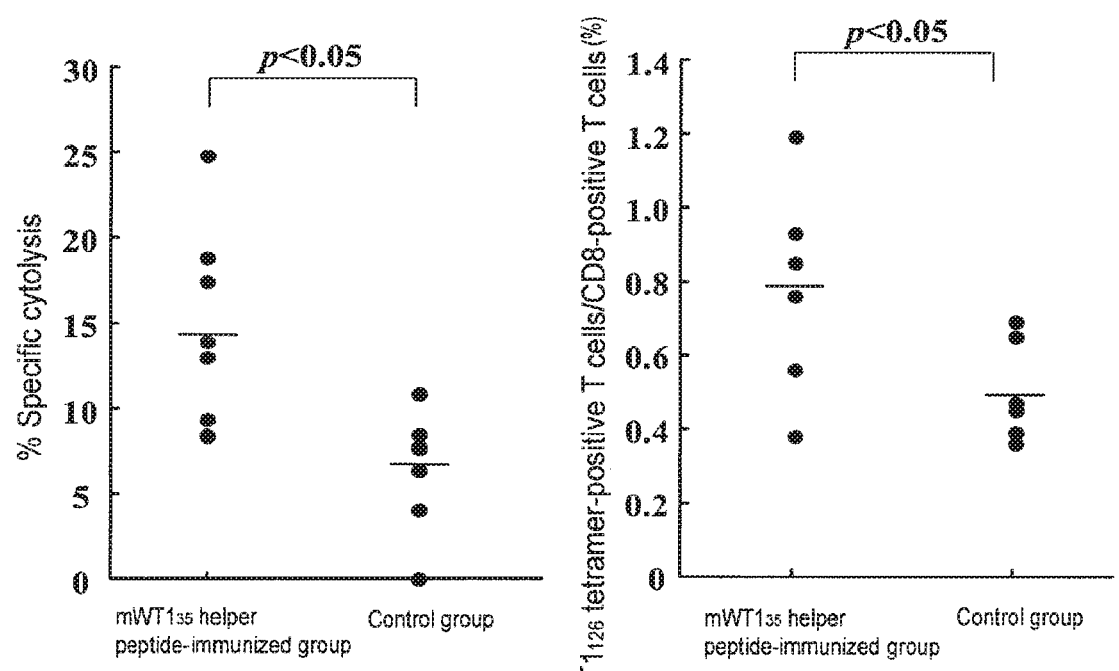
FIG. 11 shows cytotoxic activity of mWT1$_{1\ 2\ 6}$ peptide-specific CTLs (left) and a proportion of WT1$_{1\ 2\ 6}$ tetramer-positive T cells (right) when an mWT1$_{3\ 5}$ peptide was administered.

Next, specific cytolysis was analyzed in mice of the above $WT1_{35}$ helper peptide (MHC class II)-immunized group and control group. Briefly, the degree of cytolysis (%) obtained by subtracting the rate of cytolysis (%) when target cells were RMAS cells from the rate of cytolysis (%) when target cells were RMAS cells pulsed with a $WT1_{126}$ peptide (MHC class I) in the above experiments was used as the specific cytolysis (%) (FIG. 11, left). Also, the above-prepared spleen cells and a fluorescence-labeled WT1 tetramer (H-2 Db WT1 Tetramer-RMFPNAPYL-PE) were incubated at 4° C. for 20 minutes, washed, then stained with fluorescence-labeled CD3 and CD8 antibodies, again washed, and analyzed by FACS. CD3-positive, CD8-positive, and WT1 tetramer-positive cells were served as WT1-specific cytotoxic T cells (FIG. 11, right). As a result, significantly high WT1-specific cytotoxic T cells ($p<0.05$) were induced in spleen cells of mice of the $WT1_{35}$ helper peptide (MHC class II)-immunized group as compared with spleen cells of mice of the control group (FIG. 11).

Example 4

Figure 12:
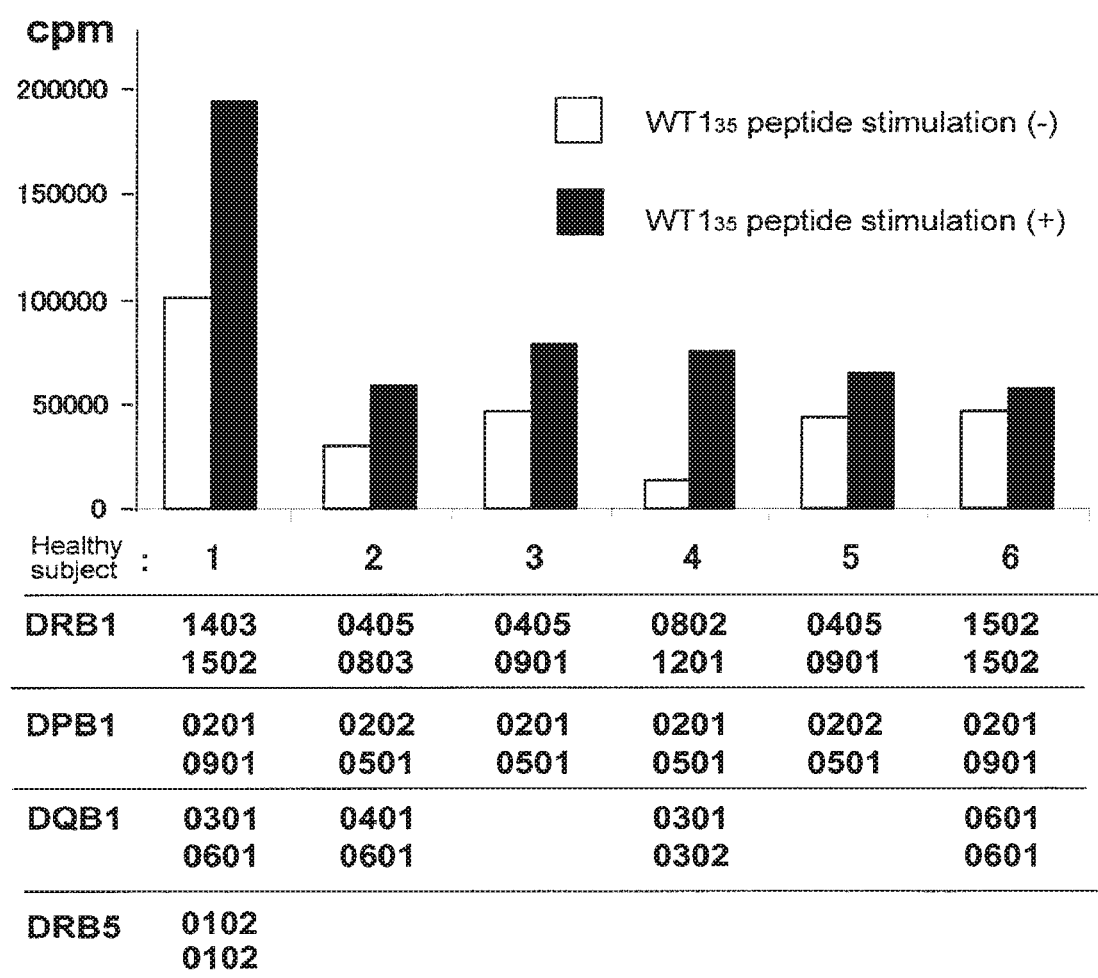
FIG. 12 shows the results obtained by measuring cell proliferation by WT1$_{3\ 5}$ peptide stimulation in peripheral blood mononuclear cells of each healthy subject having MHC class II molecules.

Measurement of Proliferation Ability of WT1-Specific Cytotoxic T Cells (CTLs) in Human Peripheral blood mononuclear cells were prepared from 6 healthy subjects having DRB1, DPB1, DQB1 or DRB5 subclass molecules as shown in FIG. 12. To the peripheral blood mononuclear cells, a $WT1_{3\ 5}$ helper peptide was added, and the cells were cultured for one week. Then, the peripheral blood mononuclear cells were stimulated 4 times in total at intervals of one week using identical subject-derived peripheral blood mononuclear cells, which were pulsed with a $WT1_{3\ 5}$ helper peptide and irradiated, as a stimulator, and $^3$H incorporation was measured on the 6th day. In all 6 healthy subjects, peripheral blood mononuclear cells responded to a $WT1_{3\ 5}$ helper peptide and proliferated (FIG. 12). This showed that the $WT1_{3\ 5}$ helper peptide has a function to bind to the mentioned HLA class II molecules and cause proliferation reaction. In this connection, the mouse $WT1_{8\ 6}$ peptide and $WT1_{2\ 9\ 4}$ peptide differ from the human $WT1_6$ peptide (SEQ ID NO:4) and $WT1_{2\ 9\ 4}$ peptide (SEQ ID NO:5) in one amino acid at the positions enclosed in squares, as shown in Table 8.

TABLE 8

Differences in sequences between mouse and human WT1₃₅, WT1₈₆ and WT1₂₉₄ peptides

| mWT1₃₅ | Mouse | WAPVLDFAPPGASAYGSL (SEQ ID NO: 3) | 18-mer |
| --- | --- | --- | --- |
| hWT1₃₅ | Human | WAPVLDFAPPGASAYGSL (SEQ ID NO: 3) | |
| mWT1₈₆ | Mouse | EQCLSAFTLHFSGQFTG (SEQ ID NO: 6) | 17-mer |
| hWT1₈₆ | Human | EQCLSAFTVHFSGQFTG (SEQ ID NO: 4) | |
| mWT1₂₉₄ | Mouse | FRGIQDVRPVSGVAPTLVR (SEQ ID NO: 7) | 19-mer |
| hWT1₂₉₄ | Human | FRGIQDVRRVPGVAPTLVR (SEQ ID NO: 5) | |

Example 5

HLA Class II Molecule-Restrictedness of WT1₃ ₅ Peptide

Figure 13:
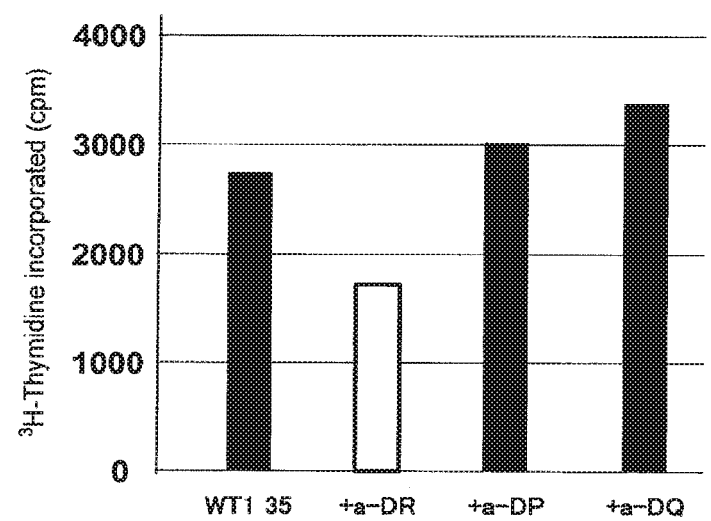
FIG. 13 shows the results obtained by measuring cell proliferation when a Responder [PBMCs derived from a DRB1*0101/0405-, DPB1*0201/0402-, and DQB1*0401/0501-positive healthy subject (healthy subject A)] was treated with a Stimulator [PBMCs derived from a DRB1*0405/0901-, DPB1*0201/0501-, and DQB1*0303/0401-positive healthy subject (healthy subject B)]. The ordinate shows the amount of $^3$H-thymidine incorporated (cpm). The abscissa shows the types of various antibodies added (no antibody, anti-HLA-DR antibody, anti-HLA-DP antibody, and anti-HLA-DQ antibody).

In order to determine HLA class II molecule-restrictedness of a WT1₃ ₅ peptide, a further experiment was carried out by a method well known to those skilled in the art as briefly described below. First, peripheral blood mononuclear cells (PBMCs) derived from a healthy subject [a DRB1*0101/0405-, DPB1*0201/0402-, and DQB1*0401/0501-positive healthy subject (hereinafter referred to as healthy subject A)] were stimulated 5 times with a WT1₃ ₅ peptide to prepare a Responder. Next, peripheral blood mononuclear cells (PBMCs) derived from another healthy subject different in an HLA class II type [a DRB1*0405/0901-, DPB1*0201/0501-, and DQB1*0303/0401-positive healthy subject (referred to as healthy subject B)] were pulsed with the WT1₃ ₅ peptide to prepare a Stimulator, and cell proliferation [the amount of ³H-thymidine incorporated (cpm)] was measured. The measurement was carried out under conditions of no addition of an antibody, addition of an anti-HLA-DR antibody (+a-DR), addition of an anti-HLA-DP antibody (+a-DP), or addition of an anti-HLA-DQ antibody (+a-DQ). A common HLA class II type, which is positive in both the Responder and Stimulator, shows restrictedness of the WT1₃ ₅ peptide. As a result of the experiments, it was shown that the WT1₃ ₅ peptide is DRB1*0405-restricted because the proliferation was suppressed under a condition having addition of an anti-DR antibody, and DRB10405 was common in healthy subjects A and B, as shown in FIG. 13.

Figure 14:
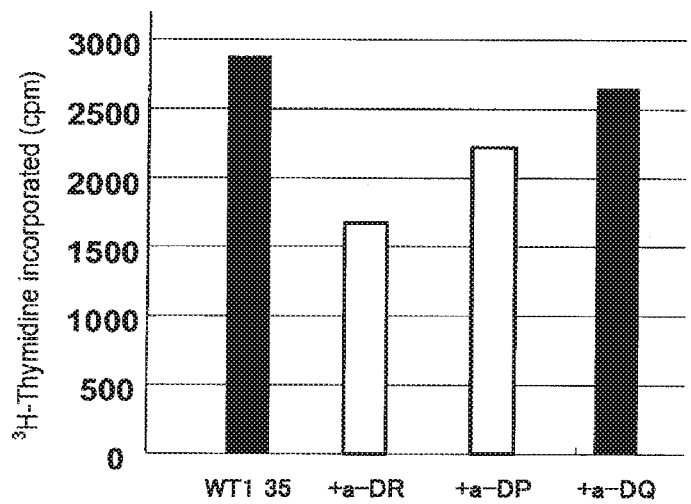
FIG. 14 shows the results obtained by measuring cell proliferation when a Responder [PBMCs derived from a DRB1*0101/0405-, DPB1*0201/0402-, and DQB1*0401/0501-positive healthy subject (healthy subject A)] was treated with a Stimulator [PBMCs derived from a DRB1*0405/0803-, DPB1*0202/0501-, and DQB1*0401/0601-positive healthy subject (healthy subject G)]. The ordinate shows the amount of $^3$H-thymidine incorporated (cpm). The abscissa shows the types of various antibodies added (no antibody, anti-HLA-DR antibody, anti-HLA-DP antibody, and anti-HLA-DQ antibody).

Next, an experiment was carried out under the same conditions as those of the above experiment, except that PBMCs derived from a healthy subject different from healthy subject A [DRB1*0405/0803-, DPB1*0202/0501-, and DQB1*0401/0601-positive healthy subject (referred to as healthy subject G)] were used as a Stimulator. As a result, it was shown that the WT1₃ ₅ peptide is DRB1*0405-, DPB1*0201- and DPB1*0202-restricted because the proliferation was suppressed under a condition having addition of an anti-HLA-DR antibody or an anti-HLA-DP antibody, and DRB1*0405, DPB1*0201 and DPB1*0202 were common in healthy subject A and healthy subject G (DPB1*0201 and DPB1*0202 have a high analogy and are cross-reactive, and therefore, they are considered as a common molecule), as shown in FIG. 14.

Figure 15:
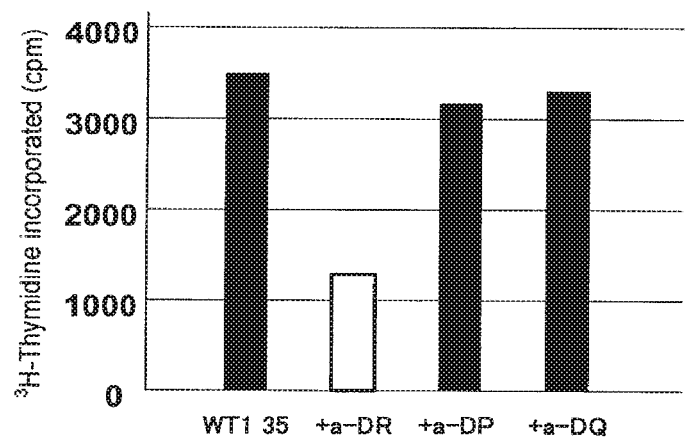
FIG. 15 shows the results obtained by measuring cell proliferation when a Responder [PBMCs derived from a healthy subject having DRB10101/0405, DPB10201/0402, and DQB1*0401/0501 (healthy subject A)] was treated with a Stimulator [PBMCs derived from a DRB10101/0803-, DPB1*0501/-, and DQB1*0501/0601-positive healthy subject (healthy subject H)]. The ordinate shows the amount of $^3$H-thymidine incorporated (cpm). The abscissa shows the types of various antibodies added (no antibody, anti-HLA-DR antibody, anti-HLA-DP antibody, and anti-HLA-DQ antibody).

Next, an experiment was carried out under the same conditions as those of the above experiment, except that PBMCs derived from a healthy subject different from healthy subject A [DRB1*0101/0803, DPB1*0501/-, DQB1*0501/0601-positive (referred to as healthy subject H)] were used as a Stimulator. As a result, it was shown that the WT1₃ ₅ peptide is DRB1*0101-restricted because the proliferation was suppressed under a condition having addition of an anti-HLA-DR antibody, and DRB1*0101 was common in healthy subject A and healthy subject H, as shown in FIG. 15.

Figure 16:
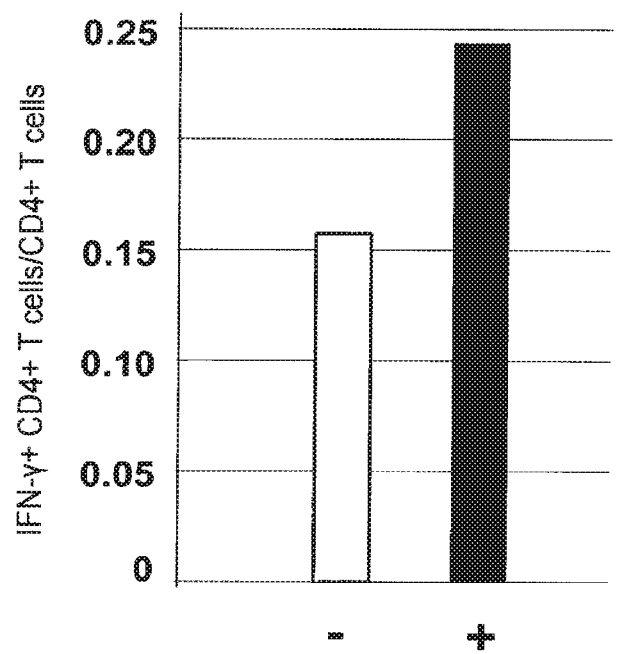
FIG. 16 shows the results obtained by measuring an IFN-γ producing ability when a Responder [PBMCs derived from a DRB10405/0803-, DPB1*0202/0501-, and DQB1*0401/0601-positive healthy subject (healthy subject G)] was treated with a Stimulator (L cells having a DQB1*0601 gene introduced). The ordinate shows a proportion of an amount of IFN-γ in T cells. The abscissa shows the presence or absence (+ or −) of a pulse with a WT1$_{3\ 5}$ peptide.

Moreover, PBMCs derived from healthy subject G were used as a Responder and L cells having a DQB1*0601 gene introduced were used as a Stimulator, in order to determine restrictedness of a WT1₃ ₅ peptide. The difference in an amount of IFN-γ produced in the presence or absence of a pulse with a WT1₃ ₅ peptide of L cells was measured. A proportion of intracellular IFN-γ production was measured using FACS which is a technique well known to those skilled in the art. As a result, it was shown that the WT1₃ ₅ peptide is DQB1*0601-restricted because the Responder was activated by the pulse with a WT1₃ ₅ peptide on L cells, as shown in FIG. 16.

Next, an experiment was carried out as described above using PBMCs derived from the same healthy subject as a Responder and a Stimulator. The types of HLA class II molecules possessed by healthy subjects used in this experiment were summarized in Table 9 below.

TABLE 9

Types of HLA class II molecules possessed by healthy subjects used in this experiment

| Healthy subject No. | DRB1 | DPB1 | DQB1 |
| --- | --- | --- | --- |
| A | *0101/0405 | *0201/0402 | *0401/0501 |
| B | *0405/0901 | *0201/0501 | *0303/0401 |
| C | *0802/1201 | *0201/0501 | *0301/0302 |
| D | *1502/1502 | *0201/0901 | *0601/0601 |
| E | *0405/0901 | *0202/0501 | *0303/0401 |
| F | *1403/1502 | *0201/0901 | *0301/0601 |
| G | *0405/0803 | *0202/0501 | *0401/0601 |
| H | *0101/0803 | *0501/— | *0501/0601 |
| I | *0101/1501 | *0201/0402 | *0501/0602 |

Figure 17:
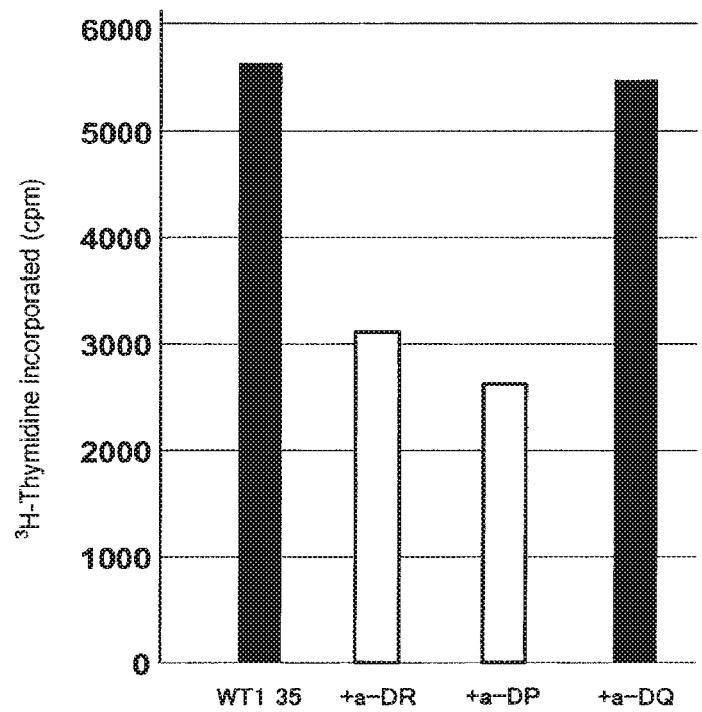
FIG. 17 shows the results obtained by measuring cell proliferation when a Responder [PBMCs derived from a DRB1*1502/1502-, DPB1*0201/0901-, and DQB10601/0601-positive healthy subject (healthy subject D)] was treated with a Stimulator (PBMCs derived from the same healthy subject as in the Responder). The ordinate shows the amount of $^3$H-thymidine incorporated (cpm). The abscissa shows the types of various antibodies added (no antibody, anti-HLA-DR antibody, anti-HLA-DP antibody, and anti-HLA-DQ antibody).

As a result, it was found that addition of an anti-DR antibody or an anti-DP antibody, when the experiment was carried out using PBMCs derived from healthy subjects A to E, resulted in reduction of the amount of ³H-thymidine incorporated (cpm), and therefore, in suppression of the proliferation. Also, addition of only an anti-DR antibody, when PBMCs derived from healthy subject F were used, resulted in suppression of the proliferation. Moreover, addition of only an anti-HLA-DP antibody, when PBMCs derived from healthy subject G were used, resulted in suppression of the proliferation. By an experiment using healthy subject A, it was shown that the WT1₃ ₅ peptide is DRB1*0101- or 0405-restricted, and DPB1*0201- or 0402-restricted. By an experiment using healthy subject B, it was shown that the WT1₃ ₅ peptide is DRB1*0405- or 0901-restricted, and DPB1*0201- or 0501-restricted. By an experiment using healthy subject C, it was shown that the WT1₃ ₅ peptide is DRB1*0802- or 1201-restricted, and DPB1*0201- or 0501-restricted. By an experiment using healthy subject D, it was shown that the WT1₃ ₅ peptide is DRB1*1502-restricted because the DRB1*1502 is a homozygote (FIG. 17). In addition, it was shown that the WT1₃ ₅ peptide is DPB1*0201- or 0901-restricted. By an experiment using healthy subject E, it was shown that the WT1₃ ₅ peptide is DRB1*0405- or 0901-restricted, and DPB1*0202- or 0501-restricted. By an experiment using healthy subject F, it was shown that the WT1₃₅ peptide is DRB1*1403- or 1502-restricted. By an experiment using healthy subject G, it was shown that the WT1₃₅ peptide is DPB1*0202- or 0501-restricted.

Figure 18:
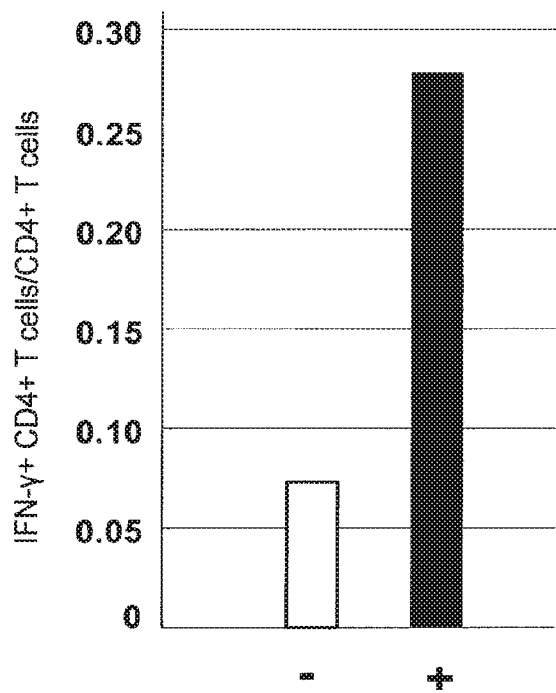
FIG. 18 shows the results obtained by measuring an IFN-γ producing ability when a Responder [PBMCs derived from a DRB1*0101/1501-, DPB1*0201/0402-, and DQB1*0501/0602-positive healthy subject (healthy subject I)] was treated with a Stimulator (PBMCs derived from the same healthy subject as in the Responder). The ordinate shows a proportion of an amount of IFN-γ in T cells. The abscissa shows the presence or absence (+ or −) of a pulse with a WT1$_{3\ 5}$ peptide.

Also, the difference in an amount of IFN-γ produced in the presence or absence of a pulse with a WT1₃₅ peptide was measured using PBMCs derived from healthy subject I as a Responder and a Stimulator. A proportion of intracellular IFN-γ production was measured using FACS which is a technique well known to those skilled in the art. As a result, a proportion of an amount of IFN-γ remarkably increased by the pulse with a WT1₃₅ peptide (FIG. 18). This shows that the WT1₃₅ peptide is restricted by any one of DRB1*0101, DRB1*1501, DPB1*0201, DPB1*0402, DQB1*0501, and DQB1*0602.

INDUSTRIAL APPLICABILITY

The present invention provides a WT1 peptide which is restricted by many types of MHC class II molecules, a polynucleotide encoding the peptide, a pharmaceutical composition containing them and the like. Thus, they can be utilized in the field of pharmaceuticals, for example, the field of the development and production of prophylactic or therapeutic drugs for various hematopoietic organ tumors and solid tumors which highly express a WT1 gene.

[Sequence Listing Free Text]

---

The invention claimed is:

1. A peptide that induces WT1-specific helper T cells by binding to an MHC class II molecule, wherein the peptide consists of an amino acid sequence in which one to three amino acids are substituted in the amino acid sequence depicted in SEQ ID NO:5.

2. The peptide according to claim 1, wherein the MHC class II molecule is selected from the group consisting of DRB1*0101, DRB1*0405 DRB1*0802, DRB1*0803, DRB1*0901, DRB1*1201, DRB1*1403, DRB1*1501, DRB1*1502, DPB1*0201, DPB1*0202, DPB1*0402, DPB1*0501, DPB1*0901, DQB1*0301, DQB1*0302, DQB1*0401, DQB1*0501, DQB1*0601, DQB1*0602 and DRB5*0102.

3. The peptide according to claim 1, wherein the MHC class II molecule is selected from the group consisting of DRB1*0101, DRB1*0405 DRB1*1502, DPB1*0201, DPB1*0202 and DQB1*0601.

4. A pharmaceutical composition for treating or preventing cancer, comprising the peptide according to claim 1.

5. A method for treating or preventing cancer, which comprises administering an effective amount of the peptide according to claim 1 to a subject having an MHC class II molecule selected from the group consisting of DRB1*0101, DRB1*0405, DRB1*0802, DRB1*0803, DRB1*0901, DRB1*1201, DRB1*1403, DRB1*1501, DRB1*1502, DPB1*0201, DPB1*0202, DPB1*0402 DPB1*0501, DPB1*0901, DQB1*0301, DQB1*0302 DQB1*0401, DQB1*0501, DQB1*0601, DQB1*0602, and DRB5*0102.

6. Antigen presenting cells which display the peptide according to claim 1 through an MHC class II molecule selected from the group consisting of DRB1*0101, DRB1*0405, DRB1*0802, DRB1*0803, DRB1*0901, DRB1*1201, DRB1*1403, DRB1*1501, DRB1*1502, DPB1*0201, DPB1*0202, DPB1*0402, DPB1*0501, DPB1*0901, DQB1*0301, DQB1*0302, DQB1*0401, DQB1*0501, DQB1*0601, DQB1*0602, and DRB5*0102.

7. A method for inducing antigen presenting cells, which comprises culturing immature antigen presenting cells in the presence of the peptide according to claim 1, and inducing antigen presenting cells, which display the peptide through an MHC class II molecule selected from the group consisting of DRB10101, DRB1*0405, DRB1*0802, DRB1*0803, DRB1*0901, DRB1*1201, DRB1*1403, DRB1*1501, DRB1*1502, DPB1*0201, DPB1*0202, DPB1*0402, DPB10501, DPB1*0901, DQB1*0301, DQB1*0302, DQB1*0401, DQB1*0501, DQB1*0601, DQB1*0602, and DRB5*0102, from the immature antigen presenting cells.

8. WT1-specific helper T cells which are induced by the peptide according to claim 1.

9. A method for inducing WT1-specific helper T cells, which comprises culturing peripheral blood mononuclear cells in the presence of the peptide according to claim 1, and inducing WT1-specific helper T cells from the peripheral blood mononuclear cells.

10. A kit for inducing WT1-specific helper T cells, comprising, as an essential ingredient, the peptide according to claim 1.

11. A kit for preventing or treating cancer, comprising, as an essential ingredient the peptide according to claim 1.

12. A method for determining the presence or amount of WT1-specific helper T cells in a subject having an MHC class II molecule which is selected from the group consisting of DRB1*0101, DRB1*0405, DRB1*0802, DRB1*0803, DRB1*0901, DRB1*1201, DRB1*1403, DRB1*1501, DRB1*1502, DPB1*0201, DPB1*0202, DPB1*0402, DPB1*0501, DPB1*0901, DQB1*0301, DQB1*0302, DQB1*0401, DQB1*0501, DQB1*0601, DQB1*0602, and DRB5*0102,
wherein said method comprises the steps of:
(a) reacting the peptide according to claim 1 with a sample derived from the subject; and
(b) determining the presence or amount of a cytokine contained in the sample.

* * * * *

UNITED STATES PATENT AND TRADEMARK OFFICE
CERTIFICATE OF CORRECTION

PATENT NO. : 11,732,018 B2
APPLICATION NO. : 16/937619
DATED : August 22, 2023
INVENTOR(S) : Haruo Sugiyama It is certified that error appears in the above-identified patent and that said Letters Patent is hereby corrected as shown below:

In the Claims

Claim 2, Column 125, Line 18, "DRB1*0405 DRB1*0802," should read --DRB1*0405, DRB1*0802,--.

Claim 2, Column 125, Line 22, "DQB1*0602 and" should read --DQB1*0602, and--.

Claim 3, Column 125, Line 26, "DRB1*0405 DRB1*1502," should read --DRB1*0405, DRB1*1502,--.

Claim 3, Column 125, Line 27, "DPB1*0202 and" should read --DPB1*0202, and--.

Claim 5, Column 125, Line 36, "DPB1*0402 DPB1*0501," should read --DPB1*0402, DPB1*0501,--.

Claim 5, Column 125, Line 37, "DQB1*0302 DQB1*0401," should read --DQB1*0302, DQB1*0401,--.

Claim 7, Column 126, Line 14, "DRB10101," should read --DRB1*0101,--.

Claim 7, Column 126, Line 17, "DPB10501," should read --DPB1*0501,--.

Signed and Sealed this
Tenth Day of October, 2023

Katherine Kelly Vidal
*Director of the United States Patent and Trademark Office*